US005667764A

United States Patent [19]
Kopia et al.

[11] Patent Number: 5,667,764
[45] Date of Patent: Sep. 16, 1997

[54] COMPOUNDS, COMPOSITIONS AND METHODS FOR BINDING BIO-AFFECTING SUBSTANCES TO SURFACE MEMBRANES OF BIO-PARTICLES

[75] Inventors: Gregory A. Kopia, Phoenixville; Paul K. Horan, Downingtown; Brian D. Gray, Ardmore; David E. Troutner, Phoenixville; Katharine A. Muirhead, West Chester; Kamleshkumar A. Sheth, Downingtown; Chia-En Lin, Norristown; Zhizhou Yu, Jeffersonville; Bruce D. Jensen, Collegeville; Sue Ellen Slezak, Downingtown, all of Pa.

[73] Assignee: Zynaxis, Inc., Malvern, Pa.

[21] Appl. No.: 884,432

[22] Filed: May 15, 1992

Related U.S. Application Data

[63] Continuation-in-part of Ser. No. 189,192, May 2, 1988, abandoned.

[51] Int. Cl.[6] .................... A61K 51/04; C07D 209/02; C07D 263/62; C07D 513/04

[52] U.S. Cl. .................... 424/1.45; 424/1.53; 424/1.65; 424/1.69; 424/1.73; 424/1.81; 424/1.85; 530/327; 540/478; 536/21; 548/121; 548/156; 548/159; 548/219; 548/455; 548/457; 548/458

[58] Field of Search .................... 424/7.1, 9, 1.45, 424/1.65, 1.69, 1.73, 1.81, 1.85; 534/10; 530/300, 327, 402, 409, 324, 383; 536/21; 548/100, 156, 159, 219, 455, 121, 457, 458; 436/544, 545, 546, 519, 520; 540/478

[56] References Cited

U.S. PATENT DOCUMENTS

| | | | |
|---|---|---|---|
| 2,647,054 | 7/1953 | Vinton et al. | 95/7 |
| 4,427,649 | 1/1984 | Dingle et al. | 424/38 |
| 4,471,113 | 9/1984 | MacCoss | 536/29 |
| 4,473,652 | 9/1984 | Okazaki et al. | 436/536 |
| 4,501,728 | 2/1985 | Geho et al. | 424/38 |
| 4,689,292 | 8/1987 | Metoki et al. | 430/567 |
| 4,751,219 | 6/1988 | Kempen | 514/26 |
| 4,762,701 | 8/1988 | Horan et al. | 424/1.1 |
| 4,783,401 | 11/1988 | Horan et al. | 435/34 |
| 4,859,584 | 8/1989 | Horan et al. | 435/29 |
| 4,867,973 | 9/1989 | Goers et al. | 424/85.91 |
| 4,906,749 | 3/1990 | Theodoropulos | 544/69 |
| 5,132,290 | 7/1992 | Priebe et al. | 514/34 |
| 5,149,794 | 9/1992 | Yatvin et al. | 536/29 |
| 5,194,654 | 3/1993 | Hostetler et al. | 558/152 |
| 5,223,263 | 6/1993 | Hostetler et al. | 424/450 |
| 5,246,951 | 9/1993 | Galet et al. | 514/359 |

FOREIGN PATENT DOCUMENTS

| | | |
|---|---|---|
| 0353450 | 6/1989 | European Pat. Off. . |
| WO8910758 | 11/1989 | WIPO . |
| WO9003401 | 4/1990 | WIPO . |
| WO9116024 | 10/1991 | WIPO . |
| WO9117424 | 11/1991 | WIPO . |

OTHER PUBLICATIONS

Solomons, *Organic Chemistry*, 4th Ed., 1986, pp. 843–847.

Honig et al., *J. Cell Biology*, vol. 103 "Fluorescent Carbocyanine Dyes . . . " pp. 171–187, (1986).

Ryu et al., *J. Med. Chem.*, vol. 25, "Phospholipid–Nucleoside Conjugates . . . ", pp. 1322–1329 (1982).

Heath et al., *Biochim. Biophys. Acta*, vol. 862 "Liposome–mediated delivery . . . " pp. 72–80, (1986).

*J. Immun. Methods*, vol. 117, Slezak et al., "Cell–mediated cytotoxicity . . . " pp. 205–214 (1989).

Chemical Abstracts, 81:129819 Moebius *Photogr. Sci. Eng.* (1974) vol. 18(4) pp. 413–418.
J.J. Castellot, Jr. et al., J. Cell Biol., 102: 1979–1984 (1986).
G.A. Grode et al., Trans. Am. Soc. Artif. Int. Organs, 15: 1–6 (1969).
J.W. Currier et al., Circulation, 80: II–66 (1989).
C.L. Grines et al., Circulation, 84: II–365 (1991).
J.S. Powell et al., Science, 245: 186–188 (1989).
C. Lundergan et al., J. Am. Coll. Cardiol., 67 (Suppl. B): 132B–136B (1991).
L. Jonasson et al., Proc. Natl. Acad. Sci., 85: 2303–2306 (1988).
G.A.A. Ferns et al., Science, 253: 1129–1132 (1991).
G.M. Nemecek et al., J. Pharm. Exp. Thera., 248: 1167–1174 (1989).
M.W. Liu et al., Circulation, 81: 1089–1093 (1990).
G.K. Hansson and J. Holm Circulation, 84: 1266–1272 (1991).
N. Gschwend, Textbook of Rheumatology, (eds. W.N. Kelly et al.), W.B. Saunders, pp. 1934–1961 (1989).
T.H. Ji, Meth. Enz., 91: 580–609 (1983).
D.J. Gale et al., Aust. J. Chem., 30: 689–694 (1977).
J. Sondermann, Liebigs Ann. Chem., 749: 183–197 (1971).
B. Dhawan and P.L. Southwick, Orgn. Prep. and Proc. Int., 7 (2): 85–88 (1975).

(List continued on next page.)

*Primary Examiner*—John Kight
*Assistant Examiner*—Lara E. Chapman
*Attorney, Agent, or Firm*—Dann, Dorfman, Herrell and Skillman

[57] ABSTRACT

Compounds are provided having the capability of binding therapeutically active substances to lipid containing biocompatible particles, such as cells or viruses. These compounds include a bio-affecting moiety, comprising a therapeutically active substance, which is linked via a linking moiety to at least one hydrocarbon substituent selected so that the compounds is sufficiently non-polar to impart lipid binding capability to the compound. Thus, compounds of the invention are useful for site-selective delivery of therapeutic agents, and retention thereof at the selected site.

Methods are provided for using various compounds of the invention in treatment of diseases or other pathological conditions. For example, methods are provided for treatment of: (1) post-angioplasty restenosis; (2) rheumatoid arthritis; (3) tumor cell proliferation, particularly tumor cells associated with ovarian cancer; and (4) psoriasis.

12 Claims, 6 Drawing Sheets

OTHER PUBLICATIONS

B.R. Costa et al., J. Labelled Cmpds. and Radiopharm., XXVII: 1015–1024 (1989).

R. Wetzel et al., Bioconjugate Chem., 1: 114–122 (1990).

D.G. Hoare and D.E. Koshland, Jr., J. Biol. Chem., 242: 2447–2453 (1967).

A.J. Brake and B.H. Weber, J. Biol. Chem., 249: 5452–5457 (1974).

P. Bohlen et al., Int. J. Peptide Protein Res., 16: 306–310 (1980).

K. Hofmann et al., J. Am. Chem. Soc, 100: 3585–3590 (1978).

M.F. Moreau et al., Eur. J. Med. Chem.—Chimica Therapeutica, 9: 274–280 (1974).

H. Azizian et al., J. Organomet. Chem., 215: 49–58 (1981).

D.S. Wilbur et al., J. Nuc. Med., 30: 216–226 (1989).

M.J. Weiss et al., J. Labelled Cmpds. and Radiopharm., XXVI: 109–110 (1989).

A. Brossi, J. Med. Chem., 33: 2311–2319 (1990).

W–C. Shen and H. J.–P. Ryser, Biochem. Biophys. Res. Comm., 102, 3: 1048–1054 (1981).

K. Srinivasachar and D.M. Neville, Jr., Biochemistry, 28: 2501–2509 (1989).

B.C. Laguzza et al., J. Med. Chem., 32: 548–555 (1989).

G.T. Shiau et al., J. Pharma. Sci., 64: 646–648 (1975).

B.M. Mueller et al., Bioconjugate Chem., 1: 325–330 (1990).

H. Eckert and B. Forster, Angew. Chem. Int. Ed. Engl., 26: 894–95 (1987).

K.E. Baidoo and S.Z. Lever, Tetrahedron Lett., 31: 5701–5704 (1990).

M.–R. Spirlet et al., Inorg. Chem., 23: 4278–4283 (1984).

M.W. Sundberg et al., J. Med. Chem., 17: 1304–1307 (1974).

T.N. Rao et al., J. Am. Chem. Soc., 112: 5798–5804 (1990).

F. Celada and B. Rotman, Proc. Natl. Acad. Sci., 57: 630–636 (1967).

S.E. Slezak and P.K. Horan, Blood, 74: 2172–2177 (1989).

S.E. Slezak and P.K. Horan, J. Immunol. Meth., 117: 205–214 (1989).

M.J. Melnicoff et al., J. Leuk. Biol., 43: 387–397 (1988).

Proceedings of SPIE (Society of Photo–Optical Instrumentation Engineers)—The International Society for Optical Engineering, vol. 847, New Directions in Photodynamic Therapy, D.C. Neckers, Editor; (Oct. 1987).

P. Lee, J. Rheumatol., 9: 165–167 (1982).

C.B. Sledge et al., Clin. Ortho and Rel. Res., 182: 37–40 (1984).

W.A. Volkert et al., J. Nucl. Med., 32; 174–185 (1991).

J.L. Humm, J. Nucl. Med., 27: 1490–1497 (1986).

J.L. Humm and L.M. Cobb, J. Nucl. Med., 31: 75–83 (1990).

C.A. Hoefnagel, Anti–Cancer Drugs, 2: 107–132 (1991).

Bochner et al., Handbook of Clinical Pharmacology, Little Brown and Co., Boston (1983), pp. 151–152.

G. Gomori, Meth. Enz., I: 138–146 (1955).

U. Forstermann et al., J. Pharm. Exp. Ther., 243: 1055–1061 (1987).

J.–L. Beny and P.C. Brunet, J. Physiol., 398: 277–289 (1988).

B.W. Kimes and B.L. Brandt, Exptl. Cell Res., 98: 349–366 (1976).

J.L. Krstenansky and S.J.T. Mao, FEBS Let., 211: 10–16 (1987).

Ryu et al., J. Med. Chem., 25: 1322–29 (1982).

MacCoss et al., Biochemical and Biophysical Research Communications, 85: 714–23 (1978).

Heath et al., Biochimica et Biophysica Acta, 862: 72–80 (1986).

Trouet et al., PNAS U.S.A., 70: 626–29 (1982).

- ■ SP
- ● SP + [D-Pro$^2$, D-Trp$^{7,9}$]-SP
- ▲ Conjugate
- ◆ Conjugate + [D-Pro$^2$, D-Trp$^{7,9}$]-SP

COMPOUNDS, COMPOSITIONS AND METHODS FOR BINDING BIO-AFFECTING SUBSTANCES TO SURFACE MEMBRANES OF BIO-PARTICLES

This application is a continuation-in-part of U.S. patent application Ser. No. 189,192, filed May 2, 1988, now abandoned, entitled "Compounds, Compositions and Methods for Binding Bio-Affecting Substances to Surface Membranes of Bio-Particles".

FIELD OF THE INVENTION

The present invention relates to compounds, compositions and methods for binding bio-affecting substances, such as therapeutic and, optionally, diagnostic agents, to bio-compatible particles, including both viable cells and viruses, and non-viable carrier particles. This invention is also directed to starting materials and intermediates used in the preparation of such compounds. The invention also relates to the use of the compounds for site-selective delivery of therapeutic and, optionally, diagnostic agents in vivo.

BACKGROUND INFORMATION

The delivery of therapeutic agents for the treatment of diseases and other pathological conditions may be accomplished by various means. These include oral, intravenous, subcutaneous, transdermal, intramuscular administration or topical application. For some therapeutic agents, the existing modes of delivery either are unable to deliver sufficient dosages to the disease site without adverse systemic side effects or are unable to allow sufficient retention of the therapeutic product at the disease site for a time sufficient to produce the intended therapeutic effect.

Drugs that prevent or reduce the proliferation of pathological cell types are essential to the treatment and control of various diseases involving undesirable or uncontrolled cell proliferation. But antiproliferatives, by definition, must be toxic to certain cell types. It is often not feasible to administer these drugs systemically, because the amounts needed to control the diseased cell types may be toxic or deadly to the patient's normal cells. This difficulty could be circumvented by administering antiproliferative agents directly to the site of the undesired cell proliferation. A mechanism is also needed for retaining antiproliferative agents at the disease site, so that they may effectively control the proliferation of undesired cells, while being restrained from migrating and damaging normal cell types.

Specific diseases and conditions for which site-specific delivery and retention of anti-proliferatives would be particularly effective are briefly described below. Each of these conditions involves the proliferation of a particular undesirable cell type, and systemic administration of drug therapy for their treatment has not yielded optimal results.

1. Post-Angioplasty Reocclusion and Restenosis

Atherosclerotic lesions, which limit or obstruct coronary blood flow, are the major cause of coronary heart disease-related mortality. Direct intervention has been employed via percutaneous transluminal coronary angioplasty (PTCA) or coronary artery bypass graft.

A major difficulty with PTCA is the problem of post-angioplasty closure of the vessel, both immediately after PTCA (acute reocclusion) and in the long term (restenosis).

Restenosis after angioplasty is a response to injury of the interior arterial wall caused by the angioplasty procedure. While the exact mechanism is still under active investigation, in general, it appears to involve proliferation of smooth muscle cells of the arterial medial layer, followed by migration of these cells to the inner (intimal) layer, where cells continue to proliferate. Proliferation usually ceases within the intima within 7–14 days post-injury.

Patients with symptomatic reocclusion require further PTCA or coronary artery bypass graft. Because such a large percentage (30–50%) of patients undergoing PTCA experience restenosis, the success of PTCA as a therapeutic approach to coronary artery disease is clearly limited.

Attempts to prevent restenosis by pharmacologic means typically involve systemic administration of various agents, and have been generally unsuccessful.

Several antiproliferative agents being actively studied for prevention of restenosis are described more fully below.

a. Heparin and Heparin Fragments

Heparin is a highly anionic heterogeneous glycosaminoglycan consisting of repeating disaccharide units of α-D-glucuronic acid and N-acetyl-D-glucosamine which are extensively sulfated. The primary therapeutic use of heparin is as an anticoagulant. However, heparin is also known to inhibit the growth of several different cell types, including vascular smooth muscle cells (SMC). Heparin fragments as small as tetra- saccharides, with only weak or no anticoagulant action, have been found to possess antiproliferative activity in vitro and in vivo. Castellot et al., J. Cell Biol., 102: 1979–1984 (1986).

Heparin binds to SMC cell surfaces via high affinity binding sites and is taken up intracellularly. Heparin can also be coupled to various artificial surfaces, such as silicone, Mylar®, Dacron®, polycarbonate, polyethylene and polypropylene, through ionic association with a tridodecyl methylammonium chloride coating. See Grode et al., Trans. Am. Soc. Artif. Int. Organs, 15: 1 (1969).

No data are available as to whether the antiproliferative activity of heparin is retained when coupled to such materials.

b. Colchicine

Colchicine is a naturally occurring alkaloid used in the therapeutic control of acute gouty arthritis. Colchicine arrests plant and animal cell division both in vitro and in vivo by preventing mitotic spindle fiber formation, thus arresting cell division in metaphase. This action of colchicine is similar to that of the vinca alkaloids, vincristine and vinblastine. Recently, it has been reported that colchicine administered daily to rabbits with atherosclerotic iliac arteries reduced the degree of restenosis observed on angiography at four (4) weeks post-balloon injury. Currier et al., Circulation, 80, 11–66 (1989).

However, in a recent clinical study, 1 mg/day of colchicine failed to reduce the incidence of restenosis in patients who underwent balloon angioplasty. C. Grines et al., Circulation, 84: II-365 (1991). Due to limiting toxicity, patients could not tolerate more than 1 mg/day, a dose which is estimated to result in a blood colchicine level between 10 and 20 times lower in humans than that in the rabbit study.

c. Other Agents

Other agents which have been employed in animal models and have produced a reduction of myointimal thickening are: (1) Angiotensin Converting Enzyme (ACE) Inhibitors (J. Powell et al., Science, 245: 186–188 (1989); (2) Angiopeptin (C. Lundergan et al., Am. J. Cardiol., 17 (Suppl. B): 132B–136B (1991)); (3) Cyclosporin A (L. Jonasson et al., Proc. Natl. Acad. Sci., 85: 2303–06 (1988)); (4) goat anti-rabbit platelet-derived growth factor antibody (G. Ferns et al., Science, 253: 1129–1132 (1991)); (5) Terbinafine (G. Nemecek et al., J. Pharmacol. Exp. Theta., 248: 1167–1174 (1989)); (6) Trapidil (M. Liu et al., Circulation, 81: 1089–1093 (1990); and (7) interferon-gamma (G. Hansson et al., Circulation 84: 1266–72 (1991)).

Using systemic drug delivery, such as oral administration, to treat post-angioplasty restenosis involves periodic administration at fixed intervals, and consequent cyclic variations in concentration of the therapeutic agent at the disease site. Furthermore, over the 20–30 day period when the patient must receive systemic administration of the drug, greater than 99% of the drug ingested is typically processed through the liver or kidney, depending on the drug. This represents an opportunity for serious adverse reactions.

2. Rheumatoid Arthritis

Rheumatoid arthritis is a chronic disorder characterized by chronic synovitis of the joints. Though there is no existing cure for rheumatoid arthritis, one recognized treatment is synovectomy, which involves the removal of inflamed soft tissue in the affected joints. N. Gschwend, *Textbook of Rheumatology*, (eds. W. N. Kelly et al.), W. B. Saunders, pp. 1934–1961 (1989). Synovectomy can be achieved surgically, chemically or radio-pharmaceutically. Surgical synovectomy has been demonstrated to have a palliative effect on pain. In most cases, however, there is a recurrence of the synovitis in the years following the surgery. Moreover, surgical synovectomy can be performed only once on each joint and is difficult to perform on relatively small joints. Chemical synovectomy has been shown to be an effective alternative to surgical synovectomy, but its use has been limited by the toxicity of currently available agents to cartilage and bone.

Radioisotope synovectomy, as an alternative to chemical synovectomy, appears to inhibit synovial proliferation. However, the use of radioisotope synovectomy is limited because, insofar as is known, delivery systems used to date require prolonged immobilization of the affected joint or use of very short-lived and commercially unfeasible isotopes to reduce to acceptable levels systemic release of radioisotope to the lymph nodes, spleen or liver. The leakage of radioisotope from the site of synovectomy is the primary concern in the development of this procedure for early treatment of rheumatoid arthritis.

3. Ovarian Cancer

Ovarian cancer is the fourth leading cause of cancer death in women. Epithelial carcinomas account for approximately 80% to 90% of ovarian malignancies. Epithelial carcinomas spread through the body primarily by surface shedding or lymphatic spread. The most common type of extra-ovarian spread is transperitoneal dissemination of cells shed from the surface of the primary tumor.

Surgery, the primary treatment for ovarian cancer, is rarely a complete cure, because carcinoma cells typically enter the peritoneal cavity early in the disease and cannot be surgically removed. External beam radiotherapy is also often used before or after surgery; however, dose levels are restricted by the limited tolerance of the abdominal organs (liver, kidneys, stomach and intestines) to the radiation. Intraperitoneal instillation of radioactive colloidal gold or phosphorus to irradiate the peritoneal cavity was utilized in the past. Its use has diminished, however, because of inhomogeneous distribution of the radiation and complications in the small bowel. Monoclonal antibodies are currently being tested as vehicles for radioisotopes delivered intraperitoneally. To date, none of these monoclonal antibody conjugates has received approval for ovarian cancer treatment.

Chemotherapy is the most common form of treatment of patients with advanced ovarian cancer. Drugs currently used against ovarian cancer may prolong life by a few years. However, they present very significant side effects at the recommended systemic dose levels.

4. Psoriasis

Psoriasis is a common, chronic skin disease that progresses into an uncontrolled growth of skin keratinocytes, creating inflammation and ulceration. No comprehensive cure for psoriasis is available to date.

Current treatments for psoriasis are both systemic and topical. Though both types of treatment are effective, they can cause serious adverse side effects. Systemic treatment of psoriasis includes principally the administration of corticosteroids and cytotoxic compounds such as methotrexate. Topical treatments include anti-bacterial or anti-fungal preparations, tars, phototherapy using sun exposure or ultra-violet light, or the application of topical steroids. Topical corticosteroids are used for psoriasis more than any other therapeutic modality. However, topical treatments suffer the disadvantage of being easily rubbed or washed off, thus impairing their long-term efficacy. Use of topical corticosteroids is also limited by their tendency to penetrate into the peripheral blood vessels and thence into the general circulation, causing undesirable systemic buildup.

A mode of administering pharmacotherapy which would permit greater concentration and retention of the therapeutic agent at the disease site without serious side effects, may prove useful in treating the above-described conditions.

Recent research efforts have focused on the utility of specific biological interactions, e.g. receptor-ligand or antigen-antibody interactions, in the development of target-specific therapeutic or diagnostic agents. Another promising area of research involves target-specific cells or vesicles (e.g., liposomes) containing an appropriate diagnostic or therapeutic agent. Specifically, monoclonal antibodies have been used to impart target specificity to these cells or vesicles. Because it is a relatively new technology, such methods of targeted drug therapy are not yet truly effective or reliable.

In International Application No. PCT/US89/00087, there are described various compounds, compositions, their methods of preparation and use in binding bio-affecting substances to the surface membrane of bio-particles, such as cells or viruses, without producing appreciable detrimental effect on cell morphology or physiological function. The compounds are of the general formula $R\text{-}B\text{-}R_1$, in which B represents a bio-affecting substance, e.g. a therapeutic or diagnostic agent, and at least one of R and $R_1$ is a hydrocarbon substituent selected so as to impart a degree of lipophilicity to the compound that enables stable association with the surface membrane of bioparticles. Compositions including the compounds just described are formulated with a compatible binding medium for stable association between the compound and the outer surface membrane of the bioparticle. These compositions are utilized for exerting a site-specific predetermined effect in vivo by stably binding the compound to a selected bioparticle having a natural or acquired affinity for the predetermined site and introducing the bioparticle in vivo, whereby the bioparticle carries the bio-affecting substance to the predetermined site to produce its intended effect.

SUMMARY OF THE INVENTION

In accordance with one aspect of the present invention, compounds are provided having the capability of binding therapeutically active substances to lipid containing bioparticles, e.g., cells or viruses. The compounds of the invention include a bio-affecting moiety, comprising a therapeutically active substance which is stably linked via a linking moiety to at least one hydrocarbon substituent selected so as to render the compounds sufficiently non-polar that they are capable of stable binding to lipid components of lipid-containing bio-compatible particles either in vivo or in vitro. The compounds optionally include a spacer moiety to provide separation between the therapeutic substance and the linking moiety, as required to mediate therapeutic activity.

The compounds of the invention are further characterized by having varying but predictable stabilities of association with the lipid component of biomembranes. The compounds are sufficiently non-polar as to have a surface membrane retention coefficient (MRC) of at least 90% and a membrane binding stability of at least 30%. The compounds of the invention should also be sufficiently stable in use that the therapeutic agent, once delivered to the selected site, either by direct administration or via a carrier, remains there for a time and in an amount sufficient to produce its intended effect. Procedures for determining membrane retention coefficient and membrane binding stability are described in detail hereinbelow.

In accordance with the present invention, the above-described compounds are used for site-selective delivery of therapeutic agents, and retention thereof at the selected site. According to a preferred aspect of the invention, the therapeutic agent has an anti-proliferative action, useful for the treatment of diseases or other pathological conditions involving cell proliferation. The anti-proliferative agent may comprise a radiotherapeutic substance or a chemotherapeutic substance. According to a preferred embodiment, the present invention provides compounds wherein the radiotherapeutic substance comprises a chelating agent and a radiometal. In another preferred embodiment, the compounds of the invention comprise chemotherapeutic substances such as heparin, hirudin and derivatives thereof, as well as agents capable of interfering with selected intracellular functions.

According to another aspect of the invention, chemotherapeutic substances may be releasably conjugated to compounds of the invention. Such chemotherapeutic substances may be selected, for example, from the group consisting of colchicine, vinca alkaloids, taxol and derivatives thereof, which exhibit their bioeffect only upon release from the compounds. These compounds interfere with tubulin synthesis assembly, dissassembly or degradation, and/or function, which are hereinafter collectively referred to as "tubulin processes". For example, there is provided an acid-cleavable colchicine derivative, in which the colchicine analog incorporated therein is essentially inactive as long as it remains conjugated to the linker moiety. The compound is delivered to a selected site and eventually taken into the cell. Uptake of the compound is accompanied by a lowering in pH, which effects cleavage of the colchicine moiety from the linker moiety. The liberated colchicine analog is capable of exerting its intended biological effect, which is to interfere with tubulin processes.

According to a further aspect of the invention, there are provided pharmaceutical preparations comprising the compounds of the invention in compatible biological media.

According to yet another aspect of the invention, there are provided methods of using various compounds of the invention, comprising therapeutically active substances, and optionally including diagnostic agents, in the treatment of diseases or other pathological conditions.

The compounds of the invention are preferably administered by direct in vivo delivery for retention at the disease site. Alternatively, the compounds may be bound to carrier particles adapted to direct the compound to the disease site. Direct in vivo delivery is particularly preferred for treatment of conditions such as post-angioplasty restenosis, rheumatoid arthritis, ovarian cancer and psoriasis, and will be described in further detail hereinbelow.

The present invention possesses a number of distinct advantages as compared with compounds and methods currently available for delivery of therapeutic agents to disease sites. Most notably, compounds of the invention may be delivered and retained at a selected site in the body by stable association with cell structures at that site. Existing modes of delivery either are unable to deliver sufficient dosages to the disease site without adverse systemic side effects, or are unable to allow sufficient retention of the therapeutic products at the disease site for a time and in an amount sufficient to produce the desired therapeutic effect. Compounds of the invention will enable attainment of a therapeutically effective dose at the disease site. For example, in the case of radiotherapy, where systemic distribution of a radioisotope is highly undesirable, compounds of the invention enable stable association and retention of the radiotherapeutic substance at the site where it is needed, and limit systemic distribution of the isotope without requiring immobilization of the joint or use of extremely short lived isotopes.

Another notable advantage of the present invention is that compounds may be formulated such that they are initially stably associated with the external cell membranes and subsequently taken up into the cell through normal membrane trafficking processes. This feature, coupled with the ability to formulate compounds of the invention comprising releasably conjugated therapeutic agents, allows for the delivery of potentially toxic substances to selected cell interiors, where they may become activated and exert their therapeutic effect on those cells alone and not on other cells of the body. The delivery of antisense RNA or DNA may also be accomplished in this manner.

A further advantage of this invention is that binding of the compounds described herein to cells and other bio-compatible particles occurs primarily through lipid affinity. This is particularly significant in the case of cells because binding in lipids reduces the chance of interfering with the important functional domains of a cell membrane which lie on the discrete protein portions and not in the more extensive lipid regions. Previous procedures which rely on binding to membrane proteins and cell receptors to deliver bio-affecting substances to cells often result in diminished functional capacity.

There are certain concomitant benefits realized from binding in the lipid region of cells. Since the lipid regions comprise the majority of the cell surface area, it is possible to place larger numbers of lipid binding compounds, and thus a greater concentration of therapeutic agent, into the plasma membrane. Moreover, because the compounds of the invention are stably incorporated into membrane lipids due to their lipophilic character, they are relatively insoluble in normal physiological salts. Accordingly, once these compounds are bound to the membrane, they are effectively trapped there and cannot dissociate easily. Consequently, leakage from the cells is minimized, thereby minimizing undesirable systemic effects.

BRIEF DESCRIPTION OF THE DRAWINGS

Referring to the drawings herein,

FIG. 3 is a series of fluorescence/frequency histograms wherein the points represent individual cells; increasing distance of the points from the origin on the x axis represents increasing red fluorescence intensity (LFL2 signal), whereas increasing distance of the points from the origin on the y axis represents increasing green fluorescence intensity (LFL1 signal);

DESCRIPTION OF THE PREFERRED EMBODIMENTS

I. Definitions

Figure 1A:
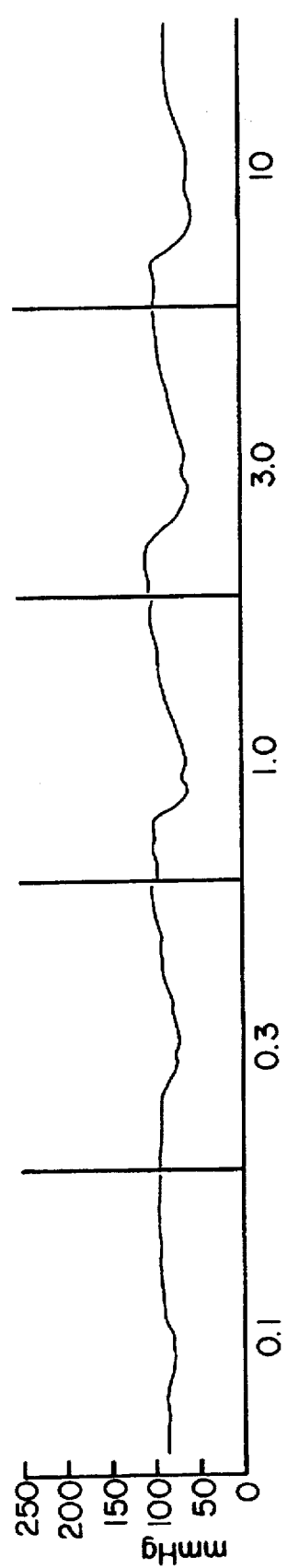
FIG. 1 shows the results of tests comparing the vascular response of locally injected Substance P versus a substance P-lipophilic cyanine conjugate of the invention. The upper graph pertains to Substance P; the lower graph pertains to the conjugate.
Figure 1B:
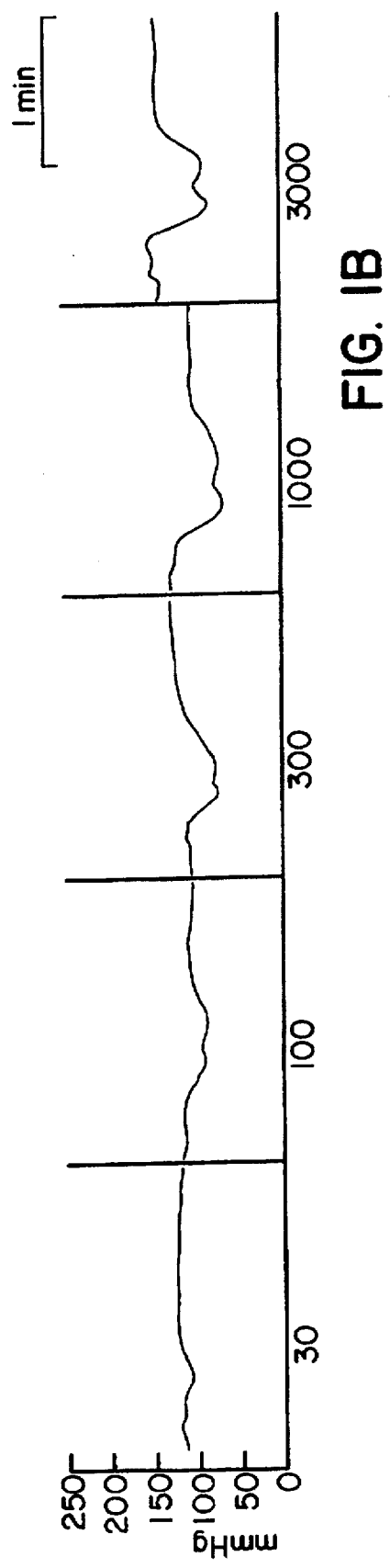

The words and phrases listed below are defined for reference in describing the present invention as follows:

1. Bio-affecting moiety—The terms bio-affecting moiety and bio-affecting substance are used interchangeably herein to refer to a wide variety of different substances useful in the therapeutic, diagnostic, prophylactic or other treatment of humans or animals. These include any substances capable of exerting a biological effect.

2. Bio-compatible particle—The term "bio-compatible particle", as used herein, includes both viable entities, e.g. cells, both in vivo and in vitro, as well as non-viable entities, such as liposomes and lipoproteins, so long as they do not give rise to a serious adverse reaction upon administration in vivo.

The expression "viable bio-compatible particle capable of physiological function" is used herein to refer to any viable cell or membrane-containing virus. Moreover, as used herein, the term "cell" includes prokaryotic cells, such as bacteria, as well as eukaryotic cells, such as white blood cells, various tumor cells, and mammalian cells in culture, e.g. chinese hamster ovary cells, yeast, and non-nucleated cells, such as red blood cells, red blood cell ghosts and platelets. The detailed description of the invention hereinbelow is set forth with particular reference to cells of a living body. It should be understood, however, that what is stated with respect to cells is generally applicable to membrane-containing viruses, as well. It should be further understood that in carrying out site-selective delivery of therapeutic agents in accordance with this invention, non-viable entities may be suitably substituted for viable entities provided they have a natural or acquired affinity for the intended delivery site. For example, liposomes may be used as carriers for therapeutically active substances to be delivered to the liver or spleen.

3. Diagnostic Agent—Refers to a compound or substance capable of facilitating the detection, determination or analysis of a physiological condition or state by an in vivo or in vitro test. In use, the compounds of the invention may serve a dual function as reporter molecules that may be detectable from outside the body, or may be detected in a body fluid or biopsy obtained for analysis in vitro.

4. Chromophore—Refers to a substance capable of being detected, either visually or instrumentally, by absorption of at least one selected wavelength of light.

5. Therapeutically active substance—Refers to a substance capable of preventing, alleviating, treating or curing abnormal or pathological conditions of the living body. These include substances capable of maintaining, increasing, decreasing, limiting or destroying a physiologic body function, as well as substances for protecting a living body by inhibiting, killing, modifying or retaining a microorganism or antigen thereof. Therapeutically active substances include pharmaceutical agents or drugs with therapeutic utility.

6. Chemotherapeutic substance—Refers to a therapeutically active substance whose therapeutic effect arises from the chemical characteristics of the substance. Chemotherapeutic substances may include, for example, non-radioactive pharmaceuticals. They may include small molecules or more complex molecules such as lipids, carbohydrates, proteins or nucleic acids such as DNA or RNA.

7. Radiotherapeutic substance—Refers to a therapeutically active substance whose therapeutic effect arises from its radioactivity. Suitable radiotherapeutic substances may comprise radioisotopic atoms. Preferably, the bio-affecting moiety comprises a chelating agent complexed with various therapeutic radionuclides, such as $^{186}$Re, $^{90}$Y, $^{67}$Cu, $^{177}$Lu or $^{153}$Sm.

8. Antiproliferative agent—Refers to a therapeutically active substance capable of arresting, reducing or preventing the proliferation of cells.

II. Description of Compounds

Compounds of the invention are useful in various pharmacotherapies in which site-selective delivery of therapeutically active substances is desired. According to a preferred embodiment of the invention, the therapeutically active substance is an antiproliferative agent, which may be a radiotherapeutic or chemotherapeutic substance. In an alternative embodiment, the compounds of the invention may comprise a diagnostic agent, such as a chromophore or radionuclide, which enables tracking and/or detection of the compound of the invention in vitro or in vivo. Thus, compounds of the invention may comprise, for example, a therapeutically active substance as the bio-affecting moiety and a detectable chromophore as the linking moiety.

The diagnostic agents constituting the compounds of the invention may be selected from diverse classes of substances that are detectable by various analytical procedures known to those skilled in the art. Detectable fluorescent compounds are preferably cyanine dyes and their derivatives, including, e.g. oxycarbocyanine, indocarbocyanine, thiocarbocyanine or acridine dyes and derivatives thereof. Other useful fluorescent compounds include, for example, styrylpyridine, xanthene, phenoxazine, phenothiazine or diphenylhexatriene dyes and derivatives thereof.

Useful diagnostic agents may also include ligands which facilitate detection, such as biotin or specific antibodies. Other useful diagnostic agents are chelating substances complexed with metals, which may be directly or indirectly detectable. A suitable chelate-metal complex may comprise an isotope selected from the transition metal series whose atomic number is from 21–49, e.g. Indium-111 or Technetium-99m. Such complexes may be bound to the cell plasma membrane of carrier cells, rendering them radioactive so as to permit imaging using a gamma camera after delivery into the body. Chelating substances may also be complexed with an ionic species of metal which is indirectly detectable, e.g. by reason of certain effects produced thereby at the site of interest. Complexes of paramagnetic elements, for example, are capable of influencing the relaxation times of nearby nuclei, which is detectable by magnetic resonance imaging (MRI). Chelate-metal complexes comprising a metal ion selected from the transition metal series whose atomic number is 21-29 or the lanthanide series, whose atomic number is 59-66 may be suitable for such purposes.

Compounds comprising radioisotopic atoms may also be used, if desired, in the various applications of this invention. A radioisotope such as $^{125}I$, $^{131}I$, $^{14}C$, $^{3}H$, $^{35}S$ or $^{75}Se$ may be substituted for the more abundant but non-radioactive forms of the naturally occurring atoms present in the bio-affecting moiety, chromophore or the hydrocarbon tail portion of the compound. Isotopes having non-zero spin states (e.g., $^{19}F$) may also be introduced into the compounds of the invention, so as to make their presence detectable using MRI techniques.

For therapeutic applications, the bio-affecting moiety may comprise a chelating agent of the type described above, complexed with various therapeutic radionuclides, such as $^{186}Re$, $^{90}Y$ or $^{67}Cu$.

Proteinaceous substances, including proteins, glycoproteins, lipoproteins or peptides may also be coupled through suitable linking moiety to hydrocarbon tails of appropriate lengths for therapeutic applications in accordance with the present invention. Representative bio-affecting proteinaceous substances are immunogens, toxins, hormones, enzymes, antigens, antibodies and antibody fragments. Such therapeutically active proteins are beneficially conjugated to lipophilic chromophores, of the type described above, with the resultant conjugate being marked by varying but predictable stability of association with a variety of lipid-containing bioparticles, as exemplified hereinbelow.

In another therapeutic application, the bio-affecting moiety comprises a carbohydrate capable of altering the migration and circulation patterns within the body of cells to which it is bound. One class of carbohydrates applicable in this way includes sialic acids; another includes the glycosaminoglycans. For example, a formulation comprising a sialic acid could be applied to the plasma membrane of red cells to increase the number of sialic acids on the membrane. The increase in the number of charged groups should increase the lifetime of the red cells in circulation before removal in the liver.

The bio-affecting moiety may also be in the form of a ligand capable of binding to tissue-specific receptors or receptors on cells within target organs. Compounds containing such ligands, when bound, for example, to carrier cells, would enhance migration to specific organ sites.

Compounds of the invention can be delivered directly to selected sites in the body by a variety of means, including injection, infusion, catheterization and topical application, among others. Compounds of the invention also may be bound to carrier bio-compatible particles, e.g., autologous, allogenic or zenogenic cells, to facilitate targeted delivery of the bio-affecting substance. Unless otherwise specified, the discussion set forth below refers to binding of compounds of the invention to viable cells, either by direct delivery to the disease site, or in the preparation of carrier vehicles. One objective of the present invention is to provide compounds to which therapeutic drugs or radioisotopes may be attached and which are soluble in the lipid bilayer that constitutes the outer membrane of cells. Delivery of therapeutic substances via the compounds of the invention will enable these substances, when delivered directly to the disease site, to be retained on cells in the affected area in higher concentrations and for longer time periods than would otherwise be achievable. Moreover, using compounds of the invention can enable the use of therapeutic agents which otherwise might be toxic if administered systemically.

The mode of action of a compound of the invention on a cell is variable and depends on: (1) the type of cell to which it attaches; (2) the nature, length and number of the lipophilic tails; (3) the body site being treated; (4) the nature of the bio-affecting moiety; and (5) the mechanism by which the bio-affecting moiety being attached to the compound produces its effect upon the cell. A compound of the invention is deposited on the cell and initially attaches to the outer lipid bilayer of the plasma membrane. Because membrane components naturally traffic inward, these compounds will also be taken inside the cell. -The rate at which this occurs will vary depending on the particular cell type, its growth state and its level of activation or stimulation.

Some types of antiproliferative agents, such as radiotherapeutic substances conjugated to a compound of the invention, will be active whether they are localized on the outer membrane or within the cell. These agents emit radiation which damages the nucleus and, if the radiation is sufficiently penetrating, will inhibit growth of surrounding cells as well. Drugs that must physically interact with components inside the cell to inhibit growth will be effective only after the compound of the invention is taken into the cell. Another mode of action has also been designed whereby extremely toxic drugs, such as colchicine, can be conjugated to a lipophilic moiety and bound to the outer membrane in an inactive form which is not toxic to the cell. Then, as the conjugate traffics inwardly, a specially prepared linkage (described in greater detail in the following examples) allows the drug to be released from the conjugate and to exert its antiproliferative action.

III. General Formulae

Compounds within the scope of the invention are those of the formula:

wherein B represents a bio-affecting moiety comprising a therapeutically effective substance, R and $R_1$ represent substituents which are independently selected from the group of hydrogen, alkyl, alkenyl, alkynyl, alkaryl or aralkyl, the hydrocarbon chains of which are linear or branched, and which are unsubstituted or substituted with one or more non-polar functional groups, at least one of R and $R_1$ comprising a hydrocarbon substituent, the chain length of which is effective to impart membrane binding capability to the compound, $R_2$ represents a spacer moiety, n being 0 or 1, and L represents a linking moiety providing stable association between B and at least one of R and $R_1$, when n=0, and between $R_2$ and at least one of R and $R_1$, when n=1, with the proviso that when n=0, L is a non-aromatic linking moiety.

As used herein, the expression "non-polar functional group" refers to substituents such as O-alkyl, S-alkyl, halogen, $N(alkyl)_2$, Se-alkyl, $NO_2$, CN, CO-alkyl, $Si(alkyl)_3$, $O-Si(alkyl)_3$, and the like.

The linking moiety (L) may be a saturated or unsaturated aliphatic linker or a ring structure, including alicyclics and aromatics, which may be monocyclic, polycyclic, homocyclic, heterocyclic, fused or unfused.

Preferably, the linking moiety is a chromophore. Incorporation of a chromophore in the compounds of the invention facilitates tracking of the compounds in vivo. Useful chromophores for this purpose include: cyanine, acridine, pyridine, quinoline, xanthene, phenoxazine, phenothiazine and diphenyl hexatriene dyes and derivatives thereof.

A preferred class of compounds within the scope of the invention are those of the formula:

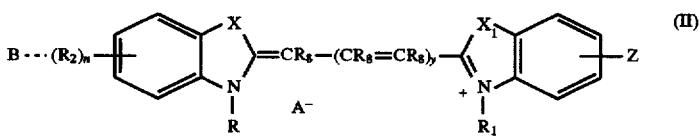

wherein B represents a bio-affecting substance, R and $R_1$ represent substituents independently selected from the group of hydrogen, alkyl, alkenyl, alkynyl, alkaryl or aralkyl, the hydrocarbon chains of which having from 1 to about 30 carbon atoms, and being linear or branched, said substituents being unsubstituted or substituted with one or more nonpolar functional groups, $R_2$ represents a spacer moiety of the formula: $—(R_3)_p—Q—(R_4-Q')_q—(R_5—Q")_r—(R_6—Q''')_s—(R_7Q'''')_t$, wherein $R_3$ represents an aliphatic hydrocarbon, $R_4$, $R_5$, $R_6$, and $R_7$ are independently selected from the group consisting of aliphatic, alicyclic, or aromatic hydrocarbons, heterocycles or $CH_2C(CO_2H)=CH$, Q and Q', Q'', Q''' and Q'''' are independently selected from the group of functional linkages consisting of amide, thiourea, hydrazone, acyl hydrazone, ketal, acetal, orthoester, ester, anhydride, disulfide, urea, carbamate, imine, amine, ether, carbonate, thioether, sulfonamide, carbonyl, amidine and triazine linkages; Q', Q'', Q''', Q'''' may additionally independently represent a valence bond, the aliphatic or alicyclic hydrocarbons having from 1 to 12 linear carbon atom and the aromatic hydrocarbons having from 6 to 12 carbon atoms; n, p, q, r, s and t each may be either 0 or 1;

X and $X_1$ may be the same or different and represent O, S, $C(CH_3)_2$ or Se;

$R_8$ is independently selected from the group consisting of H, $CH_3$, $CH_2CH_3$, $CH_2CH_2CH_3$ or $CH(CH_3)_2$ and y may be from 0–3;

Z represents a substituent selected from the group H, alkyl, OH, —O—alkyl, COOH, $CONH_2$, $SO_3H$, $SO_2NH_2$, CONH-alkyl, CON-$(alkyl)_2$, NH-acyl, NH-alkyl, $N(alkyl)_2$, SH, S-alkyl, $NO_2$, halogen, $Si(alkyl)_3$ or $O-Si(alkyl)_3$, $Sn(alkyl)_3$ or Hg-halogen, the alkyl groups comprising said Z substituent having from 1 to 4 carbon atoms; and A represents a biologically compatible anion. For applications requiring highly stable biomembrane binding, one of R or $R_1$ in formula (II) should have at least 12 carbon atoms and the sum of linear carbon atoms in R and $R_1$ should total at least 23.

Various spacer moieties ($R_2$) may readily be incorporated between the cyanine head group and the bio-affecting moiety via suitable functionalities present on either or both the head group or the bio-affecting moiety, following well known synthetic routes. A large number of different types of bifunctional (homobifunctional and heterobifunctional) spacer reagents have been reported in the technical literature for such purpose. See Meth. Enz., 91: 580–609 (1983). These spacer moieties differ according to type(s) of reactive groups, hydrophobicity or hydrophilicity, length and whether the structure connecting the reactive groups is clearable or not.

As noted above, the functional linkage of the spacer group may be an amide (—NHCO—), thiourea (—NHCSNH—), hydrazone (=NHN—), acyl hydrazone (=NHNCO—), ketal (—O—C(alkyl)$_2$—O—), acetal (—O—CH(alkyl)—O—), orthoester (—C(O-alkyl)$_2$—O—), ester (—COO—), anhydride (—COOCO—), disulfide (—S—S—), urea (—NHCONH—), carbamate (—NH—CC=O)—O—), imine (=N—), amine (—NH—), ether (—O—), carbonate (—O—C(=O)—O—), thioether (—S—), sulfonamide (—SO$_2$—NH—), carbonyl (—CO—) and amidine (—NHC=(NH⊕—)).

In a preferred embodiment for radiotherapy, B represents a chelating agent complexed with a radiometal, such as rhenium or yttrium, among others. In preferred embodiments for chemotherapy, B represents heparin, hirudin, colchicine, vinblastine or analogs thereof, all of which are antiproliferative agents. In another preferred embodiment for chemotherapy, B represents a peptide. A derivative of the peptide known as Substance P, falling within formula II above, has been found to bind stably to red cells and to provide a protracted therapeutic effect in circulation, as compared with the free, i.e. unconjugated, peptide. It is anticipated that enhanced bioavailability can be similarly achieved for other therapeutically active substances having relatively short lifetimes in circulation when in unconjugated form.

In certain applications of the compounds of the invention, e.g., combined therapy and diagnosis, B in formula I may advantageously be biotin.

III. Preparation of Compounds of the Invention

1. Lipophilic Functionalized Cyanines

The compounds of formula (II) above are conveniently prepared from lipophilic cyanine precursors of the following general formula:

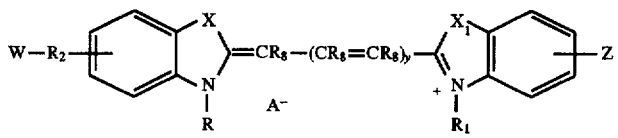

(III)

wherein R, $R_1$, X, $X_1$, Z and A are as defined above with reference to the compounds of formula II; and $R_2$ represents a spacer moiety of the formula: —$(R_3)_p$—$(Q-R_4)_q$—$(Q'-R_5)_r$—$(Q''-R_6)_s$—$(Q'''-R_7)_t$—wherein $R_3$, $R_4$, $R_5$, $R_6$, $R_7$, $R_8$, Q, Q', Q'', Q''', p, q, r, s t and y are as defined above with reference to the compounds of formula II; and W represents a reactive functionality selected from the group amino (—$NH_2$), α-haloacetamido (—NH COCH$_2$-hal) (hal=halogen), isothiocyanate (—NCS), halogen, isocyanate (—NCO), carboxyl (—COOH), hydrazino (—$NHNH_2$), acylhydrazido(—CONH—$NH_2$), ketone (—RCO), e.g., benzophenone, dithiopyridyl (—SS—$C_5H_5N$), sulfhydryl (—SH), aldehyde (—HCO), anhydride (—COOCO—alkyl), succinimide ester (—COOO$C_4H_4NO_2$), hydroxyl (—OH), sulfonyl halide (—$SO_2$-hal), imidoester (—C(=NH)OCH$_3$), epoxide (—$C_2H_3O$) maleimidyl (—NCOCH=CHCO) and azido (—$N_3$).

Suitable precursors for preparing the compounds of the invention, having a reactive amine ($NH_2$) group as substituent W in the above formula, can be prepared according to various synthetic routes, one of which is illustrated in Reaction Scheme 1 and discussed in detail in the examples below.

According to Scheme 1, 2,3,3-(3H-trimethylindolenine (commercially available) is reacted with N-hydroxymethylphthalamide (commercially available) according to the procedure of Gale and Wilshire, *Aust. J. Chem.*, 30:693 (1977) to yield compound (1) which is reacted further with an alkyl 4-chlorobenzene sulfonate, prepared from the corresponding alcohol and 4-chlorobenzenesulfonyl chloride by the procedure of Sondermann, *Liebigs Ann. Chem.*, 749: 183–197 (1971), to give intermediate (2). Removal of the phthalimido protecting group of (2) by heating in concentrated hydrochloric acid followed by a basic work-up yields compound (3) which is subsequently treated with methyl formate to give (4). Compound (5) is prepared by alkylation of either 2-methyl-benzoxazole (commercially available) or 2,3,3-(3H)-trimethylindolenine with an alkyl 4-chlorobenzene sulfonate. Compound (5) is then reacted with N,N-diphenylformamidine (commercially available) by a method analogous to that described in U.S. Pat. No. 2,647,054 to give (6). Intermediates (4) and (6) may then be coupled together by stirring in alcohol in the presence of a base (sodium acetate or triethylamine) to produce (7). Deprotection of (7) by the procedure of Dhawan et al., *Orgn. Prep. and Proc. Int.*, 7 (2): 85–88 (1975), gives amino derivatized cyanine (8).

The amino cyanines (8) can be directly attached to therapeutic agents containing suitable functionalities (e.g., CO, COOH) to produce conjugates useful for site-specific drug delivery. In addition, the amino cyanines (8) are very versatile intermediates for the preparation of a wide range of other cyanine derivatives capable of being conjugated to other bio-affecting moieties. Also, compound (8) is an ideal molecule for reaction with a large number of homo- and hetero-bifunctional spacer moieties, to provide separation between the lipophilic cyanine moiety and the bio-affecting substance linked thereto.

The amine substituent on the resultant cyanine derivative may be converted to other functionalities in a straight forward manner using well known reaction schemes. For example, conversion to isothiocyanate functional groups may be achieved by treatment with thiophosgene according to the procedure of de Costa et al., *J. of Lab. Compds. and Radiopharm.*, 27 (9): 1015 (1989).

Reaction of the amine group with 1,4-terephthalic acid di-N-hydroxysuccinimide ester provides a succinimidyl functional group joined to the cyanine head group by an OOC-aryl-CONH-alkyl spacer moiety. The resultant compound can be isolated and purified as a stable crystalline solid.

Simple acylation of the substituent amino group with p-nitrophenyl iodoacetate (commercially available) in dimethylformamide provides a reactive iodo-substituent coupled to the cyanine head group by an alkyl-CONH-alkyl spacer moiety.

Treatment of the amine group with N-hydroxysuccinimidyl-3-(2-pyridyldithio)propionate (commercially available) provides a compound having a pyridyldithio functional group and an alkyl-CONH-alkyl spacer moiety.

Treatment of the amine group with γ-thiobutyrolactone provides a compound having a sulfhydryl functional group and an alkyl-OCNH-alkyl spacer moiety. Similarly, treatment of the amine group with γ-butyrolactone provides a compound having a hydroxyl functional group and an alkyl-CONH-alkyl spacer moiety.

2. Protein/Peptide Lipophilic Cyanine Conjugates

A lipophilic cyanine precursor, prepared as generally described above, may be linked to a protein or peptide via a number of different synthetic routes, to yield compounds of formula II.

Coupling of proteins or peptides to lipophilic linker derivatives, such as those described above, may be through amine groups present on the proteins or peptides (i.e., terminal α-amino groups or amino groups of lysine). Alternatively, the carboxyl group or thiol group (where cysteine residues are present) may be used to couple proteins or peptides to appropriate cyanine precursors. Suitable conditions for carrying out such coupling reactions are known to those skilled in the art.

One approach for conjugation of a lipophilic cyanine precursor to an α-amino group of a polypeptide is via a modification of the procedure of Wetzel et al., *Bioconjugate Chem.*, 1, 114 (1990). This involves acylation of the polypeptide with iodoacetic anhydride (commercially available) at pH 6 to form an iodoacetamide derivative, which is then reacted with a sulfhydryl-derivatized lipophilic cyanine compound, prepared as described above, to form a conjugate via thioether bond formation which has good stability.

Conjugation by way of the ε-aliphatic amino group of lysine is best performed above pH 8.5, at which only a limited fraction of amines are, by equilibrium, unprotonated and reactive. This amino group should have high reactivity for several of the amine-reactive lipophilic linker compounds described above. For example, isothiocyanate derivatized linker compounds exhibit high stability in aqueous conditions and can react with lysine side chains to form conjugates linked via a thiourea bond.

The above-described N-hydroxy-succinimidyl ester derivatized linker compound is a particularly good reagent for reaction with lysine, since the amide conjugates thus formed are very stable. This reaction is preferably performed under anhydrous conditions in organic solvents, such as dimethylformamide, since hydrolysis of this particular derivative under aqueous conditions is a competing side reaction. A reaction whereby an N-hydroxy-succinimidyl ester derivatized linker of formula III, above, is conjugated to the amino group of the lysine residue at position 3 of the undecapeptide, substance P, is described in detail hereinbelow.

Carboxylic acid groups present in the side chains of glutamic and aspartic acid residues, as well as on the C-terminal amino acid residue of peptides or proteins, are possible sites for selective conjugation using the above-described amine derivatized lipophilic cyanine compounds. This reaction may be performed by using either a water soluble carbodiimide, such as 1-ethyl-3-dimethylaminopropylcarbodiimide (commercially available), according to a modification of the procedure of Hoare and Koshland, *J. Biol. Chem.*, 242: 2447–2453 (1967), or by using Woodward's Reagent K, 2-ethyl-5-phenyl-isoxazolium-3-sulfonate (commercially available), according to a modification of the procedure described in *J. Biol. Chem.*, 249: 5452 (1974), as the active coupling agent. The resulting conjugate is linked via a stable amide bond.

Attachment of the functionalized derivatives to reactive groups on a peptide or protein essential for biological activity is to be avoided, since an inactive conjugate will usually result. This problem may be overcome, however, if the peptide or protein can be released from the lipophilic cyanine derivative, via a cleavable spacer moiety.

Due to the lipophilicity of the compounds described above, some of them are poorly soluble in typical aqueous buffer systems. Conjugation reactions requiring aqueous conditions to maintain drug solubility or active conformation will typically have to be performed in an organic solvent-modified aqueous solvent. Solvents such as dimethylformamide, dimethylsulfoxide, acetonitrile and alcohols are miscible with water and may be useful to solubilize the lipophilic cyanine derivative and allow the desired conjugation to occur.

The compounds of the invention may be purified by various standard purification techniques making use of the size, charge or lipophilicity of the particular compound formed. A purification method which is particularly useful for therapeutic agents comprising peptides is that of Bohlen et al., *Int. J. Rept. Prot. Research*, 16: 306–10 (1980).

3. Biotinylated Lipophilic Cyanines

The biotinylated lipophilic cyanine compounds of the invention preferably are of the formula:

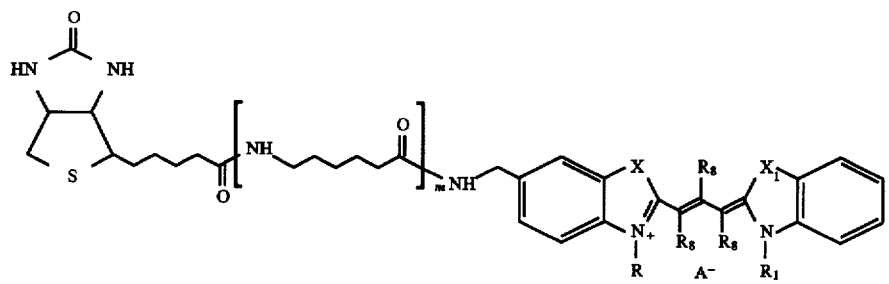

(IV)

wherein R, $R_1$ and $R_8$ are as previously defined and m is 0-6. Such biotinylated derivatives can be prepared via the reaction of biotin or a biotin derivative with a functionalized lipophilic cyanine compound of formula III, above. The biotin derivative used in this reaction preferably is of the formula:

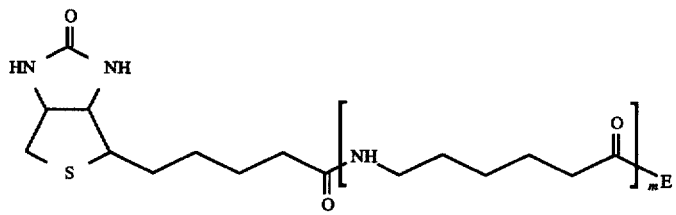

(V)

wherein E represents the residue of a compound having a labile group capable of substitution by said reactive functionality, W, and m=0, 1 or 2.

For example, amino functionalized cyanine derivatives (8) of the type prepared according to Reaction Scheme 1, can be reacted according to the procedure of Hofmann, Finn and Kiso, *J. Am. Chem. Soc.*, 100: 3585 (1987), with the commercially available amine reactive biotin derivatives, (+)-biotin 4-nitrophenyl ester, N-hydroxysuccinimidyl 6-(biotinamido)hexanoate and 6((6((biotinoyl)-amino) hexanoyl)amino) hexanoic acid N-hydroxysuccinimidyl ester, to form biotin-lipophilic cyanine conjugates of formula IV above, wherein m=0, 1 and 2, respectively. These conjugates differ with respect to the length of the spacer arm between the biotin moiety and the lipid binding moiety of the conjugate. The effect of such a spacer arm may be important depending on the intended application of the biotinylated compound. A longer spacer arm has been shown to have a beneficial effect on the ability of the biotin conjugate to bind to the "deep" binding site of biotin in avidin.

A variety of other biotin derivatives with reactive functional groups, such as maleimido, α-iodoacetamido, hydrazino and amino are commercially available (Molecular Probes, Eugene, Oreg., Handbook of Fluorescent Probes and Research Reagents, 1989–91) and could be used to couple with various of the above-described functionalized lipophilic linker compounds. Suitable reaction schemes will be apparent to those skilled in the art.

Additionally, a variety of different types of spacer moieties could be incorporated between the cyanine and biotin moieties via suitable functionalities on both precursors. Reaction schemes for the incorporation of such spacers are known to those skilled in the art.

4. Radioisotopically-Substituted Lipophilic Cyanines

Synthesis of a lipophilic tributyltin intermediate, useful for the preparation of radiohalogenated cyanine derivatives, which can be advantageously used in the methods of the present invention, is shown in Reaction Scheme 2, and is also described in detail in the examples below.

According to Reaction Scheme 2, 5-iodo-2,3,3-trimethyl-(3H)-indolenine (9), prepared from iodoaniline (commercially available), using procedures described by Blaikie et al., *J. Chem. Soc.*, 313, (1924) and Moreau et al., *Eur. J. Med. Chem. Chim. Ther.*, 9, (3): 274–280 (1974), is alkylated with an alkyl-4-chlorobenzene sulfonate (prepared as described previously) to provide (10). Treatment of (10) with N,N-diphenylformamidine in acetic anhydride then furnishes the vinyl intermediate (11). The intermediates (11) and (5) (the latter prepared as described previously) are then linked together by stirring in ethanol in the presence of sodium acetate. Quenching of this reaction mixture with silver acetate followed by sodium chloride gives iodocyanine (12).

Compound (13) can then be prepared from (12) by the procedure of H. Azizian et al., *J. Organomet. Chem.*, 215: 49–58 (1981), which involves heating (12) with bis-(tri-n-butyltin) in the presence of a catalyst, tetrakis-(triphenylphosphine) palladium (0). The tributylstannyl derivative (13) can then be readily radiohalogenated under mild conditions by, for example, a modification of the procedure of Wilbur et al., *J. Nuc. Med.*, 30: 216–226 (1989). Introduction of radiohalogens into (12) may also be achieved by solid phase exchange using variations on the procedure of Weiss et al., *J. Labelled Cmpds. & Radiopharmaceuticals*, XXVI: 109–10 (1989).

An alternative lipophilic cyanine derivative which may be used for the introduction of radiohalogens is an analogue of (13) in which the —Sn(Bu)$_3$ group is replaced by —HgX, X representing halogen. Of course, the ring position of the halogen substituent in compound (12) may be varied by appropriate selection of starting materials. For example, 6-iodo-2-methyl benzothiazole, prepared according to the procedure of Bassignana et al., *Spectrochemica Acta.*, 19 (11), 1885 (1963), may be used to provide the corresponding 6-iodo derivative.

5. Cleavable Colchicine-Lipophilic Cyanine Conjugates

Colchicine-cyanine conjugates with an acid cleavable linkage may be prepared by selecting a suitably functionalized active colchicine derivative (such as described by Brossi, *J. Med. Chem.*, 33: 2311, 2319 (1990)) and attaching it to a suitably functionalized lipophilic cyanine derivative via linkages such as cis-aconityl, acetal, orthoester, ester, ketal, anhydride or hydrazone.

Coupling via a cis-aconityl linkage may be achieved using the procedure described by Shen et al., *Biochem, Biophys. Res. Commun.*, 102, 3: 1048–1054 (1981). This procedure involves coupling a free amino derivative of the drug (e.g., desacetyl colchicine) and an amino form of the lipophilic cyanine with cis-aconityl anhydride (commercially available).

Coupling via an acetal, orthoester or ketal linkage may be achieved using modifications of the procedures described by Srinivasachar et al., *Biochemistry*, 28, 2501–2509 (1989) with appropriately functionalized colchicine and cyanine derivatives.

Coupling via a hydrazone linkage may be performed using modifications of the procedure described by Laguzza et al., *J. Med. Chem.*, 32: 548–555 (1989). This procedure involves coupling an aldehyde form of the drug with a hydrazide form of the lipophilic cyanine.

Synthesis of a cleavable colchicine-cyanine conjugate in accordance with the present invention is shown in Reaction Scheme 3, and is described in greater detail in the examples below.

According to Scheme 3, the amino functionalized cyanine (8) is coupled with the monomethyl ester of glutaric acid (commercially available) to furnish the methyl ester derivative (14) which, upon treatment with hydrazine in methanol, provides the hydrazino derivative (15).

The colchicine moiety is prepared by reacting deacetyl colchicine (commercially available) with glutaric anhydride to form an acid intermediate which is then activated in situ by the addition of carbonylidiimidazole to form an acyl imidazole which, upon reduction with tetrabutyl ammonium borohydride, provides alcohol (17). Oxidation of (17) with pyridinium chlorochromate produces 7-N-(5-oxopentanoyl) deacetyl colchicine (18) which is then coupled with the hydrazino derivative (15) to furnish conjugate (19) in which the colchicine and cyanine moieties are coupled via an acid cleavable acyl hydrazone bond. The 7-N-(5-oxopentanoly) deacetyl colchicine produced as an intermediate in Scheme 3 is a novel compound constituting part of the present invention. If desired, a methylthio, or other chalcogen-containing group, may be substituted for the methoxy group at the 10 position of the colchicine nucleus.

Additionally, the more potent 7-N-(5-oxopentanoyl) deacetyl thiocolchicine analogue can be made from deacetylthiocolchicine (prepared as described by Shian et al., J. Pharma. Sci., 64, 646–648 (1975)) using the same reaction sequence shown in Scheme 3 for the preparation of aldehyde (18). This derivative of thiocolchicine can also be attached to the hydrazino derivative (15) using the same coupling conditions to provide an acid cleavable conjugate.

The kinetics of release of the colchicine analogue from the conjugate can also be varied by modifying the type of hydrazone bond between the colchicine and cyanine moieties. For example, antibody-drug conjugates coupled via a sulfonylphenyl hydrazone and phenyl hydrazone bond have been described by Mueller et al., *Bioconjugate Chem.*, 1:

325–330 (1990) to provide slower release kinetics than the corresponding acyl hydrazone derivatives.

6. Heparin-Lipophilic Cyanine Conjugates

A synthetic route for a heparin-cyanine conjugate, coupled via a stable carbamate bond and which is useful in the present invention is shown in Reaction Scheme 4, and described in greater detail in the examples below.

According to Scheme 4, the amino functionalized cyanine (8) is converted into the highly reactive isocyanate derivative (20) upon treatment with triphosgene according to the procedure of Eckert et al., *Angew Chem. Int. Ed. Engl.*, 26 (9): 894–95 (1987). The isocyanate derivative (20) is not isolated or purified further and is then reacted immediately with sodium heparin in a mixed solvent of dimethylformamide/formamide according to a modification of the procedure of Dong, "Heparinized Segmented Polyurethane Urea Surfaces with Hydrophilic Spacer Groups", Dissertation, University of Utah, 1990 to provide heparin-lipophilic cyanine conjugates (21) in which heparin is covalently attached to the cyanine through its hydroxyl group via carbamate bond formation (or through amino groups via urea bond formation). A carbon spacer arm may also be incorporated between the heparin and cyanine moieties using the commercially available reagent, N-Boc-6-aminohexanoic acid N-hydroxysuccinimide ester, via reactions known to those skilled in the art.

The number of cyanine groups per heparin molecule can of course be varied by controlling the stoichiometry of reagents in the reaction since heparin has a number of free hydroxyl groups available. Heparin-lipophilic cyanine conjugates may be purified from free heparin, if necessary, by hydrophobic interaction chromatography.

Alternatively, a heparin-cyanine conjugate may be prepared using a modification of the procedure described by Kin et al., *Nonthrombogenic Bioactive Surface Annals*, New York Academy of Sciences, p 116–130. This procedure involves coupling the carboxylic acid groups on heparin with an amino functionalized cyanine using a carbodiimide reagent. It has been determined by Ebert et al., *Biomaterials: Interfacial Phenomenon and Application*, Adv. Chem. Ser. 99, American Chem. Soc., Washington, D.C. (1982), that up to 20% of the carboxylic groups on heparin can be derivatized with no loss in bioactivity.

7. Radiometal Complex—Lipophilic Cyanine Conjugates

A synthetic route for a radiometal complex-lipophilic cyanine conjugate, where the metal is one selected from the group consisting of rhenium, indium, copper or palladium, is shown in Reaction Scheme 5. According to Scheme 5, the bifunctional chelating agent (22), prepared as described by Baidoo and Lever, *Tetrahedron Lett.*, 31, 40, 5701–5704 (1990) is reacted with an amino functionalized cyanine (8) to furnish derivative (23). Compound (23) is then reacted with a solution of the metal in an appropriate oxidation state to furnish the metal complex (24). Scheme 5 illustrates the structure of the neutral metal complex obtained when the metal used is rhenium. The exact structure and charge of the complex of course depends on the metal used and the exact structure of the bifunctional chelant chosen.

A route to prepare a radiometal complex-lipophilic cyanine conjugate where the metal is selected from the rare earth metals, is shown in Reaction Scheme 6.

Bifunctionalized polyaminocarboxylate chelants of structure (25) can be prepared according to procedures described in European Patent Publication Number 0353450 A1.

According to Scheme 6, chelant (25) is reacted with an amino functionalized cyanine (8) at pH 9–9.5 to furnish compound (26) in which the chelant and cyanine moieties are coupled via a stable thiourea bond. Compound (26) can then be reacted with a solution of the radiometal salt in a suitable buffer system according to procedures also described in the above-mentioned European Patent Publication to furnish the final radiometal complex-cyanine conjugate (27).

M(PA-DOTA), which is used in the illustration of Scheme 6, refers to the radiometal complex comprising the polyamino-carboxylate chelator and a portion of the spacer moiety (—(CH$_2$)$_2$—C$_6$H$_4$—NH—) in intermediate (26) shown in Scheme 6. The 3-dimensional structure of the radiometal complex moiety of compound 27 is expected to be similar to that described by Spinlet et al., *Inorgn. Chem.*, 23: 4278–4283 (1984).

Other types of bifunctionalized polyaminocarboxylate chelants are known and could be coupled to functionalized cyanines via other reactions known to those skilled in the art. See, for example, Sundberge et al., *J. Med. Chem.*, 17: 1304 (1974).

Other tetradentate chelants containing nitrogen and sulfur-containing tetradentate chelants are known and can be coupled to a suitably functionalized cyanine via reactions known to those skilled in the art. See, for example, Ras et al., *J. Am. Chem. Soc.*, 112: 5798–5804 (1980).

IV. BINDING COMPOUNDS OF THE INVENTION TO BIO-COMPATIBLE PARTICLES

The number of linear carbons in the hydrocarbon tail(s) substituted on the compounds of the invention is an important factor in achieving the desired degree of stable association between the compounds and the surface membranes of bio-particles. To achieve stable binding of compounds having a single hydrocarbon tail, e.g., acridine derivatives, the linear number of carbons should be 23 or greater. Experience with cyanine derivatives prepared in accordance with the present invention, indicates that in compounds having two or more hydrocarbon tails, one of the tails should have a linear length of at least 12 carbons, with the sum of the linear carbon atoms in the hydrocarbon tails being at least 23. Depending on the structure of the compound, ordinarily leakage or transfer from one cell to another will not occur. In general, the longer the hydrocarbon tail, the higher the lipophilicity. Hydrocarbon tails having more than 30 linear carbon atoms, however, may pose a problem because the bio-affecting moiety and the reactant used to provide the hydrocarbon tail may not be soluble in the same solvent, making the chemistry of joining the hydrocarbon tail to the bio-affecting moiety quite difficult. Thus, there may be a practical limitation on the lengths of the hydrocarbon tail(s), depending on the chemical nature of the linking moiety to which the tail(s) is (are) to be bound.

Structural variations in the linking moiety to which the "tails" are attached also has considerable influence on the degree of membrane binding stability. Positively charged linking moieties, for example, cyanine, styrylpyridine, xanthene, phenoxazine, phenothiazine or diphenylhexatriene dyes and derivatives thereof, may contribute to incorporation and retention of the compound in negatively charged membranes. Neutral or negatively charged linking moieties may also be useful in achieving controlled release from bio-membranes.

Stable association between the linking moiety, the hydrocarbon tail(s) and the spacer moiety, or bio-affecting moiety, as the case may be, is essential to achieving site-selective retention of the therapeutically active substance for the requisite time and in the requisite amount to realize the therapeutic benefit which this invention provides.

The linking moiety (L) should be selected so as to impart to the compounds of the invention the level of stability required so that the compounds will be present at the selected site of delivery for a time, and in an amount sufficient to achieve the desired therapeutic benefit. To this end, the linking moiety in compounds of formula I, above, should provide stable association between the bio-affecting moiety (B) and at least one of R and $R_1$ when n=0, and between the spacer moiety ($R_2$) and at least one of R and $R_1$ when n=1. Compounds having the requisite associative stability imparted by the linking group can be determined on the basis of time of retention, in the case of direct administration of a therapeutically active, lipophilic conjugate, or time of circulation, in the case of delivery of the conjugate to the disease site via a carrier. That is to say, the time of retention or time of circulation of the therapeutically active, lipophilic conjugates of the invention must be greater than the time of retention or time of circulation of the therapeutically active component in unconjugated form.

Although increased time of retention or time of circulation are important factors in achieving the therapeutic benefit afforded by this invention, another equally important factor, which also depends on the associative stability of the compounds of the invention, is the presence or accumulation of the compound at the disease site in an amount sufficient to provide the desired therapeutic benefit.

Determination of time of retention or time of circulation may be carried out in various ways known to those skilled in the art, as exemplified hereinbelow in Examples 9, 10 and 12, among others. Determination of the amount of therapeutically active, lipophilic conjugate of the invention that is required to produce the desired effect, as is often the case with therapeutic agents, is not subject to a specific procedure. This is necessarily so, due to the diversity of therapeutically active substances that may be used in the practice of this invention, the numerous disease states that are treatable therewith and the variability of the condition of the patient receiving therapy. Accordingly, the response of a patient receiving therapy in accordance with this invention will have to be monitored periodically to determine that the amount of therapeutically active substance present or accumulated at the disease site is sufficient to produce the desired therapeutic benefit.

The compounds of the invention can be designed to bind to the outer membrane of viable cells or other bio-compatible particles without initial detrimental effect on viability, or they may be designed to exert an immediate or delayed cytostatic or cytotoxic effect. To determine the extent of cytotoxicity due to a cytotoxic bioaffecting moiety, for example, cells are exposed to a compound of the invention at a variety of concentrations, including zero concentration as well as to a compound that is not conjugated to a cytotoxic agent. The cells are then exposed to trypan blue or propidium iodide (F. Celada et al., Proc. Natl. Acad. Sci., 57: 630 (1967)). These dyes are normally excluded by a living cell and only permeate the membrane of a dead cell. After the appropriate incubation time, the cells are examined with a microscope or by flow cytometer and the percentage of stained cells (percent dead) is determined.

Binding of the compounds of the invention to carrier cells should also exert no appreciable detrimental effect on cell functions which are important to their ability to perform as carriers for target delivery. For example, it may be important for the carrier cell to divide in order for it to perform in a given application. On the other hand, the compound used may alter some function having no effect on the division potential or other performance requirement of the cell for the contemplated application. Hence, such compounds may be considered to be without appreciable detrimental effect on cell function for purpose of its use in this invention. Procedures for determining the effect on cell functions of potential importance to the practice of this invention, produced by compounds of the invention are described in U.S. Pat. No. 4,859,584, in Slezak and Horan, Blood, 74: 2172–77 (1989) and in J. Immunol. Meth., 117: 205–14 (1989).

Two criteria must be met in selecting a cell binding medium in order to reproducibly bind compounds of the invention to the plasma membrane of target or carrier cells without producing a detrimental effect on desired cell function. The cell binding medium must (i) be isotonic for the bio-compatible particle to which the compound is to be bound and at an iso-osmotic concentration (approximately 260–340 mOs moles for mammalian cells) so as to not cause shrinkage or swelling and possible damage to the cells and (ii) allow for the compounds of the invention to be solubilized in such a manner that they are available at consistent concentrations to incorporate into the plasma membrane of the cells. Solubility time course experiments (U.S. Pat. No. 4,783,401 and M. Melnicoff et al., J. Leuk. Biol., 43: 387–397 (1988)) have shown that compounds which are only partially water-soluble and which serve to stably bind to the plasma membrane tend either to form micelles or aggregates which can be precipitated when solubilized in ionic solutions (e.g., phosphate buffered saline, culture medium, etc.), resulting in reduced incorporation of the compound into the plasma membrane or undesirably inconsistent incorporation.

With radioisotopic compounds similar experimental procedures are applicable and compound stability can be determined by using beta- or gamma-counters. In all cases, the amount of the compound of the invention in the supernatant of said iso-osmotic solution at each time point is compared to a sample of such compound using ethanol as a solvent, which, although not suitable for labeling cells, serves to allow for the maximum compound solubility (total).

To determine the appropriate concentration of a compound of the invention for binding to the plasma membrane of cells, several factors should be considered, including the intended effect to be produced by the compound and the cell type to which the compound is bound. Generally, the primary goal is to incorporate as-much of the therapeutic agent into the cell membrane as possible. This can be achieved by direct delivery of the therapeutic compound to the disease site or by binding the therapeutic compound to cells ex vivo and reintroducing the modified cells in vivo. By maximizing the incorporation of therapeutic agent into the plasma membrane of the cell, relatively lower dosages could be administered, or fewer carrier cells would be required to reach the desired location to exert the desired effect. In the case of delivery of therapeutic agents via cells, the amount of compound incorporated into the cells should increase only to such a level that no negative alterations are noted in the carrier cell with respect to viability or capability of the cells to migrate to the desired location.

Compounds of this invention are applied to carrier cells or other bio-compatible particles in the absence of serum and other lipid-containing materials. Cells are removed from the body or taken from culture and washed to be free of serum. They are suspended to form a composition including the iso-osmotic regulating agent, generally not in ionic solutions, and an appropriate concentration of a compound of the invention ($10^{-5}$ to $10^{-7}$M). Binding of the compound to the cells is generally complete within ten minutes and the binding reaction may be stopped with the addition of autologous or heterologous serum. The cells are then washed in serum-containing media (5–10% v/v) and placed into culture or injected into the recipient depending on the application.

The procedure for cell binding of compounds of the type described herein is described in further detail in the aforementioned U.S. Pat. No. 4,783,401, the entire disclosure of which is incorporated by reference in the present specification as though written out herein in full.

Another cell binding technique involves suspension of the compounds of the invention in saline to allow for micelle formation. The cells are then placed into the resulting suspension and the phagocytic cells (for example, monocytes, macrophages and neutrophils) will preferentially become labeled. In this way, it is possible to direct compounds of the invention selectively to the phagocytic cells. M. Melnicoff et al., J. Leukocyte Biol., 43: 387–97 (1988).

Representative applications of the compounds, compositions and methods of the invention will now be described with reference to particular pharmacotherapies.

V. METHODS OF USING COMPOUNDS OF THE INVENTION

A. General Therapeutic Methods

1. Isotopic Therapeutic Applications

Because of their ability to be incorporated into the lipid component of a lipid-containing bio-compatible particle and to chelate ions which are radioactive and emit high linear energy transfer (LET) radiation, the compounds of the invention can be used to deliver radiation therapy to the site of disease. Cells are labeled with a compound of the invention by first forming a stable complex of a chelating compound of the invention and an appropriate radioactive ion (e.g., $^{67}$Cu, $^{90}$Y, $^{186}$Re, alpha emitters), isolating the complex and following the general cell binding procedure described above.

Tumor infiltrating lymphocytes (TIL) may be isolated from a primary lesion, expanded in IL-2, bound to a radiotherapeutic substance as described above and injected intraveneously. The labeled cells track to the site of metastatic disease, and emit radiation which kills the metastatic tumor cells, thereby increasing the therapeutic effectiveness of the TILs, and perhaps decreasing the number of cells required to obtain disease regression. Similarly, other cell types which migrate to metastatic sites may be utilized for delivery of localized radiation therapy.

2. Cell Targeting by Binding Specific Proteins to Cell Membranes

In another embodiment, the compounds of the invention have incorporated therein proteinaceous substances, including proteins, glycoproteins, lipoproteins or peptides as the bio-affecting moiety. These compounds are bound to cells as described supra, whereupon the hydrocarbon chains of said compounds become embedded into the plasma membrane, thereby placing the protein onto the surface of a specific cell type.

The procedure described above may be used to bind monoclonal antibody to human fibrin to the surface of a carrier cell, e.g., red cell for delivery to the site of a fibrin clot.

A similar approach may be used for delivery of monoclonal antibody to human cell surface tumor antigens to a tumor site via a carrier cell, e.g., monocyte or lymphocyte. Tissue plasmihogen activator may be similarly delivered by application to the surface of a carrier cell (e.g., red cell).

The above-described therapies may, if desired, be used in combination. Thus, a monoclonal antibody which binds to human fibrin may be bound to the surface of a cell (e.g., red cell), which is then also bound with a fibrinolytic compound (e.g., tPA, Streptokinase, urokinase). The monoclonal antibody enables the carrier cell to bind to fibrin and after binding delivers a large number of therapeutic fibrinolytic compounds.

These therapeutically active proteins may be conjugated to a lipophilic chromophore in accordance with the general preparative procedures described above.

The above-described techniques may also be used to incorporate various other therapeutically active proteins or peptides into suitable bio-compatible particles, such as cells, viruses, liposomes or LDLs, thereby substantially prolonging the bioavailability of the proteinaceous substance in circulation.

The protein-bound bio-compatible particles may also be isotopically labeled, as described above, using a radioimaging compound or a magnetic resonance imaging compounds. The resultant bioparticle may be injected into a patient whereby the cell migrates to the disease site, which can be imaged using standard gamma scintigraphy or nuclear imaging to assess the effect of the therapeutic agent.

3. Protein Coupling to Cells for Vaccine

In another application of this invention, an immunogen, to which protective antibody production is desired, which may be a protein, glycoprotein, lipoprotein or peptide, is used as the bio-affecting moiety, optionally including a linking group, for binding to the surface of a cell (e.g., red cell, monocyte). The cell thus modified is then injected in the presence or absence of adjuvant. The timing interval between injections will depend upon the nature of the immunogen but generally $10^6$ cells may be injected each time at intervals of not less than two weeks.

Antibody levels to the antigen are monitored with standard Elisa procedure. Cellular immune levels can be measured by determining proliferative or cytotoxic responses to immunizing cells.

4. Alterations in Migration Patterns By Modifying Cell Surface

In another application of this technology, sialic acids or glycosaminoglycans can be bound to the plasma membrane of a cell using the compounds of the invention. The specific compound is placed into iso-osmotic media as described hereinabove. Red cells, for example, are placed into the solution, resulting in binding of the compound to the plasma membrane. The reaction is stopped with the addition of serum, after which the cells are washed in saline containing medium and are ready for injection.

Red cells traverse the circulation and, as immature cells, they have a large amount of sialic acid on their surface. As the red cell ages, the amount of sialic acid per cell is reduced making it possible for the splenic and liver macrophages to recognize red cell membrane antigens, thereby removing them from circulation. By appropriately increasing the amount of sialic acid incorporated into the membrane of a red cell, it may increase the life of the red cell in circulation.

The ability to increase the lifetime of a red cell may be advantageous for a transplant patient or for a patient with anemia. When bone marrow transplant patients receive the transplant, it is several weeks before they are capable of making their own red blood cells. By using this technology to prolong the lifetime of their own red cells, patients can be given several marrow transplants, if need be, without having bouts of anemia.

In the case of the anemic individual, the anemia may result from a decrease in the lifetime of the red cell or a decrease in the rate of production of red cells. In either case, increasing the lifetime of the red cell will reduce the anemia.

5. Delivery of Photodynamic Compounds for Therapeutic Action

Photodynamic therapy for the cure of cancer is an area of intense research(Proceedings of SPIE-The International Society for Optical Engineering; Volume 847, "New Directions in Photodynamic Therapy", Douglas C. Neckers, Editor; (October 1987)). Many of these compounds are of the phthalocyanine class or the hematoporphrin class. All absorb light in the 600–800 nm region and produce excited state oxygen in the process.

Using the methodology of this invention, a lipophilic derivative of the compound is made and then dissolved in the iso-osmotic solution. Tumor selective cells (e.g., TIL) are labeled with these compounds and the cells are injected into the patients. The tumor selective cells then migrate to the site of the micrometastasis. Within 48 hours, the patient is exposed to high intensity light in the region where the photodynamic molecule absorbs and the excited state oxygen produced will kill the tumor cells. Furthermore, the carrier cells will be killed and this should generate an inflammation whereby more immune cells converge to remove the dead cells, increasing the toxicity to tumors. In this method of delivery of photodynamic action, the carrier cells are responsible for more selective accumulation of therapeutic agent at the tumor site. In some cases, direct application of compounds of the invention to tumor deposits within a body cavity (e.g. pleural cavity) may assist in retention at the site, enabling more effective intracavitary irradiation treatment at the time of surgery.

B. Treatment of Specific Diseases or Pathological Conditions by Direct Delivery of Therapeutically Active Substances

1. Post-Angioplasty Reocclusion and Restenosis

It has been demonstrated experimentally that compounds of the invention can be retained at local vascular sites as well as on artificial surfaces, even in the presence of continuous blood flow (See Examples 8 and 12, below). Additionally, it has been shown in vitro and in vivo that biological activity can be retained in a compound of the invention comprising a therapeutically active substance (See Examples 4, 13 and 15, below).

Studies on animal model systems have revealed that the primary cellular events of proliferation and migration that lead to post-angioplasty restenosis occur within approximately 7–21 days after angioplasty. Therefore, an antiproliferative drug must be retained by the smooth muscle cells in a repaired artery for up to 7–10 days after angioplasty to prevent these events. Compounds of the invention, comprising suitable anti-proliferative agents, may be delivered to the damaged vessel wall during angioplasty, and the antiproliferative agent conjugated to the compound may be retained by the damaged cells. Thus, higher doses of antiproliferative drugs can be given directly to the affected cells and can be retained at the affected site longer through the use of compounds of the invention than through systemic drug delivery. For example, direct deposit of antiproliferatives via drug delivery catheters in angioplasty will permit the drug to bind to the membranes of cells at the site of the angioplasty procedure, while any unbound drug may be flushed from the artery during the procedure. The catheter will be removed and the drug bound to resting cells will remain in the outer membrane or traverse interstitial spaces to arrive at deeper cell layers. If those cells go into an active or growth state, the compound of the invention will move into the cells as membrane components traffic inward. Once inside cells they can exert their antiproliferative action. Thus, compounds of the invention comprising suitable antiproliferatives, may be delivered primarily to the disease site and the amount of drug processed by the liver or kidney at any one time is minimized, reducing the opportunity for serious adverse reactions.

In a preferred embodiment, compounds of the invention useful for treatment of post-angioplasty restenosis comprise antiproliferative agents, such as heparin, hirudin, colchicine, vinca alkaloids, taxol and derivatives thereof. Application of heparin to smooth muscle cells in culture or by administration to animals after arterial injury results in decreased growth and reduced myointimal thickening and cell proliferation. Compounds of the invention comprising heparin preferably will be constructed such that they remain on the external membrane of cells of the inner arterial wall, by hydrophobic interaction with one or more cell wall components, rather than being taken up into the interior of those cells. In contrast, antiproliferative agents such as colchicine, which interfere with tubulin processes must be taken up by cells in order to exert their antiproliferative effect. In this instance it is preferable to synthesize compounds of the invention such that they are capable of becoming internalized within arterial cells of the inner wall more quickly. In a preferred embodiment, colchicine comprises the bio-affecting moiety of a compound of the invention as an acid-clearable conjugant. The cotchicine is inactive in its conjugated form. However, uptake of the compound into intracellular acid vesicles causes the agent to be released from the compound, thereby activating it. Thus, active colchicine is delivered to its site of activity within the cell, and is capable of inhibiting tubulin processes therein, thus inhibiting cell division.

Particularly preferred for use in the present invention is an acid-cleavable colchicine-containing compound of the formula:

Another useful colchicine-containing compound has the formula:

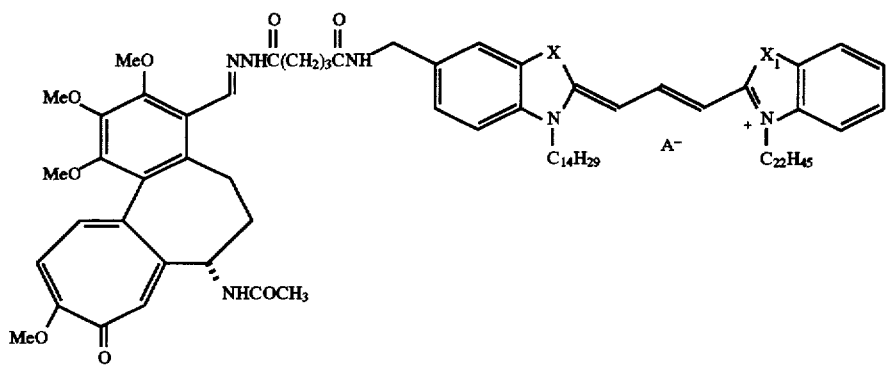

Other antiproliferative agents contemplated for use in the practice of the present invention include: angiotensin converting enzyme (ACE) inhibitors, angiopeptin, cyclosporin A, calcium channel blockers, goat-antirabbit platelet derived growth factor antibody, Terbinafine and Trapidil, interferon-gamma and polyanions for binding of cationic growth factors.

2. Rheumatoid Arthritis

Therapeutic compounds of the invention are particularly well-suited for treatment of rheumatoid arthritis. They provide a means of performing chemo- or radiation synovectomy that enables the joint to retain a significant amount of therapeutic agent without significant systemic release to the lymph nodes, spleen or liver. A major advantage over all existing delivery systems is that compounds of the invention are delivered uniformly to the very tissue that requires treatment and are retained in those cells. For radiotherapeutic compounds of the invention, the radioactivity emitted from the compound initiates therapeutic action on cells of the synovial membrane. As described in greater detail in the examples below, essentially all compound in the body is found in the treated joint, and approximately 70% of the injected compound is retained there after six days. This localized and extended retention will decrease the dose of radioisotope needed for each procedure of radiation synovectomy, and will reduce the side effects caused by the systemic exposure to the radioisotope released from the joint using conventional therapies.

Radiotherapeutic compounds of the invention that are particularly preferred for radiation synovectomy may be synthesized to incorporate an appropriate radioisotope, as exemplified below. For example, a radiometal may be complexed with either (1) a nitrogen and sulphur-containing chelator or (2) a nitrogen and oxygen-containing chelator.

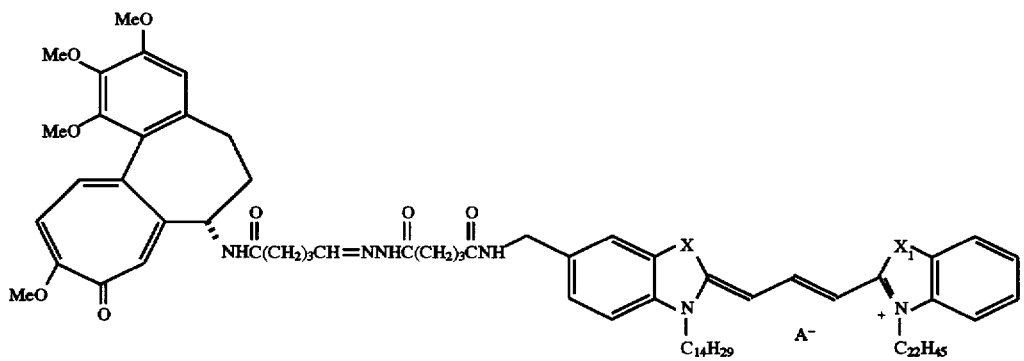

The radioisotope may be selected from the group consisting of radioactive halogen, copper, yttrium, rhodium, palladium, indium, iodine, samarium, gadolinium, holmium, erbium, ytterbium, lutetium, rhenium, gold, or a combination thereof.

A preferred compound for use in the present invention is a compound having the formula:

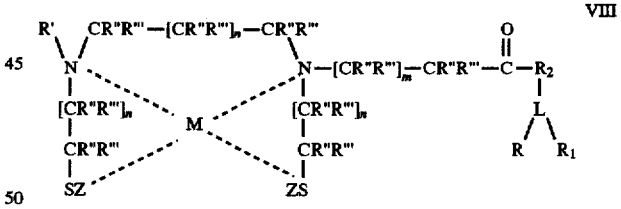

wherein L, R, $R_1$ and $R_2$ are as defined for Formula I above;

represents H or a metal coordination site;

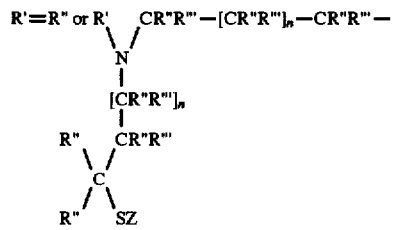

wherein each R' is independently a hydrogen atom or an alkyl group, preferably a lower alkyl group, or substituted lower alkyl wherein the substituent can be any ester, R" and R''' are independently a hydrogen atom or an alkyl group and m and n can each be zero or 1; and M represents a radiometal selected from the group consisting of rhenium, indium, copper and palladium.

In a preferred embodiment, the compound of formula VIII above has the formula:

IX

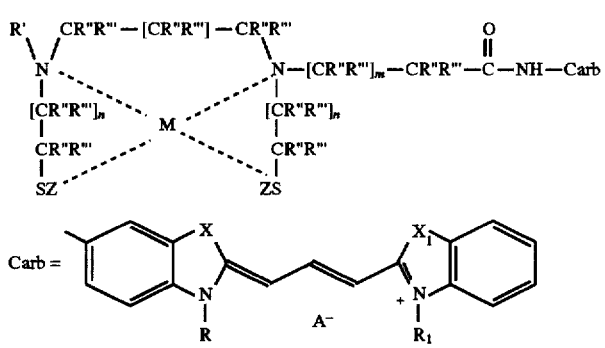

wherein R and $R_1$ are hydrocarbon substituents having from 1 about 30 carbon atoms; X and $X_1$ may be the same or different and represent O, S, C(CH$_3$)$_2$ or Se;

A represents a pharmaceutically acceptable anion;

Z represents H or a metal coordination site;

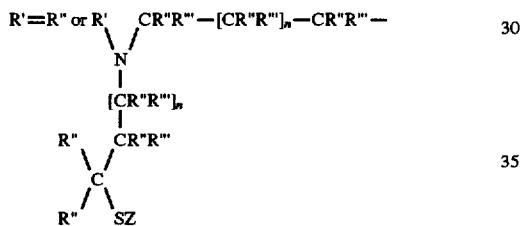

wherein each R' is independently a hydrogen atom or an alkyl group, preferably a lower alkyl group, or substituted lower alkyl wherein the substituent can be any ester, R" and R''' are independently a hydrogen atom or an alkyl group and m and n can each be zero or 1; and M represents a radiometal selected from the group consisting of rhenium, indium, copper and palladium.

Another particularly preferred compound for use in the present invention is a compound of the formula:

Another useful compound is of the formula:

X

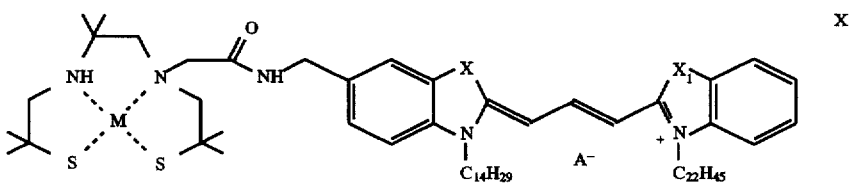

where M represents a radiotherapeutic substance such as rhenium, indium, copper or palladium.

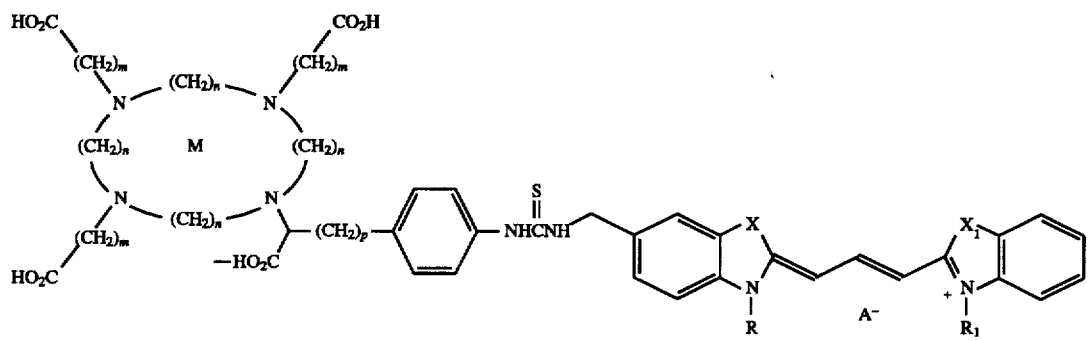

IX wherein R and $R_1$ are hydrocarbon substituents having from 1 to about 30 carbon atoms; X and $X_1$ may be the same or different and represent O, S, $C(C_3)_2$ or Se;

A represents a pharmaceutically acceptable anion;

M represents a radiotherapeutic substance selected from the group consisting of copper, technetium, rhodium, palladium, indium, samarium, gadolinium, holmium, erbium, ytterbium, lutetium, rhenium, yttrium, gold, erbium, holmium, or a combination thereof; n is 2, 3 or 4; m is 1 or 2; and p is 1 to 6.

3. Ovarian Cancer

Compounds of the invention comprising chemotherapeutic or radiotherapeutic agents will enable high concentrations of those agents to be delivered directly to the site of ovarian tumor cell proliferation. Additionally, the therapeutic agents will be retained for longer periods of time in the peritoneal cavity, thus retarding the dissemination of tumor cells. Moreover, this can be accomplished without the significant side effects accompanying administration of large concentrations of such agents via systemic delivery systems.

Compounds of the invention may be delivered intraperitoneally through a Tenckhoff catheter as a treatment after surgery, or by a second-look laparotomy, and as adjuvant therapy at the time of surgery.

Acid-cleavable colchicine-containing compounds of the invention, as described previously, will also be useful in antiproliferative treatment of ovarian tumor cells. As noted above, it is expected that such a molecule will remain on the outer membrane of a cell in a non-toxic form. However, when the compound is taken into the cell where the chemotherapeutic drug is cleaved from the remainder of the compound, the chemotherapeutic substance can exert its antiproliferative activity.

4. Psoriasis

Compounds of the invention comprising corticosteroids may be used to advantage in the treatment of psoriasis. They provide greater retention of the drug at the site of a psoriatic lesion, thus enhancing the efficacy of the drug in reducing the proliferation of keratinocytes and immune cells. Moreover, retention of the compounds of the invention at the site of the lesion will prevent the penetration of possibly toxic compounds into the circulatory system. This results in a clinical benefit in that, after a two-week series of applications, the therapy should not need to be terminated because of high serum concentrations of antiproliferative drug.

According to other applications of this invention, platelets or low density lipoproteins (LDL) may be tracked to the site of atherosclerotic plaque deposition for early detection of atherosclerosis. Platelets may be isolated from the individual's blood using standard gradient techniques, then labeled with indium or technetium, as optional diagnostic moieties, and reinjected intravenously. A suitable procedure for binding compound of the type described herein to platelets is provided in the aforementioned U.S. Pat. No. 4,762,701. Within the next 48 hours, the radioactive labeled platelets accumulate at the site of the plaque formation on arterial walls, where the gamma emission can be detected using a gamma camera.

Similarly, LDL may be purified by standard ultracentrifugation techniques and labeled with compounds of the invention, by virtue of their significant lipid content and the binding affinity of compounds of the invention for lipid regions of bio-compatible particles. These radiolabeled LDL will accumulate at sites of atherosclerotic plaque buildup after reinjection, allowing detection by nuclear imaging. Monocytes are also known to accumulate in atherosclerotic plaque, and therefore, may also be useful in detecting its formation; their only limitation is expected to be availability of suitable numbers of purified monocytes for radiolabeling.

Platelets are also known to accumulate at sites of thrombosis (e.g., coronary thromboses, deep vein thromboses, intravascular grafts) and at sites of acute rejection following organ transplantation. Therefore, autologous platelets isolated by standard methods and radiolabeled using compounds and methods of the invention will also allow non-invasive diagnosis of such disease processes when combined with pharmacotherapy.

Also, while it is possible to use chelators to bind to radioactive metal ions, it is also possible to make fluorescent or non-fluorescent compounds of the compounds of formula I, above, wherein radio-isotopic, e.g., radioactive iodine, carbon, nitrogen, sulphur, phsophorus or selenium, atoms are constituents of the molecule. Compounds emitting gamma rays of sufficient energy using radioisotopically labeled compounds of the invention may be detected using gamma scintigraphy. If the isotope is a low energy non-penetrating beta emitter, then the compound can be used in research applications using standard beta counting techniques.

The biotinylated lipophilic compounds of the invention can function as multi-purpose reagents. For example, such compounds may be used to cause typically non-adherent cells to adhere rapidly to a selected surface. This is important for analyses requiring immobilized cells, i.e., in monitoring of a single cell over time. If a cell population is labeled with a biotinylated compound of the invention and the resultant labeled cells are brought into contact with a surface to which streptavidin is bound, the cells will rapidly adhere to the surface. The cell analysis can immediately begin. The fluorescence associated with the biotinylated compound also provides a convenient means of visually monitoring the cell during the experiment.

In addition, it has previously been demonstrated that fluorescent cell labelling compounds can be used to monitor growing cells and measure the growth rate by dilution of fluorescence. (U.S. Pat. No. 4,859,584). This technique loses sensitivity after 5–8 doubling times (dependent on cell type), as the fluorescence of the labelling compound decreases to the level of autofluorescence. Amplification of fluorescence can be achieved by binding a fluorochrome-conjugated streptavidin to, e.g. a biotinylated cyanine, as described herein. By this method, labeled cells can be identified even after the chromophore fluorescence has decreased to the level of autofluorescence. If further sensitivity is required, a radio-labeled streptavidin can be bound to the biotinylated compound of the invention and autoradiography can be performed to identify the labeled cells.

Another application of the biotinylated compounds of the invention is in protein binding. For some large proteins, it might not be possible to link the protein to a cell through covalently binding the protein to a lipophilic compound of the invention, such as represented by formula III, above. In such cases, an alternative coupling mechanism is the avidin-biotin binding pair. For this purpose, target cells may be labeled with a biotinylated compound of the invention and the large protein would be conjugated to avidin or a suitable derivative of avidin, e.g., streptavidin. The biotinylated cells would then be exposed to the avidin-protein conjugate resulting in protein bound stably to cells.

C. Pharmaceutical Preparations

Pharmaceutical preparations comprising compounds of the invention may be conveniently formulated for administration with a compatible biological medium, such as salt-free isomotic solutions, or pharmaceutically acceptable liquid excipients. The latter include various inert oils, e.g., vegetable oils such as olive oil or peanut oil, or highly refined mineral oil. The concentration of active ingredient in the chosen medium will vary, depending on the nature of the compound and the disease or pathological condition being treated.

It is especially advantageous to formulate the pharmaceutical preparation in dosage unit form for ease of administration and uniformity of dosage. Dosage unit form as used herein refers to a physically discrete unit of the pharmaceutical preparation appropriate for the patient undergoing treatment. Each dosage unit should contain the quantity of active ingredient calculated to produce the desired therapeutic effect in association with the selected pharmaceutical carrier. Procedures for determining the appropriate dosage unit for inhibiting cell proliferation, or for treatment of other pathological conditions in a given class of patients are well known to those skilled in the art. In radiation synovectomy for example, doses of approximately 5 mCi of $^{90}$Y (half life 2.7 days, beta energy 2.2 MeV) or 300 mCi $^{165}$Dy (half life 2.3 hours, beta energy 1.3 MeV) administered in various colloidal forms have demonstrated clinical efficacy. P. Lee, J. Rheumatol., 9: 165–167 (1982); C. Sledge et al., Clin. Orthop., 182:37–40 (1984). Using standard dosimetry calculations, it is estimated that similar therapeutic effect would be obtained from an approximately 10 mCi dose of $^{186}$Re (half life 3.7 days, beta energy 0.98 MeV), which dose would be provided by injection of approximately 0.05 μmoles of a suitable compound (e.g., compound 23 of Reaction Scheme 5) prepared at a specific activity of 200 mCi/μmole. Other radiotherapeutic isotopes are also known in the art. W. Volkert et al., J. Nucl. Med., 32: 174–185 (1991). Other compounds of the invention are also anticipated to be useful in delivering efficacious doses of such agents.

In radiotherapeutic treatment of tumors, doses of 80 Gy have been suggested as sterilizing doses of radiotherapy for solid tumors when delivered via monoclonal antibodies. J. Humm, J. Nucl. Med, 27: 1490–1497 (1986). Binding to cell surface membranes and internalization are predicted to enhance the efficacy of such therapy. Humm, J. L., J. Nucl Med., 31: 75–83 (1990). A dose of 80 Gy would be provided by injection of approximately 0.8 nmoles of compound 23 prepared at a specific activity of 200 mCi/μmole. This and other compounds of the invention are also expected to have utility in the delivery of other radiotherapeutic isotopes known in the art. W. Volkert et al., supra. Like other types of anti-cancer radiopharmaceuticals, compounds of the invention may be delivered directly into tumor tissue, into body cavities containing disseminated tumor, or into blood vessels which supply the tumor, etc. C. Hoefnagel, Anti-Cancer Drugs, 2: 107–132 (1991).

In the treatment of post-angioplasty restenosis, to demonstrate that sufficient amounts of the compounds of the invention can be delivered to a pathophysiologic site, it can be noted that the 1 mg/day human therapeutic dose of colchicine administered by Grines et al., Circulation, 84: II-365 (1991), which failed to prevent restenosis, results in a peak plasma concentration of 2 ng/ml, or 5 nM (m.w. colchicine=399.4). Bochner et al., Handbook of Clinical Pharmacology, Little, Brown and Co., Boston (1983), pp. 151–152. Assuming (i) similar absorption and distribution of colchicine in rabbits; (ii) an average rabbit body weight of 3 kg. and (iii) an average human body weight of 70 kg., the dose of 0.2 mg/kg/day employed by Currier et al., Circulation, 80: II-66 (1989), which succeeded in preventing restenosis, corresponds to a plasma concentration in rabbits of 28 ng/ml or 70 nM. Thus, the concentration of colchicine in rabbits shown to prevent restenosis was 14 times the concentration achieved in the clinical trial. The compounds of invention can be prepared in the above-described compatible binding media up to 100 μM, i.e., 1400 times the concentration shown to be effective in the animal study, and delivered directly to the arterial wall by catheter during an angioplasty procedure.

The pharmaceutical preparations of the invention are preferably administered by injection, intraperitoneal infusion, or catheterization. Other modes of administration may also be effective, such as oral administration in some cases, or aerosolization.

The pharmaceutical preparation may be administered at appropriate intervals. Due to the nature of the compounds of the invention, repeated administration is likely to be unnecessary. Methods for determining the frequency of administration of the pharmaceutical preparations are well known to those skilled in the relevant medical art. In any event, the appropriate interval in any particular case would normally depend on the condition of the patient, and the type of pathological condition being treated.

The following examples are provided to describe the invention in further detail. These examples are intended to illustrate certain aspects of the invention and should in no way be construed as limiting the invention.

EXAMPLE 1

Determination of Membrane Retention Coefficient

The membrane retention coefficient (MRC) provides information regarding how well a given compound is retained in the plasma membrane of a cell and is determined as described below.

Generation of red blood cell ghosts for use as a model membrane is achieved by centrifuging whole blood at 300×g for 15 minutes, removal of the plasma and resuspension of the cell pellet in 0.83% (w/v) ammonium chloride. The ghosts are pelleted from the ammonium chloride by centrifuging at 10,000×g for 10 minutes. This ammonium chloride washing procedure is repeated a minimum of five times to insure that complete release of hemoglobin from the cells has occured. The ghosts are labeled with the compound in question at a concentration allowing for detection of the labeled ghosts by instrumental analysis or fluorescent microscopic methods, and at a concentration similar to those that would be used to label cells for a specific application as described above. For the determinations hereinbelow stock solutions of the compounds in question were prepared in ethanol at a molar concentration of $2\times10^{-3}$, and working dilutions of the compounds were prepared in iso-osmotic sucrose (52 g/500 ml distilled water). After incubation of the ghosts at an approximate concentration of $1\times10^9$ ghosts/ml in the working dilutions of the compounds for 10 minutes, the samples were centrifuged at 10,000×g to pellet the ghosts and the staining solution was aspirated from the samples. The labeled ghosts were resuspended in 1 ml of phosphate buffered saline solution containing 10% fetal bovine serum (PBS-FBS). Triplicate 20 ul aliquots were removed from each sample for the determination of the amount of total compound present. The samples were centrifuged as described above and triplicate 20 ul aliquots were removed from the supernatant for quantitative determination of amount of unbound compound present.

After sampling, the supernatant was aspirated and the red cell ghost pellet was resuspended in 1.0 ml of the PBS-FBS, which was once again sampled as described above. This procedure was repeated at least six times, allowing for detection of rapidly released compounds and was monitored after times equal to or greater than 24 hours to allow for the detection of more slowly released compounds. For the determination of the amount of compound present in each sample, the 20 ul aliquots were extracted into 3.0 ml of n-butanol by shaking. The samples were centrifuged at 3000×g to remove membrane debris and the butanol fractions were assayed for compound concentration. Fluorescent compounds are assayed in this manner using peak excitation and emission wave lengths for the particular compounds being assayed to determine the fluorescence units for each sample. Radiolabeled compounds do not require butanol extraction and may be assayed directly using beta or gamma counting instrumentation.

The determination of the amount of compound present in each sample as described above allows for the calculation of the MRC for each washing or fixed time point. The value is obtained by the following formula:

$$((C_T-C_S)/C_T)*100$$

wherein $C_T$ represents the amount of compound present (in units determined by the method used to assay the compound) in the total sample and $C_S$ represents the amount of compound present in the supernatant sample for that particular time point. The comparison of the MRC values defines criteria for identification of the compounds of this invention, these criteria being: 1) the MRC values determined for each washing steps should have a value of at least about 90 and 2) the percent difference between MRC values over at least a 24 hour time period should be less than about 10%.

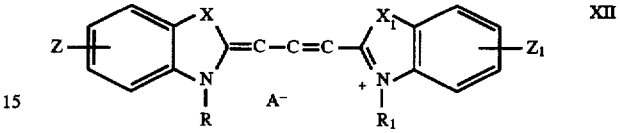

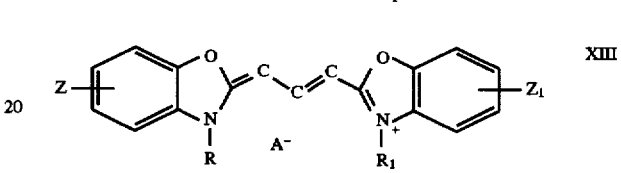

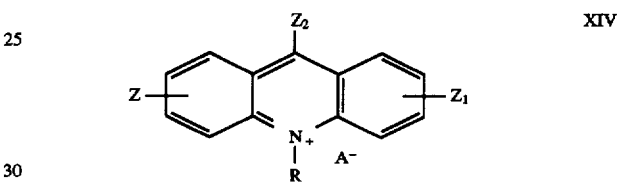

The data provided in Table I below are the results from one experiment and serve as an example of the MRC determination. In Table I, the compounds identified as A- C are of the formula XII, above, in which X and $X_1$ in each compound represents $C(CH_3)_2$ and Z and $Z_1$ represent H, with R/$R_1$ representing C-5/C-5/ (compd. A) , C-10/C-10 (cmpd., B) and C-14/C-14 (cmpd. C); the compounds identified as D-K are also of the formula XIII, in which Z and $Z_1$ represent H, with R/$R_1$ representing C-14/C-3 (cmpd. D), C-18/C-3 (cmpd. E), C-20 (3,7,11,15-tetramethylhexadecyl) /C-3 (cmpd. F), C-22/C-3 (cmpd. G), C-20/C-3 (cmpd. H), C-18/C-8 (cmpd. I), C-18/C-5 (cmpd. J), and C-22/C-3 (cmpd. K); and the compounds identified as L-N are of the formula XIV, above, in which Z and $Z_1$ each represent $N(CH_3)_2$ (in the 3 and 6 ring positions), and $Z_2$ represents H, with R representing C-22 (cmpd. L), C-18 (cmpd. M) and C-26 (cmpd. N). In compound K, the anion is chloride; in all of the remaining compounds, the anion is iodide.

TABLE I

| | CHANGE (Δ) IN MEMBRANE RETENTION COEFFICIENTS (MRCs) | | | | | | | |
|---|---|---|---|---|---|---|---|---|
| COMPOUND | WASH 1 | WASH 2 | WASH 3 | WASH 4 | WASH 5 | WASH 6 | 24 HR | Δ MRC |
| A | 51.63 | 51.12 | 44.82 | 41.39 | 12.59 | 17.48 | 0.00 | 100.00% |
| B | 83.28 | 92.36 | 94.63 | 94.94 | 95.33 | 94.80 | 54.08 | 42.95 |
| C | 94.85 | 97.24 | 98.40 | 98.64 | 98.43 | 99.12 | 93.90 | 5.26 |
| D | 50.40 | 61.20 | 64.45 | 65.85 | 70.62 | 77.92 | 18.84 | 75.82 |
| E | 90.69 | 94.74 | 96.28 | 96.74 | 96.41 | 97.17 | 53.81 | 44.62 |
| F | 88.82 | 93.94 | 95.15 | 95.26 | 94.51 | 96.64 | 36.77 | 61.64 |
| G | 94.42 | 96.96 | 98.03 | 97.93 | 97.92 | 98.34 | 96.90 | 1.46 |
| H | 91.70 | 97.22 | 97.97 | 98.24 | 98.09 | 98.40 | 90.10 | 8.43 |

TABLE I-continued

CHANGE (Δ) IN MEMBRANE RETENTION COEFFICIENTS (MRCs)

| COMPOUND | WASH 1 | WASH 2 | WASH 3 | WASH 4 | WASH 5 | WASH 6 | 24 HR | Δ MRC |
|---|---|---|---|---|---|---|---|---|
| I | 94.69 | 98.24 | 98.32 | 98.78 | 98.96 | 99.73 | 97.65 | 2.08 |
| J | 94.07 | 96.99 | 98.66 | 98.39 | 98.82 | 97.56 | 87.24 | 10.57 |
| K | 97.35 | 98.47 | 98.16 | 98.99 | 99.01 | 99.46 | 97.90 | 1.56 |
| L | 97.90 | 98.89 | 98.90 | 99.18 | 99.09 | 99.22 | 96.82 | 3.12 |
| M | 91.01 | 95.12 | 95.82 | 96.42 | 96.27 | 97.01 | 42.88 | 55.79 |
| N | 95.97 | 97.51 | 98.32 | 98.48 | 98.71 | 98.88 | 98.27 | 0.61 |

The MRC values set forth in Table I, above, show excellent correlation with the results obtained from intracellular compound transfer analysis, as described previously in the above-mentioned international application, PCT/US89/00087.

EXAMPLE 2

Determination of Membrane Binding Stability

It is known that the free energy of transfer of a hydrocarbon chain from an aqueous phase (e.g., the extracellular medium) to a liquid hydrocarbon phase (e.g., the hydrocarbon interior of a biomembrane) is dependent on the degree of branching, the degree of unsaturation, and the number of methylene groups in the hydrocarbon chain. The free energy of methylene-hydrocarbon interaction is minimal for the methylene group closest to the aqueous interface and increases for successive methylene groups, becoming approximately equal to that found for a hydrocarbon in a non-polar hydrocarbon-containing solvent for hydrocarbon groups 4 or more carbons into the lipid interior of the membrane. It is possible, therefore, to calculate for any structure, such as the compounds of the present invention, which contain a polar head group and linear hydrocarbon tails (single or multiple, symmetric or asymmetric) consisting of 4 or more carbons, the number of carbon equivalents which would give an approximately equal free energy of binding when fully immersed in a hydrocarbon solvent, as follows:

Carbon Equivalents=0+0.25+0.5+0.75+n−4(+)0+0.25+0.5+0.75+m−4(+) . . . where n equals number of linear hydrocarbons in first tail, m equals number of linear hydrocarbons in second tail, etc.

It has been experimentally determined that a correlation exists between carbon equivalents of the compounds of the invention and their membrane retention coefficients (MRC), determined as described in Example 1, above. For example, compounds of the invention having carbon equivalents of >18–19 have an MRC of 90 or greater and exhibit minimal transfer between labeled and unlabeled cells in an intracellular compound transfer assay (see above). Therefore, it would be expected that these compounds should also exhibit good in vivo stability of association with labeled cells. Surprisingly, this is not the case. Indeed, several compounds of the invention exhibiting MRC which differ by only 10% exhibit in vivo rates of loss which vary tenfold.

It is important in various practical applications of the compounds and methods of the invention to be able to assess, with some measure of predictability, the stability of association between compounds and biomembranes in vivo. For example, very stable binding to membranes might be required for applications such as delivery of therapeutic radionuclides to tumor sites, as loss of compound could lead to the radionuclide producing its toxic effect at non-tumor sites. On the other hand, more rapid loss of compound from biomembranes may be desirable for application involving controlled delivery rates of therapeutic agents. Accordingly, there is described hereinbelow an assay for determining MBS under conditions approximating those found in vivo.

In carrying out this assay, approximately physiological concentrations of serum albumin (5%) are used. Further, because many compounds of the invention are of low solubility in saline containing 5% albumin, an equilibrium between solubility in membranes and solubility in the surrounding medium is reached within 24 hours in a closed system containing a limited volume of "physiological" fluid. To better approximate the effects of large fluid volumes to which labelled cells are exposed in vivo, the assay for MBS is carried out by suspending a decreasing number of labeled membrane ghosts in a fixed volume of albumin-containing saline. At 24 hours, the total amount of label present is determined by sampling the well mixed suspension; subsequently, the membrane ghosts are pelleted by centrifugation and the amount of label released into the supernatant is determined and expressed as a percent of total label. Percent retention is plotted against number of ghosts per ml. of suspension, and MBS is determined as the area under the curve between $5 \times 10^7$ ghosts/ml. and $4 \times 10^8$ ghosts/ml. In this assay, a compound which exhibits infinite membrane binding stability would give an MBS of $3.5 \times 10^{10}$, and the results are expressed as a percentage of this maximal MBS.

The following table sets forth data from MRC determinations as described in Example 1, above, and MBS determinations of the present example, respectively, on a representative sample of compounds of the invention. The compounds identified as O-T were of formula XII, in which X and X1 represent $C(CH_3)_2$ and Z and $Z_1$ represent H, with R/R$_1$ representing C-12/C-10 (cmpd. O), C-22/C-12 (cmpd. P), C-14/C-3 (cmpd. Q); c-14/c-14 (cmpd. R) , and C-16/C-16 (cmpd. S), and C-22/C-14 (cmpd. T).

TABLE II

| Compounds | Carbon Equivalents | MRC# (at 24 hr.) | MBS (% of max.) | In vivo membrane half-life (days)* |
|---|---|---|---|---|
| O | 15 | 30 ± 4.7 | 19 ± 3.5 | <1 |
| P | 19 | 65 ± 2.0 | 48 ± 3.1 | 1.4 |
| Q | 20.25 | 85 ± 0.6 | 41 ± 5.0 | 10 ± 0.7 |
| R | 23 | 87 ± 0.6 | 55 ± 1.7 | 36 |
| S | 27 | 87 ± 1.2 | 79 ± 3.7 | 58 |
| T | 31 | 97 ± 0.1 | 85 ± 1.7 | 130 ± 17 |

*Half life for loss of dye from rabbit erythrocytes after labeling and reinjection in vivo determined as described in Slezak and Horan, Blood 74: 2172–77, (1990) (± standard error of the mean).

From the foregoing table, it can be seen that the MBS assay enables one to discriminate among compounds which differ little in MRC but which exhibit differing stabilities of in vivo association with biomembranes.

An added benefit of using the MBS assay to select compounds with appropriate binding characteristics for use in the various applications of the invention is that it is capable of identifying effects of variation in head group structure on membrane binding stability, whereas the MRC assay is only poorly capable of this. As can be seen in Table III, below, both hydrocarbon tail length (expressed as carbon equivalents to allow comparison of symmetric and asymmetric structures) and head group structure can have a significant effect on membrane binding stability, with the head group effect being more pronounced at low to intermediate numbers of carbon equivalents. Therefore, for other types of head groups carrying various functional groups useful in the practice of the invention (e.g., radiometal chelators, proteins, peptides, radionuclides and the like), similar effects may be determined, and the balance between head group effect and carbon equivalents needed to arrive at a desired membrane binding stability may be estimated. Compounds with MBS of at least about 30% or greater are expected to have utility in applications of the invention of the types described herein. It can also be observed that substituents on the head groups may have a significant effect on membrane binding stability, even though the number of carbon equivalents is kept constant. As can be seen in Table III below, Compounds AC and AD differ only in headgroup substituent, yet their respective MBS values are quite different.

In Table III, the compounds identified as U, W and Y are of formula XIII, above, in which X and $X_1$ in each compound represent 0 and Z and $Z_1$ represent H, with R/$R_1$ representing C-22/C-3 (cmpd. U), C-14/C-14 (cmpd. W) and C-18/C-18 (cmpd. Y); the compounds identified as V, X and AA are also of formula XII, in which X and $X_1$ represent S and Z and $Z_1$ represent H, with R/$R_1$ representing C-22/C-3 (cmpd. V), C-14/C-14 (cmpd. X), and C-18/C-18 (cmpd. AA).

The compounds identified aS AB, AC and AD are of the formula XII above, in which X and $X_1$ represent $(CH_3)_2$, $Z_1$ represents H, and R/$R_1$ represent C-14/C-22 (cmpd.AB) and C-14/C-3 (cmpds. AC, AD). In compound AB, Z represents —$CH_2$-NHOCH. In compound AC, Z represents H. In compound AD, Z represents a non-cleavable colchicine derivative as shown below.

TABLE III

| Compound | Type of Headgroup | Carbon Equivalents | MBS |
|---|---|---|---|
| Q | Indocarbocyanine | 20.25 | 42 ± 5.7 |
| U | Oxacarbocyanine | 20.25 | 47 ± 3.1 |
| V | Thiacarbocyanine | 20.25 | 64 ± 3.4 |
| R | Indocarbocyanine | 23 | 55 ± 1.6 |
| W | Oxacarbocyanine | 23 | 77 ± 1.1 |
| X | Thiacarbocyanine | 23 | 91 ± 1.3 |
| T | Indocarbocyanine | 31 | 85 ± 1.7 |
| Y | Oxacarbocyanine | 31 | 93 ± 1.0 |
| AA | Thiacarbocyanine | 31 | 94 ± 1.5 |
| AB | Indocarbocyanine | 31 | 91 ± 0.5 |
| AC | Indocarbocyanine | 12.25 | 10 ± 2.1 |
| AD | Indocarbocyanine | 12.25 | 28 ± 1.0 |

Many of the symmetrical dyes identified in Tables I–III are commercially available from Molecular Probes, Inc., Eugene, Oreg.

TABLE III

| Compound | Type of Headgroup | Carbon Equivalents | MBS |
|---|---|---|---|
| Q | Indocarbocyanine | 20.25 | 42 ± 5.7 |
| U | Oxacarbocyanine | 20.25 | 47 ± 3.1 |
| V | Thiacarbocyanine | 20.25 | 64 ± 3.4 |
| R | Indocarbocyanine | 23 | 55 ± 1.6 |
| W | Oxacarbocyanine | 23 | 77 ± 1.1 |
| X | Thiacarbocyanine | 23 | 91 ± 1.3 |
| T | Indocarbocyanine | 31 | 85 ± 1.7 |
| Y | Oxacarbocyanine | 31 | 93 ± 1.0 |
| AA | Thiacarbocyanine | 31 | 94 ± 1.5 |
| AB | Indocarbocyanine | 31 | 91 ± 0.5 |
| AC | Indocarbocyanine | 12.25 | 10 ± 2.1 |
| AD | Indocarbocyanine | 12.25 | 28 ± 1.0 |

EXAMPLE 3

Preparation of Compounds a. Preparation of 5-aminomethyl-1'-docosanyl-1-tetradeoyl-3,3,3',3'-tetramethylindo-carbocyanine iodide The title compound was prepared according to Reaction Scheme 1, described above. In the following description, the numbers given in parentheses indicate the corresponding numbered reagents shown in Reaction Scheme 1. The product obtained had the formula of compound 8 in which X and $X_1$ represent $C(CH_3)_2$ and R/$R_1$ represent $C_{14}H_{29}/C_{22}H_{45}$ and A represents I.

5-(N-phthalimidoaminomethyl)-2,3,3-(3H)-trimethylindolenine (1) was prepared by a modification of the procedure of Gale et al., Aust. J. Chem., 30:693 (1977). 2,3,3,-(3H)-trimethylindolenine (23.85 g, 0.15 mol, Aldrich) was dissolved in 150 ml of concentrated sulfuric acid. The flask was then placed in an ice bath and N-hydroxymethyl phthalimide (26.55 g, 0.15 mol, Fluka) added portion-wise over 30 mins. The ice-bath was removed and the solution stirred at room temperature for 5 days. The reaction mixture was then poured into 200 g of crushed ice and the pH adjusted to 9.0 with 50% NaOH solution while maintaining the temperature below 35° C. by adding ice as needed. The resulting precipitate was collected by filtration, washed with distilled water and dried under high vacuum overnight. The crude product was recrystallized from methylene chloride/hexane to yield 5-(N-phthalimidoaminomethyl-2,3,3-(3H)-trimethylindolenine (1) (30 g, 63%).

Docosanyl 4-chlorobenzene sulfonate was prepared using a procedure described in PCT/US89/00087.

Tetradecyl 4-chlorobenzene sulfonate was prepared in a similar fashion. 5-(N-phthalimidoaminomethyl)-2,3,3-(3H)-trimethylindolenine (6.36 g, 2 mmol) and tetradecyl-4-chlorobenzenesulfonate (7.62 g, 2 mmol) were combined and heated together at 130° C. for 2 hours. The reaction mixture was then cooled to room temperature and the crude product recrystallized from ethyl acetate to yield pure 5-(N-phthalimidoaminomethyl)-1-tetradecyl-2,3,3-(3H)-trimethylindolenium 4-chlorobenzene sulfonate (2) (10.23 g. 72%), m.p.=141° C.

2,3,3-Trimethyl-(3H)-indolenine (6.26 g, 0.04 mol, Aldrich) and n-docosanyl-4-chlorobenzene sulfonate (20.02 g, 0.04 mol) were heated together at 140° C. with stirring for 3 hours. The reaction mixture was then cooled to room temperature to give a waxy solid. The solid was then dissolved in ethanol (250 ml) and 200 ml of a saturated KI solution added and the solution stirred for 30 minutes. 1 liter of cold water was added and the stirring continued for a further 15 mins. The resulting precipitate was collected, washed twice with distilled water and dried under high vacuum overnight. The crude material was recrystallized from methylene chloride/hexane to yield pure 1-docosanyl-2,3,3-(3H) trimethyl-indolenium iodide (5) (14.5 g, 61%), m.p.=107°–110° C.

1-docosanyl-2,3,3-(3H)-trimethylindolenium iodide (8.94 g, 0.015 mol), N,N-diphenylformamidine (2.94 g, 0.015 mol, Aldrich) and acetic anhydride (60 ml) were placed in a round bottomed flask fitted with a condensor and the flask was purged with argon and then the condenser fitted with a drying tube. The flask was placed in a preheated oil bath (160° C.) and refluxed for 60 mins. The flask was then removed from the oil bath and cooled to room temperature. It was then transferred to a 1 liter Erlenmeyer flask and diluted with ethanol (60 ml) followed by 60 ml of a saturated KI solution and the mixture stirred for 30 mins. Cold water (800 ml) was added and the stirring continued for a further 15 mins. The precipitated product was collected by filtration, washed with distilled water and dried under high vacuum overnight to yield 2-(β-acetonilidovinyl)-1-docosanyl-3,3-(3H)dimethylindolenium iodide (6) (10.52 g, 95%), m.p.= 98°–100° C. The crude product was used without further purification.

5-(N-phthalimidoaminomethyl)-1-tetradecyl-2,3,3-(3H)-trimethylindolenium 4-chlorobenzene-sulfonate (2) (14.1 g, 20 mmol) was dissolved in 300 ml of concentrated HCl. The solution was slowly heated to 115° C. (caution, may froth) and refluxed for 22 hours. After this time the mixture was cooled to room temperature and placed in an ice bath. The pH was adjusted to 9.0 with ammonium hydroxide (30%) while maintaining the temperature between 15° and 20° C. The solution was then diluted to twice its volume with distilled water and extracted with methylene chloride (3×200 ml). The methylene chloride extracts were combined, dried over magnesium sulfate, and concentrated to provide 5-aminomethyl-3,3-dimethyl-2-methylene-1-tetradecyl-indoline as a yellow oil (3) (6.9 g, 90%).

5-aminomethyl-3,3-dimethyl-2-methylene-1-tetradecyl-indoline (14.88 g, 38.75 mmol) was dissolved in methyl formate (75 ml) and heated to reflux (55° C.) under argon for 24 hours. The solution was then cooled to room temperature and the methyl formate evaporated. The residue was recrystallized from hexane to yield 5-(N-formylaminomethyl)-3,3dimethyl-2-methylene-1-tetradecyl-indoline (4) (10.85 g, 68%).

2-(β-acetonilidovinyl)-1-docosanyl-3,3-(3H)-dimethylindolenium iodide (6) (740 mgs, 1 mmol) and 5-(N-formylaminomethyl)-3,3-dimethyl-2-methylene-1-tetradecyl-indoline (4) (330 mg, 0.8 mmol) and anhydrous sodium acetate (150 mg, 1.8 mmol) were dissolved in isopropanol and stirred at room temperature for 24 hours. The solution was then transferred to a 250 ml Erlenmeyer flask, diluted with ethanol (20 ml) and a saturated solution of KI (20 ml), and the mixture stirred for 30 minutes. The product was precipitated out by the addition of 100 ml of cold water and the resulting solution stirred for 15 minutes. The precipitate was collected by filtration, washed with distilled water and dried under high vacuum overnight. The crude product (870 mg) was split into two batches and each purified by flash column chromatography (silica gel, 10% isopropanol in methylene chloride) to yield pure 1'-docosanyl-5(N-formylaminomethyl)-1-tetradecyl-3,3,3', 3'tetramethylindocarbocyanine iodide (7) (414 mg, 52%).

100 mls of a concentrated HCl:methanol solution (prepared by mixing 11 ml of concentrated HCl and 120 mls of methanol) was added to 1'-docosanyl-5-(N--formylaminomethyl)-1-tetradecyl-3,3,3',3'-tetramethylindocarbocyanine iodide (7) (250 mgs) and the solution stirred at room temperature for 16–24 h. The solution was then diluted with ice water (100 ml), cooled in an ice bath and taken to pH 7.5–8.0 by the slow addition of saturated sodium bicarbonate solution. The aqueous phase was then extracted with methylene chloride (2×100 ml) and the combined organic phases dried over sodium sulfate, filtered, concentrated (Buchi bath temp. <30° C.) and then dried under high vacuum to give product (8) (240 mgs, 98%)

b. 2-[3-(2,3-dihydro-3,3-dimethyl-5-aminomethyl-1-tetradecyl-(2M)-indol-2-yliden)-1-propenyl]-1-docosanyl-benzoxazolium iodide The title compound was also prepared according to Reaction Scheme 1. In this description also, the numbers given in parenthesis indicate the corresponding numbered reagents shown in Reaction Scheme 1. The product obtained had the formula of compound (8) in which X represents $C(CH_3)_2$, $X_1$ represents oxygen, $R/R_1$ represent $C_{14}H_{29}/C_{22}H_{45}$ and A represents iodide.

A stirred solution of 2-methylbenzoxazole (2.65 g, 19.9 mmol, Aldrich) and docosanyl-4-chlorobenzenesulfonate (10.0 g, 19.9 mmol), prepared as previously described, was heated at 160°–170° C. (oil bath temperature) for 6 h. After this time, the reaction mixture was cooled to room temperature and the resulting solid mass recrystallized from methylene chloride to give pure 1-docosanyl-2-methylbenzoxazolium-4-chlorobenzene sulfonate (5) (7.3 g, 58%), m.p.=124°–125° C.

A stirred solution of 1-docosanyl-2-methylbenzoxazolium 4-chlorobenzenesulfonate (5) (1.5 g, 2.36 mmol), N,N'-diphenyl-formamidine (0.462 g, 2.36 mmol, Aldrich) and acetic anhydride (7 ml) was refluxed in an oil bath (preheated to 160° C.) for 30 mins. Upon cooling to room temperature, the mixture was diluted with absolute ethanol (15 ml) followed by a saturated solution of potassium iodide (10 ml) and stirred for 30 mins. Water (150 ml) was then added and the precipitated product collected by filtration, washed with water and dried under high vacuum overnight. The dried crude product was recrystallized from ethyl acetate to yield pure 2-(β-acetonilido-vinyl)-1-docosanyl-benzoxazolium iodide (6) (1.51 g, 90%), m.p.= 67°–68° C.

2-(β-acetonilidovinyl)-1-docosanyl-benzoxazolium iodide (6) (1.10 g, 1.53 mmol), 5-(N-formylaminomethyl)-1-tetradecyl-3,3-dimethyl-2-methylene indoline (4) (630 mgs, 1.53 mmol), prepared as in 3a., above, triethylamine (0.5 ml) and ethanol (25 ml) were heated at reflux for 1 hour. The solution was then cooled to room temperature, transferred to a Erlenmeyer flask and then diluted with ethanol (40 ml) and a saturated solution of KI (20 ml). This mixture was stirred for 30 minutes then 200 ml of cold water was added and this solution extracted with methylene chloride. The methylene chloride extracts were combined, dried over magnesium sulfate, filtered and concentrated to give a crude product. This product was purified by flash column chromatography (silica gel, 5% methanol in methylene chloride) to yield 2-[3-(2,3-dihydro-3,3-dimethyl-5-(N-formylaminomethyl)-1-tetradecyl-(2H)-indol-2-yliden)-1-propenyl]-1-docosanyl-benzoxazolium iodide (7) (305 mgs, 20%).

25 mls of a concentrated HCl:methanol solution, prepared as in a, above, was added to 2-[3-(2,3-dihydro-3,3-dimethyl-5-(N-formylaminomethyl)-1-tetradecyl-(2H)-indol-2- yliden)-1-propenyl]-1-docosanyl-benzoxazolium iodide (7) (50 mgs) and the solution stirred at room temperature for 16–24 hours. The solution was then diluted with ice water (30 ml), cooled in an ice bath and adjusted to pH 7.5–8.0 by the slow addition of saturated sodium bicarbonate solution. The aqueous phase was then extracted with methylene chloride (2×50 ml) and the combined organic phases dried over sodium sulfate, filtered concentrated (Buchi bath temp. 0°–5° C.) and then dried under high vacuum to provide product (8) (48 mgs, 99%).

c. Terephthaloyl N-Hydroxyl Succinimide Ester Derivative of 5-aminomethyl-1'-docosanyl-1-tetradecyl-3,3,3',3'-tetramethylindocarbocyanine iodide To a stirred solution of the di-N-hydroxysuccinimide ester of terephthalic acid (100 mgs, 0.278 mmol) (prepared by reacting terephthaloyl chloride with N-hydroxysuccinimide) in dry tetrahydrofuran (30 ml) at room temperature and under an argon atmosphere was added via cannula a solution of 5-aminomethyl-1'-docosanyl-1-tetradecyl-3,3,3',3'-tetramethylindocarbocyanine iodide, prepared as in Example 3a., above, in tetrahydrofuran (10 ml). The resulting solution was stirred for 2 h and then concentrated on the Buchi. The crude product obtained was purified by flash column chromatograph (silica gel, 5% methanol in methylene chloride) to furnish the title compound (101 mgs, 34%).

d. Substance P-5-lipophilic Cyanine Conjugate

To a stirred solution of substance P (21 mgs, 0.013 mmol) and the product of Example 3.c., above, (30 mgs, 0.024 mmol) in dry dimethylformamide (10 ml) at 0°–2° C. under an argon atmosphere was added triethylamine (60 ul) and the resulting solution stirred at 0°–2° C. for 4 hours. The reaction was then quenched by the addition of trifluoroacetic acid (100 ul) and the solution transferred to a 250 ml flask, diluted with water (80 ml) and lyophylised overnight. The resulting material was purified by passage through a column of octadecyl silica gel eluting with 80:20:1 (methanol: water: trifluoroacetic acid) first to remove unconjugated peptide and then 100:2:1 (methanol: water: trifluoroacetic acid) to elute the desired product. Fractions containing the peptide-lipophilic cyanine conjugate were combined, concentrated on the Buchi and the residue lyophilized from water (50 ml) to give pure conjugate as a purple powder (14 mgs, 40%). Purity by hplc was greater than 90% with less than 0.02% free Substance P. The conjugate thus obtained has the following structural formula (in which the conventional three letter symbols are used to show the amino acid sequence of Substance P):

Because the peptide and the cyanine reporter are both coupled to the spacer moiety via amide bonds, the resultant conjugate should be relatively stable in vivo.

e. 2-[3-(2,3-dihydro-3,3-dimethyl-5-(+)-biotinamidomethyl-1-tetradecyl-(2H)-indol-2-yliden) -1-propenyl]-1-docosanyl-benzoxazolium iodide A stirred solution of 2-[3-(2,3-dihydro-3,3-dimethyl-5-aminomethyl-1-tetradecyl-(2H)-indol-2-yliden)-1-propenyl]-1-docosanyl-benzoxazolium iodide (53 mgs, 0.055 mmol), prepared as described in Example 3b., above, in dimethylformamide under an argon atmosphere was cooled in an ice-bath. To this solution was added (+)-biotin 4-nitrophenyl ester (23 mgs, 0.63 mmol, Aldrich) and then imidazole (16 mgs, 0.23 mmol, Aldrich) and the solution was stirred in the ice-bath for 1 hour and then overnight at room temperature. The reaction mixture was then concentrated under high vacuum on the Buchi and the residue flash chromatographed (silica gel, 7.5% methanol in methylene chloride then 10% methanol in methylene chloride) to yield the title compound (22 mgs, 36%).

f. 5-{6-(6-(+)-biotinoylamidohexanamido)-hexanamidomethyl}-1'-docosanyl-1-tetradecyl-3,3, 3',3'-tetramethylindocarbocyanine iodide The same procedure as described in Example 3e., above, was again used with the following amounts of reagents: 5-aminomethyl-1'-docosanyl-1-tetradecyl-3,3,3',3'-tetramethylindocarbocyanine iodide (90 mgs, 0.09 mmol), prepared as in a above, 6[6-((biotinoyl)amino)hexanoyl amino]hexanoic acid N-hydroxy-succinimidyl ester (55 mgs, 0.097 mmol, (Molecular Probes), dimethylformamide (20 ml) and imidazole (20 mgs, 0.24 mmol). Flash chromatography (silica gel, 10% methanol in methylene chloride) gave the title compound (27.5 mgs, 21%).

The compounds 2-[3-(2,3-dihydro-3,3-dimethyl-5-(6-{(+)-biotinamido}-hexamidomethyl)-1-tetradecyl-(2H)-indole-2-yliden)-1-propenyl]-1-docosanyl-benzoxazolium and 2-[3-(2,3-dihydro-3,3-dimethyl-5-(6-(6(+)-biotinoylamido hexamido) hexamidomethyl)-1-tetradecyl-( 2H)-indol-2-yliden)-1-propenyl]-1-docosanylbenzoxazolium salts are similarly prepared from N-hydroxysuccinimidyl 6-(biotinamido) hexanoate and 6[6-((biotinoyl) amino) hexanoyl-amino] hexanoic acid N-hydroxysuccinimidyl ester, respectively (available from Molecular Probes).

g. N-n-docosanyl-N'-n-tetradecyl-5-tributylstannyl-3,3,3',3'-tetramethylindo-carbocyanine chloride The title compound was synthesized in accordance with Reaction Scheme 2. The product obtained had the formula of compound (13), in which X and $X_1$ represent $C(CH_3)_2$, R/$R_1$ represent $C_{22}H_{14}$/$C_{45}H_{29}$ and A represents Cl. 4-iodophenylhydrazine was prepared by the procedure of Blaikie et al., J. Chem. Soc., 313:296 (1924). Sodium nitrate

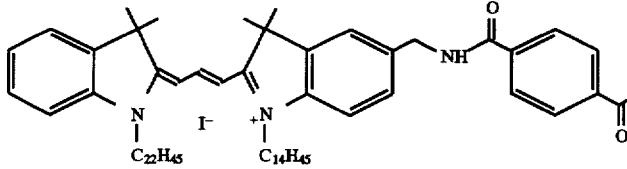
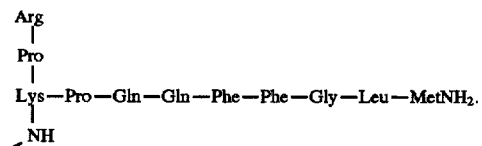

(16.56 g, 0.24 mol, Aldrich) dissolved in water (100 ml) was added dropwise within 45 mins. to a solution of 4-iodoaniline (43.9 g, 0.20 mol, Aldrich) in ice-water (600 ml) and concentrated hydrochloric acid (200 ml) which was cooled to 0°–2° C. The reaction mixture was stirred for a further 30 minutess at 0°–2° C. then tin(II) chloride (151.68 g, 0.8 mol, Aldrich) in c.HCl (150 ml) was added dropwise over 90 mins. while maintaining the temp. of the reaction mixture between 0°–2° C. Following the addition, the resulting solution was warmed to room temperature and stirred for 3 hours. The yellow solid which had separated from the solution was then collected by filtration, placed in ice water (800 ml) and the pH adjusted to 10 with 25% aqueous potassium hydroxide solution. The resulting solid was collected by filtration, washed with a small amount of water and dried under vacuum. The product was then placed in toluene (400 ml) and filtered to remove insoluble impurities. Hexane (1200 ml) was added and upon cooling in the refrigerator yellow needles separated which were collected by filtration, washed with hexane (100 ml) and dried under high vacuum to give pure 4-Iodophenylhydrazine (23.36 g, 50%), m.p.= 94° C.

5-Iodo-2,3,3-trimethyl-(3H)-indolenine (9) was prepared by a modification of the procedure of Moreau et al., *Eur. J. Med. Chem. Chim. Ther.*, 9 (3): 274–280 (1974). A solution of 4-iodophenyl-hydrazine (23.36 g, 0.0998 mol) and 2-methylbutanone (8.59 g, 0.0998 mol) in ethanol (100 ml) was refluxed for 3 hours. After this time, concentrated sulfuric acid (9.92 g, 0.0998 mol) dissolved in ethanol (100 ml) was added dropwise over one hour and the resulting solution refluxed for another 3 h. Upon cooling to room temperature, the solid which precipitated was removed by filtration, the filtrate concentrated to 80 ml and then poured into ice-water. The aqueous solution was then extracted with methylene chloride and the combined organic phases dried over magnesium sulfate, filtered and concentrated to yield crude product (26.9 g, 95.0%). The pure product 5-Iodo-2, 3,3-trimethyl-(3H)-iodolenine (9) (16.7 g, 59.0%) was obtained after vacuum distillation, b.p. 81°–88° C. at 0.03 mm of Hg.

5-Iodo-2,3,3-trimethyl-(3H)-indolenine (2.85 g, 0.01 mol) and n-docosanyl-4-chlorobenzenesulfonate (5.55 g, 0.01 mol) were heated at 130° C. (oil bath temp.) with continuous stirring for 4 hours. The subsequently cooled reaction mixture was recrystallized from ethyl acetate to provide tan crystals of N-n-docosanyl-5-iodo-2,3,3-trimethylindolinium 4-chlorobenzenesulfonate (10) (4.62 g, 59%) m.p.=118° C.

2,3,3-Trimethyl-(3H)-indolenine (6.36 g, 0.04 mol, Aldrich) and n-tetradecyl-4-chlorobenzene-sulfonate (15.52 g, 0.04 mol) were heated together at 130°–135° C. (oil bath temp.) for 3 hours with continuous stirring. The crude material was then dissolved in ethanol (200 ml) and then stirred with a saturated potassium iodide solution (50 ml) for 30 minutes. Cold water (500 ml) was added and the precipitate collected by filtration and washed well with cold water. The dried crude was crystallized from ethyl acetate and the collected crystals washed well with ether and dried to furnish N-tetradecyl-2,3,3-trimethylindolinium iodide (5) (12.8 g, 66.8%), m.p. 97° C.

N-Docosanyl-5-iodo-2,3,3-trimethylindolinium 4-chlorobenzenesulfonate (2.36 g, 3.0 mmol), N,N'-diphenylformamidine (0.59 g, 3.0 mmol, Aldrich) and acetic anhydride (20 ml) were placed in a 50 ml round bottom flask which was under an argon atmosphere and fitted with a reflux condensor and stirring bar. This flask was then placed in an oil bath which was preheated to a constant temperature of 170° C. and the mixture refluxed for 60 minutes. The reaction flask was then cooled to room temp. and then transferred to a 500 ml Erlenmeyer flask. The flask was then placed in an ice bath and saturated potassium iodide solution added. After stirring for 15 minutes, cold water (250 ml) was added and the mixture stirred for an additional 15 minutes. The precipitated product, N-n-Docosanyl-5-iodo-2-($\beta$-acetonilidovinyl)-3,3-dimethylindolinium iodide (11) (2.37 g, 91%), was collected by filtration and dried, m.p.=170° C. (decomp).

A mixture of N-docosanyl-5-iodo-2-($\beta$-acetonilidovinyl)-3,3-dimethylindolinium iodide (511 mgs, 0.59 mmol), N-tetradecyl-2,3,3-trimethylindolinium iodide (233 mg, 0.47 mmol) and anhydrous sodium acetate (48 mgs, 0.59 mmol, Aldrich) in absolute ethanol (15 ml) was stirred at room temperature for 24 hours. The deep red colored reaction mixture was then transferred to an Erlenmeyer flask and diluted with ethanol (25 ml). Silver acetate (492 mg, 2.95 mmol, Aldrich) dissolved in water (25 ml) was then added and the solution stirred for 15 minutes. Ethanol (25 ml) and saturated sodium chloride solution were then added and the stirring continued for 15 minutes. The solution was then transferred to a separatory funnel, diluted with water (200 ml) and extracted with methylene chloride (2×100 ml). The organic phases were dried over anhydrous magnesium sulfate., filtered and evaporated to afford a crude product. The crude product was purified by flash chromatography (silica gel, first 5% methanol in methylene chloride and then 8% methanol in methylene chloride) to furnish N-docosanyl-N'-tetradecyl-5-iodo-3,3,3',3'-tetramethylindocarbocyanine chloride (12) (272 mg, 58%).

N-docosanyl-N'-tetradecyl-5-iodo-3,3,3',3'-tetramethylindocarbocyanine chloride (12) (200 mg, 0.2 mmol) was dissolved in dry toluene (15 ml, freshly distilled from calcium hydride) and the resulting solution degassed by bubbling through argon gas. Bis-(n-tributyltin) (0.237 ml, 0.47 mmol, Aldrich) was then added via syringe followed by tetrakis(triphenylphosphine) palladium (0) (2.34 mgs, 2.0 umol, Aldrich). The resulting solution was refluxed under argon for 48 hours. The toluene was then removed in vacuo and the residue flash chromatographed (silica gel, 5% methanol in methylene chloride) to furnish the title compound (13) (71 mg, 31%). Found M+, 1122 $C_{71}H_{123}N_2Sn$ requires 1122.

Compound (13) is a versatile intermediate for the incorporation of radiohalogen atoms using procedures described by Wilbur et al., *J. Nucl. Med.*, 30: 216–226 (1989).

h. $^{186}$Re-Chelator nipophilic Cyanine Conjugate

The title compound was prepared according to Reaction Scheme 5 shown above. The reference numbers that appear in this reaction correspond to those of Reaction Scheme 5. The product obtained had the formula of compound 24, in which X and $X_1$ represent $C(CH_3)_2$ and R/$R_1$ represent $C_{14}H_{29}/C_{22}H_{45}$ and A represents I.

A bifunctional chelating agent, compound 22, (84.5 mg, 0.291 mmole) dissolved in 400 μL tetrahydrofuran (THF) was added to a pear shaped flask containing (8) (66.8 mg, 0.066 mmol). This solution was stirred at ambient temperature. The progress of the reaction was followed by thin-layer chromatography (TLC; silica, 90:10 $CH_2Cl_2$:MeOH). After 4 hours, the reaction mixture was diluted with hexane to yield a 75:25 THF:hexane solution and loaded onto a short path silica gel (20 g) column. Excess compound 22 was eluted with 50:50 hexane:EtOAc until the eluate gave a negative reaction with bromocresol green. The solvent composition was changed to 90:10 $CH_2Cl_2$:MeOH and compound 22 was eluted. The solvent was evaporated under reduced pressure to yield 65.0 mg of compound 23.

High field $^1$H nmr (300 MHz) showed a downfield shift of the benzyl methylene protons from 3.9 ppm to 4.5 ppm as seen previously in formyl protected compound 8. Relative integration of signals at 4.5 and 8.4 ppm indicated a 1:1 coupling ratio.

The product, compound 23, was converted to the HCl salt by the addition of an HCl gas/ethanol solution. An ethanolic solution of oxalic acid was added as an antioxidant, the solution evaporated, and the solid residue stored under nitrogen.

60 nmole Na$^{186}$ReO$_4$ in 107 µl N NaOH (0.181 mCi/nmol) was added to 150 µL of a transfer chelating solution (200 mg citric acid, 40 mg SnCl$_2$.2H$_2$O, and 20 mg gentisic acid dissolved in 2 mL H$_2$O) followed by addition of 43 µL 0.1M NaOH. The solution was vortexed for 1 minute and heated at 55° C. for 10 minutes. Ethanol (0.6 g mL) was added to the reaction mixture followed by 300 µL of an ethanolic solution of compound 23 (0.8 mg, 0.69 µmol). The solution was vortexed for 15 seconds and heating was continued for 1 hour.

The reaction mixture was loaded on a semiprep HPLC column (Waters Novapak, 7.5×300 mm) and eluted at a gradient of 50:50 A:B to 100% B over 30 min at a flow rate of 4.0 mL/min. (Solvent A was 75:25 H$_2$O:CH$_3$CN containing 0.1% trifluoroacetic acid (TFA) and 0.05% gentisic acid. Solvent B was 20:80 CH$_3$CN:THF containing 0.1% TFA and 0.05% gentisic acid.) The fraction eluting at about 20 minutes was identified as the fraction containing the title compound.

The fraction above was diluted 1:1 with Solvent 1(0.05% gentisic acid in H$_2$O) and loaded on a Sep-Pak column (C-18, Waters 36805) which had been washed first with 10 mL Solvent 2 (0.05% gentisic acid in EtOH) and then with 10 mL Solvent 1. The column was eluted with 10 mL Solvent 1, 150 µL Solvent 2, and 300 µL Solvent 2. This last fraction was taken as the product. The solvent was evaporated by an N$_2$ stream to a volume of ~10 µL and then diluted with EtOH to ~40 µL.

The concentration of the product as obtained above was determined to be 252 µM by absorption at 555 nm. The specific activity was 186±21 mCi/µmol compared to the theoretical value of 181 mCi/µmol. The recovery of product was ~9% of the total Re-186. Radiopurity was determined one day later by HPLC and found to be ~94%. Most of the impurity (~5%) was found at the void volume and assumed to be free perrhenate.

i. 7-N(5-oxopentanoyl) deacetyl colchicine Lipophilic Cyanine Hydrazone Conjugate and Determination of Acid-Cleavability (a) Preparation The title compound was prepared according to the procedure generally set forth in Reaction Scheme 3 above. The reference numbers herein correspond to those shown in Reaction Scheme 3. The product obtained had the formula of compound 19, in which X and X$_1$=C(CH$_3$)$_2$ and R/R$_1$=C$_{14}$H$_{29}$/C$_{22}$H$_{45}$ and A represents Cl.

5-Aminomethyl-1'-docosanyl-1-tetradecyl-3,3',3'-tetramethylindocarbocyanine iodide (compound 8) was prepared using the general procedure of Scheme 1 where R is C$_{14}$C$_{29}$; R$_1$ is C$_{22}$H$_{45}$; X and X$_1$=C(CH$_3$)$_2$.

To a stirred solution of monomethyl glutarate (0.14 ml, 1.1 mmol, Aldrich) in dimethylformamide (15 ml, distilled from lithium aluminum hydride) was added N-hydroxysuccinimide (126.5 mg, 1.1 mmol, Aldrich) at room temperature. This mixture was cooled in an ice bath and dicyclohexylcarbodiimide (226.6 mg, 1.1 mmol) was added. The reaction mixture was gradually warmed up to room temperature and stirred for a further three hours. Next, the reaction mixture was transferred into a flask containing freshly prepared compound 8 (700 mg, 0.7 mmol) and this reaction mixture was kept stirring at room temperature for 30 hours. The dimethylformamide was then removed under high vacuum and the resulting crude product dissolved in absolute ethanol (250 ml) and water (250 ml). Silver acetate (434 mg, 2.6 mmol) was then added and after 30 minutes stirring, saturated sodium chloride solution (100 ml) was added and the mixture stirred for another 30 minutes. The aqueous layer was extracted with methylene chloride (4×100 mL) and the combined organic layers were dried over anhydrous sodium sulfate, filtered and concentrated. The residue was flash chromatographed (silica gel, eluting with 2.5% then 5% then 10% methanol in methylene chloride) to provide 5-[N-(monomethylglutaryl)-aminomethyl]-1'-docosanyl-1-tetradecyl-3,3,3',3',-tetramethylindocarbocyanine chloride (14) (520 mg, 63%).

Anhydrous hydrazine (5 ml, Aldrich) was slowly added at room temperature to a stirred solution of the resultant 5-[N-(monomethylglutaryl)-aminomethyl]-1'-docosanyl-1-tetradecyl-3,3,3',3'-tetramethylindocarbocyanine chloride (520 mg, 0.44 mmol) in absolute ethanol (6 mL). The reaction mixture was kept stirring for 2 hours and then concentrated by rotary evaporation and the residue flash chromatographed (silica gel, eluting with 10% then 30% methanol in methylene chloride) to yield 5-[N-(monohydrazino)glutaryl-aminomethyl]-1'-docosanyl-1-tetradecyl-3,3,3',3'-tetramethyl- indocarbocyanine chloride (15) (110 mg, 27%)

Glutaric anhydride (111.2 mg, 0.975 mmol, Aldrich) was added at room temperature to a stirred solution of deacetyl colchicine (16) (0.2902 g, 0.81 mmol, Molecular Probes) in methylene chloride (5 ml) and the reaction mixture was kept stirring at room temperature for 2 hours. The methylene chloride was then removed by rotary evaporation and the crude product was dried under high vacumn to yield 7-(N-glutaryl) deacetyl colchicine (0.397 g, 100%) as a solid.

Carbonyldiimidazole (0.197 g, 1.22 mmol, Aldrich) was then added to a stirred solution of the 7-(N-glutaryl) deacetyl colchicine (0.397 g, 0.83 mmol) in dimethylformamide (5 mL, freshly distilled from lithium aluminum hydride) at room temperature and the reaction mixture kept stirring at room temperature for two hours. During this time a precipitate formed in solution. The dimethylformamide was removed by vacumn distillation and the residue was dissolved in methylene chloride (5 mL). To this solution was added tetrabutylam/nonium borohydride (250 mg, 0.972 mmol, Aldrich) and the resulting mixture was stirred for 3 hours. It was then poured into water (50 mL) and the organic layer separated and the aqueous layer back extracted with methylene chloride (2×25 mL). The combined organic layers were dried over anhydrous sodium sulfate, filtered and concentrated. The crude product was flash chromatographed (silica gel, 10% methanol in methylene chloride) to furnish 7-N-(5-hydroxylpentanoyl) deacetyl colchicine (17) (72 mg, 25%).

To a solution of the 7-N-(5-hydroxylpentanoyl) deacetyl colchicine (72 mg, 0.16 mmol) in methylene chloride (5 mL) at room temperature, was added pyridinium chlorochromate (41.3 mg, 0.19 mmol, Aldrich) and the mixture stirred for 2 hours. It was then poured into water (50 ml) and the organic layer was separated and the aqueous layer back extracted with methylene chloride (2×25 mL). The combined organic layers were dried over anhydrous sodium sulfate, filtered and concentrated. The resulting residue was flash chromatographed (silica gel, 10% methanol in methylene chloride) to yield 7-N-(5-oxopentanoyl) deacetyl colchicine (18) (35 mg, 49%) as an oil.

A solution of 5-[N-glutaryl(monohydrazino)-aminomethyl]-1'-docosanyl-1-tetradecyl-3,3,3',3'-tetramethylindocarbocyanine chloride (110 mg, 0.12 mmol) in absolute ethanol (20ml) was added to a flask containing the 7-N-(5-oxopentanoyl) deacetyl colchicine (40 mg, 0.088 mmol) and the reaction mixture stirred for 20 hours. The ethanol was then removed by rotary evaporation and residue flash chromatographed (silica gel, 10% methanol in methylene chloride) to furnish the title compound (19) (26.5 mg, 27%). Integation of the 200 MHz proton NMR of this compound indicated a 1:1 coupling ratio and fast atom bombardment mass spectrometry (glycerol/thioglycerol matrix) showed an $M^+=1429$ corresponding to the expected $M^+$ of the product ion $C_{90}H_{135}N_6O_8$. This product was additionally characterised by reverse phase high pressure liquid chromatography (HPLC), according to the conditions described below and had a retention time of 55 minutes. It was found to be 98% pure using UV detection at 350 nm. Less than 0.30% free 7-N-(5-oxopentanoyl) deacetyl colchicine (retention time=12 minutes) was detected in this product.

The HPLC system used comprised a Waters Model 600E solvent delivery system with W600E gradient controller, U6K injector and Model 990 photodiode array detector. Chromatography conditions were as follows: Column: Waters Nova-Pak (phenyl, 4 µm, 3.9 mm×15 cm); Mobile phase: Solvent A=Water:Methanol:Acetonitrile:PIC A reagent (Waters) (395:25:80:4), Solvent B=Water:Methanol:Acetonitrile:PIC A reagent (225:25:250:4), Solvent C=Methanol:Water:PIC A reagent (490:15:4). Gradient conditions: 100% (A) to 60%:40% (A:B) over 20 minutes then to 100% (C) over 10 minutes followed by 100% (C) for 40 minutes. Flow rate: 2 mL/min. Detection: photodiode array from 240–575 nm.

(b) Determination of Acid Cleavability

The rate of acid hydrolysis of hydrazone conjugate (19) to produce 7-N-(5-oxopentanoyl) deacetyl colchicine was studied by HPLC at 3 different pH's.

Buffer solutions were prepared according to the procedures described by Gomori, "Methods in Enzymology", 16:138 (1955). HPLC conditions and retention times were the same as described above. The detection limit for 7-N-(5-oxopentanoyl) deacetyl colchicine was determined to be approximately 100 ng at 350 nm.

Compound solutions to be studied were prepared by adding 50 µl of hydrazone conjugate solution (1 mg/ml of methanol) to a screw capped vial (1 ml) containing citrate phosphate buffer (200 µl) of the desired pH. The vials were kept closed and the solutions were analysed by HPLC (350 nm detection) for conjugate (19) remaining and 7-N-(5-oxopentanoyl) deacetyl colchicine produced at 24 h and 48 h. Each hplc injection was 200 µl.

The hydrolysis results at pH 4.21, 5.74 and 7.35 are summarized below.

pH 4.21: 78% of (19) had cleaved to produce (18) after 24 hours and 100% had cleaved after 48 hours.
pH 5.74: 45% of (19) had cleaved to produce (18) after 24 hours and 100% had cleaved after 48 hours.
pH 7.35: 36% of (19) had cleaved to produce (18) after 24 hours and 77% had cleaved after 48 hours.

The only free colchicine hydrolysis product of the hydrazone conjugate detected by HPLC was the expected aldehyde, compound 18.

j. Heparin Lipophilic Cyanine Conjugate

The title compound was prepared according to the procedure generally set forth in Reaction Scheme 4 above. The reference numbers herein correspond to those shown in Reaction Scheme 4. The product obtained had a formula of the type represented by compound 21 in which X and $X_1=C(CH_3)_2$, $R/R_1=C_{14}H_{29}/C_{22}H_{45}$ and A=Cl.

Compound 8 was prepared as previously described above.

Freshly prepared compound 8 (18.0 mg, 18.0 µmol) was dissolved in deuterated chloroform (0.5 ml, Aldrich) in an NMR tube. Triethylamine (5 µl, 0.036 mmol) was added followed by triphosgene (1.95 mg, 6.7 µmol, Aldrich) and this mixture was shaken for a couple of minutes. A proton NMR was then taken and showed a shift in the benzylic protons from 3.95 as seen in compound (8) to 4.95 indicating formation of the product 5-isocyanatomethylene-1'-docosanyl-1-tetradecyl-3,3,3',3'-tetramethylindocarbocyanine chloride (20). The deuterated chloroform solution of the isocyanate (20) was concentrated by rotary evaporation and the residue was dissolved in dimethylformamide (4ml, dried and distilled) and stirred rapidly. To this rapidly stirring solution was added a formamide solution of heparin (9.4 mg/ml, 2 ml, 0.0016 mmol) and the flask was capped and stirred at room temperature for 20 hours. The insoluble material was then removed by filtration and the filtrate concentrated by rotary evaporation at 50° C. under high vacuum. The residue was added to a mixture of water (20ml) and methylene chloride (20 ml). The aqueous layer was separated and washed with methylene chloride one more time. The aqueous solution was then placed in a dialysis bag (Spectra/Por membrane MWCO:1000) and dialysed against water and then lyophilised to give a pink solid (24.3 mg). This material was not purified further and was believed to be a mixture of compound 21 and unreacted heparin. It was used, as is, for biological evaluation (see Example 14).

EXAMPLE 4

Biological Effects of Conjugating Therapeutically Active Protein to Lipophilic Molecule The in vivo receptor pharmacology of the compound produced in Example 3d., above, was studied in a rabbit blood perfused hind limb preparation similar to that described by U. Forstermann et al., *J. Pharmacol. Exp. Ther.*, 234: 1055–61 (1987). Blood from a pentobarbital anesthetized, artificially ventilated rabbit was withdrawn from a cannulated carotid artery, passed within medical grade silastic tubing through a constant speed roller pump, and directed to a cannulated femoral artery. Distal perfusion pressure in the femoral arterial bed was measured (in mm Hg) by means of a micropressure transducer (Millar) passed down the perfusion tubing so as to lie just beyond the tip of the femoral catheter. Initially, pump speed was adjusted so that distal perfusion pressure approximated systemic mean arterial blood pressure after which blood flow was kept constant for the remainder of each experiment. Changes in resistance then varied directly as distal perfusion pressure in a manner similar to that described by Ohm's law, such that:

Vascular Resistance=Perfusion Pressure Blood Flow

Thus, by maintaining blood flow constant for the duration of each experiment, changes in distal perfusion pressure directly reflected vascular resistance such that a decrease in pressure signifies vasodilation and an increase in pressure signifies vasoconstriction. Direct injection into the perfusion circuit could thus be used to assess the vascular biology and pharmacology of substances believed to exert actions on in vivo vascular smooth muscle tone.

Figures 1, 3A:
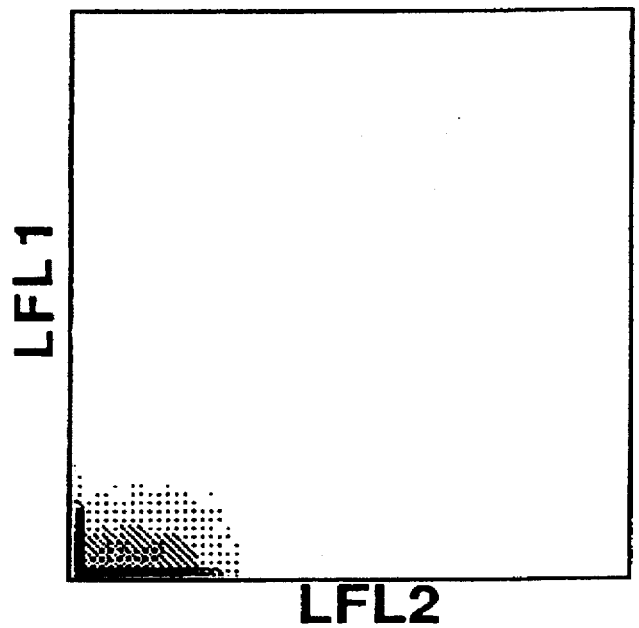
Figures 2, 3A:
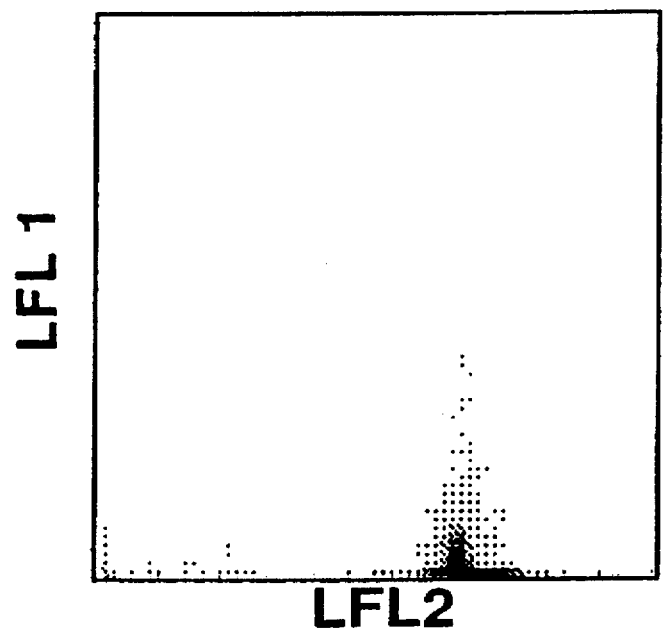

FIG. 1 shows the qualitative similarity of the in vivo responses to substance P and the conjugate of Example 3d. Both substance P and the conjugate produce brief, dose-related decreases in hind-limb perfusion pressure when injected locally into the perfused rabbit hind-limb preparation. These dilator responses are entirely consistent with the known vascular pharmacology of substance P. See, for example, J. Beny et al., *J. Physiol.*, 398: 277–89 (1988).

Figure 2:
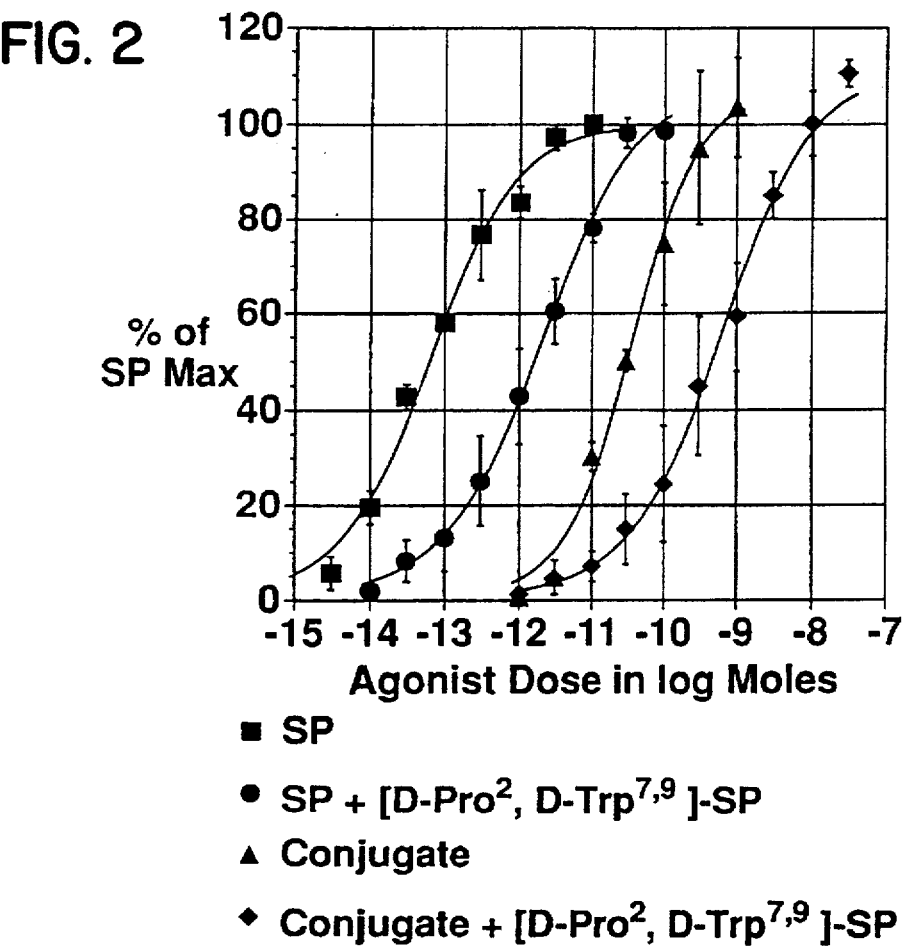
FIG. 2 shows the dose-response relationship of each of Substance P and a Substance P-lipophilic cyanine conjugate of the invention, both in the absence and in the presence of the Substance P antagonist, [D-Pro$^2$, D-Trp$^{7,9}$]-SP.

As can be seen in FIG. 2, there are quantitative differences between responses to substance P and the conjugate. The average threshold dose of substance P required to produce a fall in perfusion pressure is approximately 0.003 pmoles while the maximum fall in pressure is achieved in the dose-range of 3–10 pmoles. The minimum dose of conjugate required to provoke a fall in perfusion pressure is higher than that of substance P, being 1–10 pmoles while the maximum fall is achieved at 1000 pmoles. Calculated $ED_{50}$ values by logistic function for substance P and the conjugate were 0.13 and 34 pmoles, respectively, demonstrating a 250-fold greater potency for substance P. However, both substances displayed dose-response curves with parallel slopes consistent with an interaction at a common receptor. FIG. 2 also presents the dose-response relationships of both substance P and the conjugate during infusion of a known antagonist of substance P, [D-$Pro^2$,D-$Trp^{7,9}$]-substance P. This synthetic peptide with D-amino acids in 3 positions has been reported to antagonize the neuronal, behavioral, and vascular actions of endogenous substance P and exogenously administered substance P. The decrease in perfusion pressure to both substance P and the conjugate is inhibited by [D-$Pro^2$,D-$Trp^{7,9}$]-substance P, as assessed by parallel shifts to the right in the dose-response curves of both compounds when the antagonist is present. The magnitude of the rightward shift of the dose-response curves in the presence of the antagonist is similar for both substance P and the conjugate, further suggesting that these two substances act at a common receptor site. The data set forth in FIG. 2 were based on tests involving three rabbits and are expressed as the mean (±SEM) percent change in perfusion pressure from the maximum response to substance P in the absence of antagonist.

In addition to the above, it has been experimentally determined that administration of the corresponding unconjugated lipophilic cyanine at concentrations of 1 and 10 nmoles has no vascular relaxing action. Also, administration of the beta-adrenoceptor agonist, isoproterenol, at 1, 10, 100 pmoles concentrations also produced a dose related decrease in perfusion pressure but which was not antagonized by the SP antagonist, [D-$Pro^2$,D-$Trp^{7,9}$]-SP, demonstrating the specificity of [D-$Pro^2$, D-$Trp^{7,9}$]-SP for SP receptors.

The conjugate of Example 3d. (100 uM) readily binds to washed rabbit red blood cells suspended in phosphate buffered saline with 1 mM EDTA and 0.5% rabbit serum albumin) when the two are incubated together ex vivo. The fluorescent moiety of the conjugate allows its ready detection on RBCs by flow cytometry. When conjugate labeled rabbit RBCs are injected in the rabbit hind-limb, a reduction in perfusion pressure occurs, the magnitude of which is related to the number of injected cells. Further experiments have demonstrated that injection of $10^6$–$10^9$ RBCs results in graded decreases in perfusion pressure in the rabbit hind limb preparation. When a sample of conjugate labeled RBCs was separated into a supernatant fraction and a cell fraction, which was resuspended in the above RBC buffer and then reinjected, the supernatant fraction contained a significant portion of the biological activity of the original cell suspension, demonstrating that the conjugate is capable of diffusing off the RBCs. Repeated washings of the RBCs resulted in supernatant fractions with vasodilator activity, suggestive of prolonged release capability of the conjugate from RBCs.

From the foregoing experiments, it will be appreciated that the Substance P-lipophilic cyanine conjugate of Example 3.d., above, is capable of vasodilative activity which is qualitatively similar to that of native Substance P and that such activity can be antagonized by a known antagonist of substance P receptors. These experimental results tend to indicate that interaction of substance P with its receptor is preserved despite chemical conjugation with a lipophilic reporter molecule.

EXAMPLE 5

Determination of Effect of Cell Binding on Structure and Biological Interactions of Substance P Derivatized with Lipophilic Cyanine To determine whether the substance P component of the conjugate of Example 3d. was structurally unaltered and recognizable on the surface of peripheral red blood cells (RBCs), 2 ml of human RBCs ($10^6$ cells/ml) were labeled with the conjugate (10 μM; red fluorescence) and then studied using flow cytometry. The results of this study are presented in FIG. 3 A–C. Specifically, untreated RBCs and conjugate-labeled RBCs were analyzed to determine if:

1. The conjugate was incorporated on the surface of cells (FIG. 3A comparison).
2. Fluorescein isothiocyanate (FITC) conjugated goat anti-rabbit antibodies nonspecifically bound to the conjugate-labeled or non-labeled cells (FIG. 3B comparison), or
3. rabbit anti-substance P antibodies+FITC anti-rabbit antibodies specifically bound to the conjugate-labeled RBCs (FIG. 3C comparison).

In FIG. 3A, examination of unstained RBCs represents only background autofluorescence (cell population located near origin on both green (LFL1) and red (LFL2) axes), while the conjugate-labeled cells show an increased red fluorescent signal when compared with the unlabeled cells.

Figures 1, 3B:
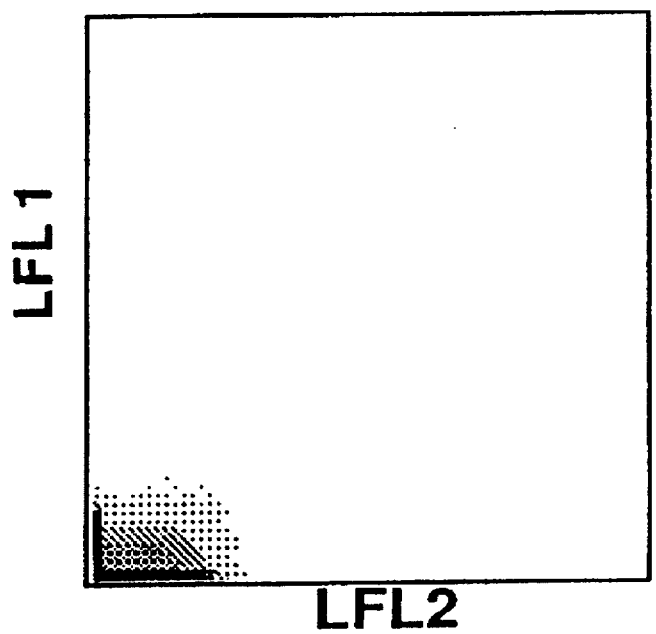
Figures 2, 3B:
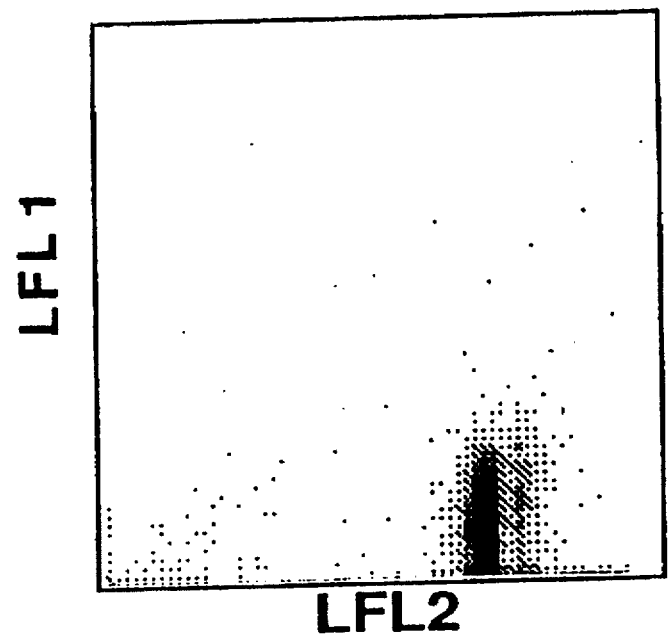

In FIG. 3B, treatment of conjugate-labeled cells with a fluoresceinated goat anti-rabbit antibody demonstrated that this antibody has only minimum non-specific binding to RBCs, as evidenced by a small increase in green fluorescent signal (LFL1) when compared to the results in FIG. 3A.

Figures 1, 3C:
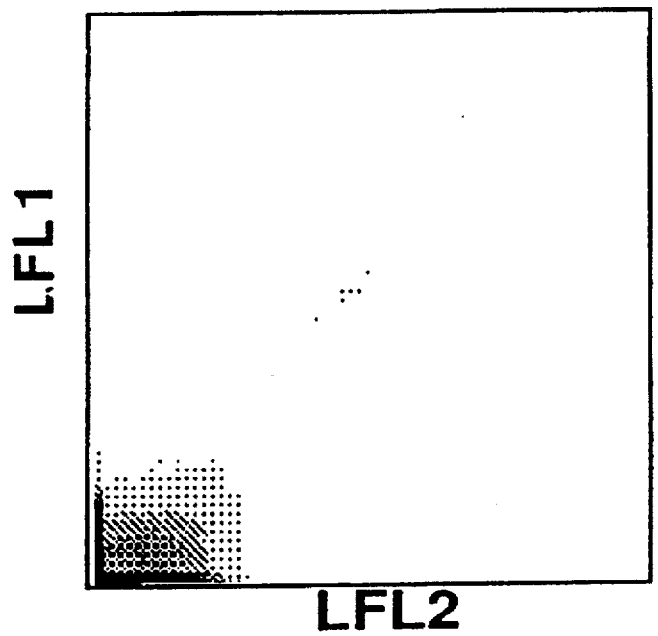
Figures 2, 3C:
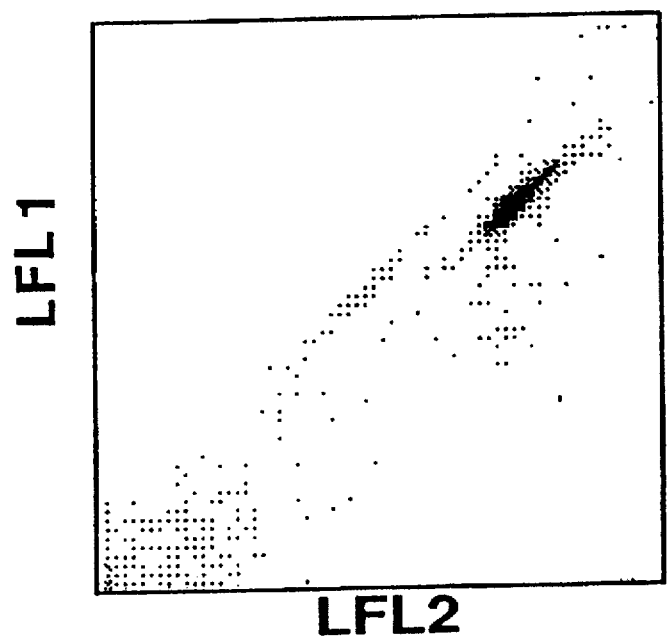

FIG. 3C shows the fluorescent histograms of unlabeled RBCs or conjugate-labeled RBCs which are also indirectly fluorescently labeled using rabbit anti-substance P antibody as the primary reagent and then fluoresceinated goat anti-rabbit antibody as the secondary reagent. In conjugate-labeled cells, there is a significant amount of both green and red fluorescence detectable on the cells (LFL1 signal increase over FIG. 3B), demonstrating specific binding to cell-associated conjugate. This fluorescence increase is not noted with the RBCs that have not been labelled with conjugate. Thus, this technique demonstrates that Substance P is antigenically "recognized" on the surface of RBCs by an anti-substance P antibody, confirming the presence and conservation of structure of Substance P on red cells.

EXAMPLE 6

Determination of In Vivo Stability of Substance P-Lipophilic Cyanine Conjugate on Red Blood Cells To study the in vivo characteristics of red blood cells labeled with the conjugate of Example 3d., above, 0.5 ml of fresh anticoagulated blood from each of 2 rabbits was labeled with the conjugate (final concentration, 10 µM) and injected back in the same rabbit from which the blood was taken. After the conjugate labeling but prior to injection, an aliquot of labeled cells was examined by flow cytometry to insure adequate labeling. Following in vivo administration of the labeled cells, blood samples were removed at 30 minutes, and then 1, 2, 3, 4, and 7 days and examined by flow cytometry for fluorescent cells.

Figure 4:
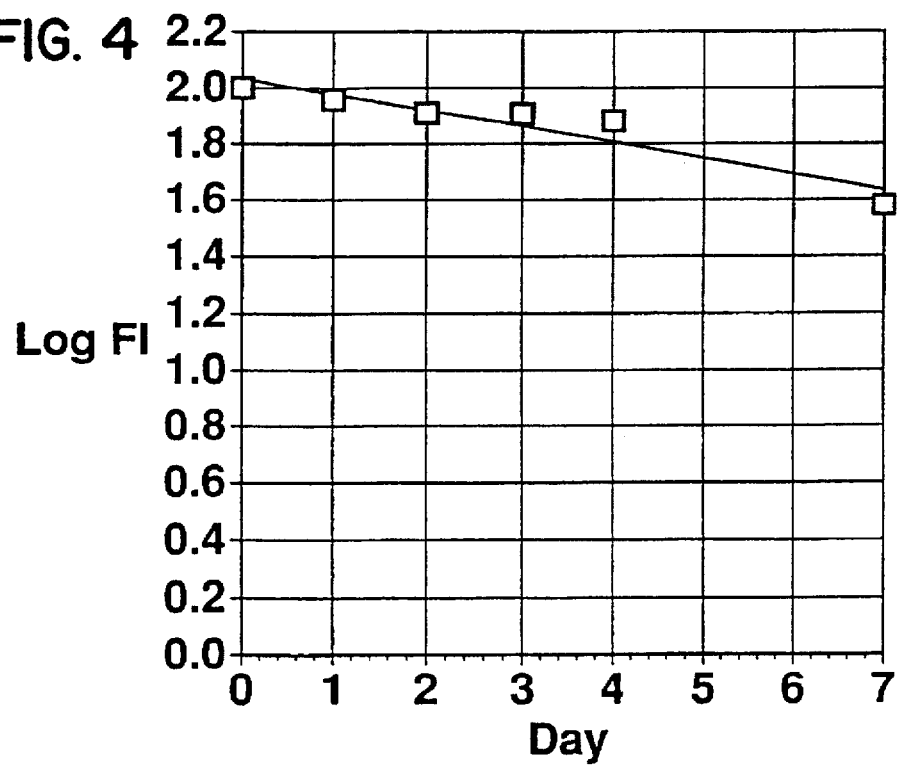
FIG. 4 is a graph representing the in vivo binding stability of a Substance P-lipophilic cyanine dye conjugate of the invention to red blood cells, determined as a function of time.

The results of this study are represented in the graph of FIG. 4, from which it can be seen that in vivo dissociation of the conjugate from labeled cells occurred relatively slowly. The fluorescence (log fluorescence intensity) associated with the labeled cells decreased with a half-life of 5–6 days, as compared with a lifetime in circulation of minutes for native Substance P.

From the foregoing experimental results, it thus appears that labelling of bio-particles with a lipophilic molecule bearing a therapeutic agent offers an innovative delivery vehicle for parenteral administration of therapeutic agents.

EXAMPLE 7

Effect of Iodination on Dye Incorporation, Cell Viability and Membrane Binding Stability To verify that addition of an iodine atom to compounds of the invention did not substantially affect their cell labeling properties, in vitro determinations of compound uptake, cell viability post-labeling and membrane retention were carried out for the following compounds:

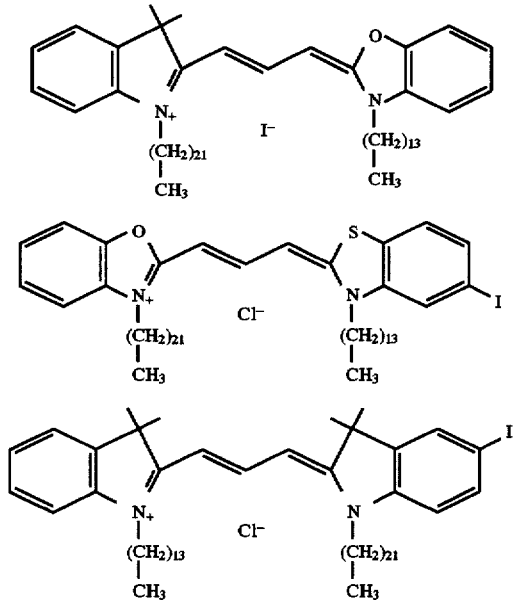

Compounds, T, AA and AB can be prepared according to the general procedures set forth in foregoing Rreaction scheme 1 and described in Example 3 above.

Recovery and viability (calculated as described in Slezak and Horan, Blood, 74: 2172–2177 (1989)) at 5, 10 and 20 µM labeling concentrations and for 5 or 10 µM for compounds AA and AB. However, viability and recovery decreased to 70–80% for compounds AA and AB at 20 µM labeling concentrations.

Number of molecules of compound incorporated per cell was determined for cells labeled with 10 µM compounds. An aliquot of $10^6$ cells (10 ul) was withdrawn from the washed cells after final resuspension and counting, compounds were extracted from the cell membrane by admixture with 250 µl of 100% ethanol, and the fluorescence intensity of 200 µl of the extract was measured using a Fluoroskan II fluorescence microplate reader and filter combination. Concentration of compound in each extract was determined from a calibration curve of known compound concentrations made up in 100% ethanol and measured on the Fluoroskan II. Number of molecules of compound per cell was then calculated from the known extract concentration, total volume of extract, and known number of cells extracted. Calculated values were $(4.0\pm0.4)\times10^6$ for compound T $(1.3\pm0.2)\times10^6$ for compound AA and $(2.5\pm0.7)\times10^6$ for compound AB.

Relative membrane retention was determined using erythrocyte membrane ghosts prepared by $NH_4Cl$ lysis (Slezak and Horan, Blood, supra). Ghosts were labeled at $4\times10^8$/ml with 10 µM compounds for 5 minutes at room temperature, using previously described procedures. However, post-labeling washes were carried out using PBS containing 1 mM EDTA and 5% BSA. After the final wash, ghosts were resuspended at $4\times10^8$/ml in PBS+EDTA+5% BSA and incubated for 24 hours at 37° C. At 24 hours, duplicate 50 µl aliquots were withdrawn from a) the well mixed suspension of ghosts (for determination of total compound present), and b) the supernatant remaining after ghosts were pelleted for 15 minutes at 12,500×g (for determination of unbound compound present). Aliquots were extracted by admixture with 200 µl of 100% ethanol and fluorescence intensity of each extract measured using the Fluoroskan II fluorescence microplate reader. Percent compound retained was calculated as total compound—unbound compound×100/total compound Calculated values were found to be (91.9±2.9)% for compound T (97.7±)0.2)% for compound AA and (96.8±1.3)% for compound AB.

Based on the foregoing experiments, it was concluded that iodinated compounds of the invention exhibited membrane retention characteristics equal or superior to the non-iodinated compound. Although their incorporation into red cell membranes was somewhat lower, as compared with equivalent concentrations of non-iodinated compound, as might be predicted on the basis of their larger molecular size and weight, it is not expected that this difference would be sufficient to alter their utility for cell labeling applications of the type described above.

EXAMPLE 8

Retention on Artificial Surfaces

Figure 5:
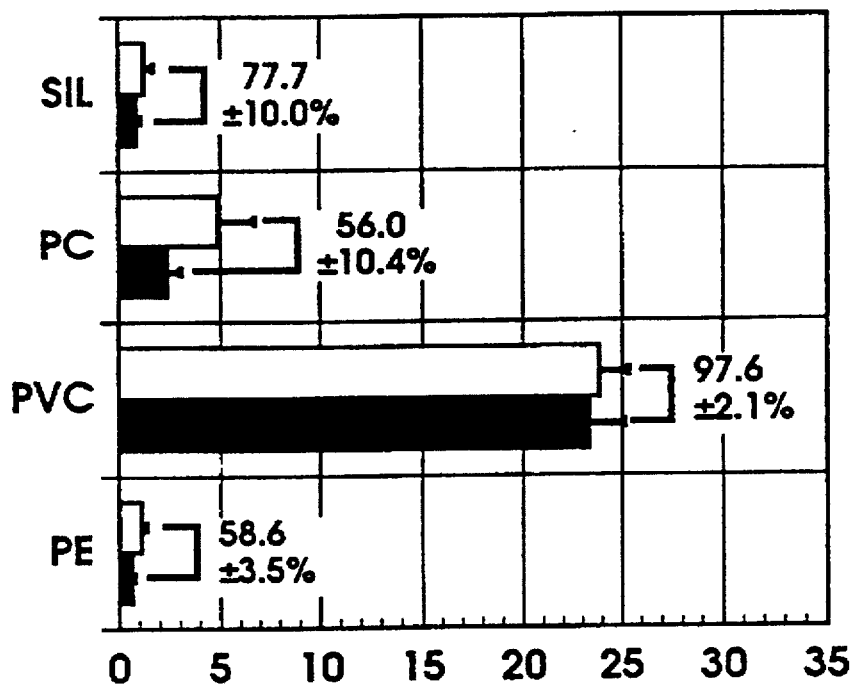
FIG. 5 is a bar graph representation of the degree of retention of radioiodinated ($^{125}$I) lipophilic cyanine on four different types of artificial surfaces; silastic rubber (SIL), polycarbonate (PC), polyvinylchloride (PVC) and polyethylene (PE). Stippled bars represent the amount of radiiodinated ($^{125}$I) lipophilic cyanine bound initially to each surface; solid bars represent the amount remaining after 6 hours of continuous blood perfusion. Values associated with paired bars are the percentages retained of the initial amount of compound bound.

To assess the ability of the compounds of invention to be retained on artificial surfaces, a solution of a radioiodinated ($^{125}$I) lipophilic cyanine, (compound 12, Reaction Scheme 2, Example 3g., above) in 100% ethanol, was placed in contact with the lumenal surface of short sections of several different types of plastic tubing, including medical silastic (SIL), polycarbonate (PC), polyvinylchloride (PVC) and polyethylene (PE). The compound was allowed to remain in contact with the tubing for 10 minutes and then removed and the tubing gently flushed with PBS. After making baseline radioactivity measurements of the labeled tubing, the sections were connected with a longer, closed loop tubing circuit containing approximately 30 ml of fresh, anticoagulated human blood. The tubing circuit was passed through a roller pump and the blood was circulated for a period of 6 hours. At the end of 6 hours, the tubing sections were disconnected, flushed gently with PBS to eliminate any adherent blood and counted for radioactivity. The results of this experiment are graphically represented in FIG. 5. Tubing section length, diameter, and the specific activity of the radioiodinated compound of invention were recorded so that the data could be expressed as picograms of radiiodinated compound/mm$^2$ of tubing lumen surface (x-axis of bar graph). FIG. 5 shows that PVC tubing initially bound the greatest amount of the radioiodinated compound while PE bound the least. Highest retention on the tubing after 6 hours in contact with blood occurred with PVC (97.6±2.1% of initial radioactivity retained) while retention was poorest with PC (56.0±10.4% of initial radioactivity retained). However, average retention was in excess of 50% for all tubing and approached 100% for PVC, demonstrating an ability of the compound of the invention to remain on artificial surfaces for prolonged periods despite contact with biological fluids. The compounds of invention may, therefore, be useful in the retention of biopassivating substances on artificial surfaces.

EXAMPLE 9

In Vivo Retention of a $^{186}$Re-Chelator Lipophilic Cyanine Conjugate vs. Na$^{186}$ReO$_4$ After Intratumor Injection The $^{186}$Re-chelator lipophilic cyanine conjugate was prepared essentially by the method described in Example 3h (Compound 24 of Reaction Scheme 5), except that the SepPak was washed with approximately 10 mL distilled water prior to elution of product with ethanol, to remove excess gentisic acid and avoid the need for pH adjustment prior to in vivo administration. After vacuum evaporation, the concentrated stock solution brought to a final volume of approximately 25 µL in ethyl alcohol (compound 24 concentration approximately 500 µM; specific activity approximately 123 mCi/µmole). Preparations of compound 24 and Na$^{186}$ReO$^4$ for in vivo injection containing approximately 5–6 µCi of $^{186}$Re were made as follows. Na$^{186}$ReO$_4$ (NEZ301, in 0.1N NaOH) was diluted in sterile 300 mOsM Dulbecco's phosphate buffered saline, the pH was verified to be 7.0 using pH paper, and the preparation was then re-sterilized by passing it through a 0.22 µm filter. Compound 24 was diluted in sterile 300 mOsM glucose. Sterile 50 µL Hamilton syringes were loaded with 5.0 µL of the Na$^{186}$ReO$_4$ or compound 24 preparations using sterile technique. Separate aliquots were also taken to provide counting standards for each preparation and to serve as reference samples for decay correction of whole body images and biodistribution measurements.

Retention of the above described preparations after intratumor injection was evaluated as follows. Five to six days prior to intratumor injection, growth of MC38 adenocarcinoma nodules was initiated by intradermal injection on the right hind limb of female C57B1/6 mice using an innoculum of approximately 1×10$^6$ live tumor cells suspended in sterile Hanks' buffered salt solution. On day 0, animals were reanesthetized, the right hind limb was sterilized using an alcohol swab and 5.0 µL aliquots of compound 24 or Na$^{186}$ReO$_4$ were injected directly into tumor nodules approximately 5 mm in diameter. Injections were made over a period of approximately 10 seconds and the needle was held in place for an additional 5–10 seconds after the injection was completed to allow dissipation of any backpressure and minimize leakage at the injection site. Animals and counting standards were imaged using a GE Starcam 300 system immediately after injection (within 10–15 minutes) and daily thereafter for 4 days, using an energy window of 140±20 keV. After imaging was completed on days 2 and 4, groups of animals were sacrificed and various organs were collected, weighed, and cpm/gm determined for evaluation of biodistribution of $^{186}$Re.

Distribution of $^{186}$Re in selected organs at day 4 is shown in Table IV A. Results are expressed as % of total counts injected recovered in the specified organ after correction for decay. Since organs and tumor differed significantly in size, the relative concentration of $^{186}$Re found in each organ is compared in Table IV B. Results are expressed as the percentage of injected counts that would be found in a 1 gram block of tissue after correction for decay. Whole body scintigraphic images were analyzed by establishing regions of interest (ROI) corresponding to Tumor or Whole Body; counts in each region of interest were then determined as a function of time after injection. Localization of label in tumor was calculated as ratio of counts in Tumor ROI to counts in Whole Body ROI (columns 2 and 3, Table V). Percent retention of label within the body was calculated as the ratio of counts in Whole Body ROI to counts in Reference ROI (columns 4 and 5, Table 2).

The data of Tables IV and V indicate that degree of leakage of $^{186}$Re away from the intratumor injection site is greatly decreased by administration of the radionuclide in the form of compound 24. These data also indicate that good agreement is obtained using two different methods (whole body gamma scintigraphy and direct excision) to measure intra-tumor retention.

TABLE IV

Biodistribution of $^{186}$Re on Days 2 and 4 after Intra-tumor Injection[1]

| Time Post-Injection | Day 2 | | Day 4 | |
|---|---|---|---|---|
| ORGAN | Na$^{186}$ReO$_4$ | $^{186}$Re-PKH113 | Na$^{186}$ReO$_4$ | $^{186}$Re-PKH113 |
| A. PERCENT OF INJECTED COUNTS IN ORGAN | | | | |
| tumor | .07 ± .10 | 57 ± 13 | 0.16 ± 0.08 | 57 ± 5 |
| liver | .002 ± .001 | 1.4 ± 0.3 | .004 ± .002 | 0.7 ± 0.3 |
| spleen | 0 ± 0 | 0.4 ± 0.4 | .011 ± .003 | 0.08 ± 0.06 |
| stomach | .014 ± .003 | 0.5 ± 0.5 | .005 ± .001 | 0.3 ± 0.2 |
| intestine | .005 ± .0006 | 0.3 ± 0.1 | 0.06 ± 0.05 | 0.06 ± 0.05 |
| kidney | .001 ± 0 | .03 ± .02 | 0.04 ± 0.01 | 0.04 ± 0.05 |
| B. PERCENT OF INJECTED DOSE PER GRAM OF TISSUE | | | | |
| tumor | 0.7 ± 1.0 | 450 ± 160 | 1.6 ± 0.7 | 290 ± 70 |
| liver | .002 ± .0005 | 1.6 ± 0.6 | .007 ± .004 | 0.7 ± 0.3 |
| spleen | .005 ± .002 | 6.2 ± 5.7 | 0.02 ± 0.02 | 0.8 ± 0.6 |

[1]mean ± standard deviation, n = 3 per group except n = 2 for $^{186}$Re-PKH113 group on day 2

TABLE V

Retention of $^{186}$Re in Tumor after Intra-tumor Injection

| time post-injection | Percent of injected counts[1] retained in tumor | | Percent of injected counts[1] Counts remaining in body | |
|---|---|---|---|---|
| | Na$^{186}$ReO$_4$[2] | $^{186}$Re-PKH113[3] | Na$^{186}$ReO$_4$[2] | $^{186}$Re-PKH113[3] |
| 15 min. | 35 ± 11% | 89 ± 7% | 96 ± 2% | 97 ± 7% |
| 1 day | .8 ± .4% | 71 ± 12% | 3 ± 1% | 78 ± 11% |
| 2 days | .7 ± .7% | 68 ± 11% | 3 ± 1% | 76 ± 11% |
| 3 days | .5 ± .5% | 69 ± 3% | 3 ± 2% | 80 ± 3% |
| 4 days | 1.5 ± .9% | 65 ± 6% | 4 ± 1% | 74 ± 5% |

[1]Mean ± standard deviation (differences of <5% not statistically different from 0)
[2]n = 6 on days 0–2, n = 3 on days 3–4
[3]n = 5 an days 0–2, n = 3 on days 3–4

EXAMPLE 10

In Vivo Retention of a $^{186}$Re-Chelator Lipophilic Cyanine Conjugate vs. Na$^{186}$ReO$_4$ After Intra-Articular Injection Two properties of compounds of the invention, in addition to their therapeutic efficacy, are important in achieving site-selective administration and retention:

a) the level of retention at the site of application when compared with unlinked therapeutic agents; and b) the pattern (heterogeneous vs. homogeneous) of their distribution after injection at a site.

Using fluorescent or radiolabeled compounds, these properties have been assessed on the basis of delivery of rhenium-containing compounds to the synovial lining of a joint cavity.

The $^{186}$Re-chelator lipophilic cyanine conjugate (compound 24 of Reaction Scheme 5) was prepared as described in Example 3h. and the concentrated stock solution brought to a final volume of approximately 40 μL in ethyl alcohol. Preparations of compound 24 and Na$^{186}$ReO$_4$ for in vivo injection were made as follows. Na$^{186}$ReO$_4$ (NEZ301, in 0.1N NaOH) was diluted in sterile 300 mOsM Dulbecco's phosphate buffered saline, the pH was verified to be 7.0 using pH paper, and the preparation was then re-sterilized by passing it through a 0.22 μm filter. Compound 24 was diluted in sterile 300 mOsM glucose and the pH was adjusted to 7.0 by addition of sterile 0.1N NaOH (necessitated by the fact that no buffer was present in the glucose diluent and that gentisic acid present in the final preparation resulted in an unadjusted pH of 1–2). Sterile 1.0 mL tuberculin syringes with 25G×⅝ in. needles were weighed, loaded with approximately 0.1 mL of the Na$^{186}$ReO$_4$ or compound 24 preparations using sterile technique, and reweighed to determine preinjection weight. Aliquots were also taken to determine cpm/μL for each preparation.

Retention of the above described preparations after intra-articular injection was evaluated as follows. Female New Zealand White rabbits weighing 3–4 kg were anesthesized with ketamine and xylazine, and the knee region was carefully shaved and swabbed with iodine solution. Using sterile technique, the knee was flexed to approximately 120°, the kneecap was temporarily laterally displaced, the needle was inserted medially through the skin into the articular space, approximately 0.1 mL of compound 24 (3 animals) or Na$^{186}$ReO$_4$ (2 animals) preparation was injected, the needle was withdrawn, and the kneecap was returned to its normal position. The exact volume and activity of compound 24 or Na$^{186}$ReO$_4$ injected was determined by reweighing the syringe, calculating the difference between pre- and post-injection weights, (assuming a density of 1.0 g/mL for the injectate) and multiplying the measured volume in μL by the value of cpm/μL obtained by counting aliquots of known volume of each preparation. Within 5–10 minutes after intra-articular injection, a known volume of blood (approximately 1 mL) was withdrawn from the central ear artery. Animals were then placed in cages which enabled separate collection of urine and feces and monitored for 6 days. Each day, blood was drawn, all urine excreted in the previous 24 hour period was collected, and cpm/mL were determined for aliquots of known volume of blood and urine using a Packard Cobra Model 5003 gamma counter. Total blood borne counts were estimated based on a blood volume of 5.5% of total body weight and cpm/mL of blood; total urinary counts were calculated based on 24 hour urine volume and cpm/mL of urine. No significant counts were detected in feces. On days 0, 1, 4, and 6, gamma scintigraphy was carried out using a GE Starcam 300 system with an energy window of approximately 120–150 kEV. On day 6, after collection of blood and urine samples, animals were sacrificed and various organs were collected, weighed, and cpm/gm determined for evaluation of biodistribution of $^{186}$Re.

Circulating levels of compound 24 and Na$^{186}$ReO$_4$ in blood and amounts excreted in urine over the 6 day post-injection period are shown in Table VI. Distribution of $^{186}$Re in selected organs at day 6 is shown in Table VII. All results in Tables VI and VII are expressed as % of counts injected after correction for decay. The data of Tables VI and VII indicate that degree of leakage of $^{186}$Re from the intra-articular space as measured by blood levels, urinary excretion and accumulation in other organs, is greatly decreased by administration of the radionuclide in the form of compound 24. Retention in the knee was further evaluated by determining counts in specific regions of interest (knee and/or whole body) from gamma scintigraphy images, as shown in Table VIII. These results also indicate greatly improved retention when radionuclide is administered in the form of compound 24.

TABLE VI

Levels of $^{186}$Re in Blood and Urine after Intra-articular Injection

| Days post-injection | Percent of injected counts in | | | |
|---|---|---|---|---|
| | Blood | | Urine | |
| | Na$^{186}$ReO$_4$ | $^{186}$Re-Cpd. 24[1] | Na$^{186}$ReO$_4$ | $^{186}$Re-Cpd. 24 |
| 0 | 21 ± 5 | 0.35 ± .06 | NA[2] | NA |
| 1 | .048 ± .020 | 0.093 ± .047 | 75 ± 6 | 3.1 ± 1.7 |
| 2 | .006 ± .009 | 0.12 ± .039 | 9.9 ± .15 | 2.2 ± 0.31 |
| 3 | .004 ± .006 | 0.21 ± .022 | .67 ± .36 | 2.1 ± 0.51 |
| 4 | .006 ± .008 | 0.12 ± .023 | .70 ± .12 | 1.6 ± 0.50 |
| 5 | 0 ± 0 | 0.25 ± 0.13 | .17 ± .07 | 2.5 ± 0.63 |
| 6 | .002 ± .002 | 0.19 ± 0.071 | .28 ± .22 | 2.6 ± 0.79 |
| 0 through 6 | NA | NA | 87 ± 5 | 14 ± 2.0 |

[1]prepared as in Example 3h., above
[2]not applicable

TABLE VII

Biodistribution of $^{186}$Re on Day 6 After Intra-articular Injection

| | Percent of injected counts | |
|---|---|---|
| Organ | Na$^{186}$ReO$_4$ | $^{186}$Re-Cpd.24 |
| Liver | .0005 ± .0007 | 0.16 ± .073 |
| muscle | 0 ± 0 | .023 ± .025 |
| kidney | 0 ± 0 | .070 ± .010 |
| blood | .0015 ± .0021 | .190 ± .070 |
| bone marrow | 0 ± 0 | .027 ± .012 |
| other organs[1] | 0 ± 0 | .023 ± .012 |

[1]sum of lung, heart, spleen, gall bladder, thyroid, and lymph nodes

TABLE VIII

Retention of $^{186}$Re in Knee after Intra-articular Injection

| Time Post-Injection | Fraction of whole body counts[1] present in the knee | | Fraction of day 0 counts[1] remaining in the knee | |
|---|---|---|---|---|
| | Na$^{186}$RePO$^4$ | $^{186}$Re-Cpd.24 | Na$^{186}$ReO$_4$ | $^{186}$Re-Cpd.24 |
| 30 min. | 11% | 96 ± 2% | 100% | 100 ± 0% |
| 1 day | <5% | 103 ± 3% | <5% | 98 ± 1% |
| 4 days | <5% | 108 ± 2% | <5% | 83 ± 11% |
| 6 days | <5% | 114 ± 4% | <5% | 68 ± 2% |

[1]Decay corrected values; differences of <5% not statistically diferent from 0

EXAMPLE 11

Synovial Distribution of Lipophilic Cyanine Conjugates After Intra-articular Infection To estimate the homogeneity or heterogeneity of incorporation by synovial cells after intra-articular injection, approximately 0.1 mL of a 10 μM solution of an iodide salt of compound T (see Example 2, above) in 300 mOsM pH 7.0 glucose was injected into the knee as described in Example 10. After 1 hour, the animal was sacrificed, and both injected and uninjected knee joints were dissected. Preparation of whole joint cross sections was not feasible because demineralization is required to cut thin sections and demineralizing solvents remove compounds of the invention from tissue. Therefore the infrapatellar fat pads which underlie the kneecap and form one boundary of the synovial cavity were carefully removed, snap frozen on dry ice, and stored at −80° until frozen sections could be prepared. Thick (10μ) cryostat sections were cut, adhered to glass slide, and evaluated by light and fluorescence microscopy.

Light micrographs of fat pad cross sections (injected or uninjected knee) showed synovial cells lining the surface of the fat pad facing into the joint space as a thin dark line along the inner edge of the section when viewed at 100x magnification. (The synovial layer is only 1–2 cells thick in a normal joint but becomes thickened due to hyperproliferation in an arthritic joint.) The rest of the tissue was composed primarily of large fat cells. Illumination of cross sections from the injected knee with blue exciting light demonstrated the presence of bright and relatively homogeneous labeling was essentially confined to the synovial cell layer, while the fat cell region or cross sections from the uninjected knee exhibited only much dimmer green autofluorescence.

EXAMPLE 12

Retention of Lipophilic Cyanine Conjugates at Intravascular Site

To determine whether the compounds of the invention will remain at an intravascular site once applied experiments were performed wherein $^{125}$I-substituted lipophilic cyanine, prepared as described in Example 2 (compound 12, Reaction Scheme 2) was applied to the lumenal surface of the femoral arteries of anesthetized rabbits. The femoral artery was surgically isolated and a small, proximal side branch was cannulated with a short length of PE10 tubing. A 1 cm arterial segment surrounding the side branch was occluded and 20–50μl of a solution containing $^{125}$I-substituted compound 12 was administered through the cannula to the occluded section and allowed to remain for 5–10 min. The $^{125}$I-substituted compound was then withdrawn along with the cannula, the side branch was permanently tied, the femoral artery occlusion removed to allow the return of blood flow, and the femoral incision was closed. $^{125}$I-radioactivity was then monitored at selected times over the next 3 weeks with a Ludium Model 2200 Scaler Ratemeter and a Model 44–17 2 inch crystal with windows optimized for the detection of $^{125}$I.

Graphic analysis of the resultant data suggested a 2-phase elimination process wherein 34.0±10.9% (mean±sem, n=4) of the applied material (radioactivity) remained within the artery after the first 24 hour with an initial elimination half-life of 0.77±0.29 days. After the first 24 hours, however, the remaining material was eliminated very slowly, with an elimination half-life of 15.24±2.89 days. Thus, significant amounts of the $^{125}$I-substituted compound could be detected for at least 3 weeks after application due to slow elimination from the intravascular application site.

EXAMPLE 13

Antiproliferative Activity of Cholicine Lipophilic Cyanine Conjugate on A10 Cells In Vitro To determine the antiproliferative action of the compounds of invention, in vitro studies were performed using A10 cells, a clonal cell line originally derived from the thoracic aorta of embryonic rats, that proliferate as myoblasts and develop into cells which phenotypically resemble smooth muscle cells (B. Kimes and B. Brandt, Exptl. Cell Res. 98:349 (1976). Typically, twelve-well plates were seeded with 2500–10,000 A10 cells/cm$^2$ in Dulbecco's Modified Eagles Medium (DMEM) with 10% fetal calf serum (FCS) and allowed to adhere and stabilize for 24 hours at 37° C. Test substances were then prepared in the required concentrations in appropriate cell binding media and, after aspirating the plating medium, applied to the individual wells at 37° C. for a period of only 10 minutes. The treatments were then aspirated, the wells washed 4 times with non-treatment containing medium and then placed in non-treatment containing DMEM with 10% FCS for the duration of the study. At various times after treatment application, triplicate wells were aspirated, the aspirate saved, and the wells treated with 0.25 ml of 0.25% trypsin to release the adherent cells. The enzymatic action of trypsin on the cells was stopped by addition of excess protein (1.75 ml DMEM+10% FCS), the aspirate returned to the wells, and an aliquot of the resultant cell suspension counted in a Coulter Counter (Model ZM with Sampling Stand II). Cell count was normalized to cells per square centimeter of growing area (surface area of well bottom).

As shown in Table IX below, after 7 days, proliferation in cell cultures treated with a compound of the invention (compound 19, Reaction Scheme 3, Example 3i., referred to herein as "colchicine conjugate") demonstrated only 5.2% of the vehicle-treated growth maximum. There was significant cell-associated fluorescence (measured by flow cytometry), demonstrating the persistence of binding of the colchicine conjugate to A10 cells. Conversely, cells treated with the same initial concentration of unconjugated colchicine were present at only one-half the cell density of vehicle-treated cells, an increase in cell number of approximately 10-fold over that obtained with the compound of invention. Thus the compound of invention permitted significant retention of the antiproliferative activity of the parent compound in A10 cells despite an exposure of only 10 minutes, and showed much greater antiproliferative effect than unconjugated colchicine applied in the same manner.

Example 3a.) (2) anticoagulant-lipophilic cyanine conjugate (compound 21, Reaction Scheme 4, Example 3j.), or (3) fluorescein isothiocynate-labeled heparin (FITC-heparin) at concentrations of 10 µM, 20 µM, and 20 µM, respectively. Ghosts were then washed extensively and placed in phosphate buffered saline with 1mM EDTA and 5% BSA for 24 h at 37° C. Samples were agitated and a 50 µl aliquot removed from each sample and placed in 200 µl of Triton X-100® in a microtiter plate well (representing total suspension fluorescence). The original samples were centrifuged for 10 minutes and a 50 µl sample of the ghost supernatant removed and placed in 200 µl of Triton X-100® (representing free fluorescence in the aqueous phase only). The fluorescence of all samples was determined on a fluorometric microtiter plate reader. Bound fluorescence was determined by subtraction of free from total after correction for background fluorescence from unstained ghosts; the percent free and bound fluorescence was determined by dividing the bound and free fluorescence by total fluorescence, respectively and multiplying by 100.

The results, presented in Table X below demonstrate that the anticoagulant conjugate of invention exhibited good membrane retention with 90.94% of fluorescence being associated with ghost membrane after 24 hours, compared with 94.96% retention with the compound of invention not containing anticoagulant. FITC-heparin showed only poor retention with only 37.63% of fluorescence remaining after 24 hours. This value is most likely an overestimate of the true retention of FITC-heparin inasmuch as the fluorescence signal of FITC-heparin on ghosts was only slightly above background fluorescence levels, and the calculation of percent bound and free from these values is of questionable precision. The data below clearly show, however, that the compound of invention is well retained on biological membranes, whereas fluorescent heparin is not.

TABLE X

Comparison of the antiproliferative action of colchicine and Colchicine Conjugate after one 10 minute application

| Day | 0 | 1 | 2 | 3 | 6 | 7 |
|---|---|---|---|---|---|---|
| Vehicle[1] | 2202.35 ±223.87 | 5591.38 ±307.20 | 15620.10 ±1280.58 | 30659.27 ±3081.07 | 182704.96 ±7303.67 | 208544.39 ±812.53 |
| Colchicine (10 µM) | 3006.53 ±181.63 | 3778.07 ±235.12 | 4249.35[2] ±548.60 | 7785.90[2] ±238.90 | 57626.63[3] ±2412.23 | 118127.94[2] ±103.87 |
| % of Vehicle Maximum | 1.44 | 1.81 | 2.04 | 3.73 | 27.63 | 56.64 |
| Colchicine derivative (10 µm) | 2291.12 ±270.47 | 2625.33 ±293.34 | 2369.45[2] ±227.77 | 2206.27[2] ±209.07 | 8800.26[2,3] ±1498.63 | 10895.65[2,3] ±25.55 |
| % of Vehicle Maximum | 1.10 | 1.26 | 1.14 | 1.06 | 4.22 | 5.22 |

[1]Values are mean ± sem, n = 3 replicates
[2]p < 0.05 from Vehicle group
[3]p < 0.05 from Colchicine group

EXAMPLE 14

Binding of an Anticoagulant Lipophilic Cyanine Conjugate to Biological Membranes To assess whether the anticoagulant compounds of the invention could bind stably to biological membranes, in vitro studies were performed in rabbit red blood cell ghosts as described in Example 1, above. 2×10$^8$ ghosts/ml were labeled with either (1) derivatized lipophilic cyanine not containing anticoagulant (compound 7, Reaction Scheme 1,

TABLE X

| | Fluorescence Intensity | | | |
|---|---|---|---|---|
| | Suspension | Supernatant | % Free | % Bound |
| Compound 7 | 1439.00 | 73.69 | 5.04 | 94.96 |
| | ±33.55 | ±2.53 | ±0.06 | ±0.06 |
| Unstained | 1.68 | 1.24 | | |
| Heparin- | 191.40 | 18.36 | 9.06 | 90.94 |
| Conjugate | ±6.07 | ±0.53 | ±0.04 | ±0.04 |
| Unstained | 1.64 | 1.166 | | |
| FITC Heparin | 0.599 | 0.517 | 62.37 | 37.63 |
| | ±0.005 | ±0.011 | ±1.29 | ±1.29 |
| Unstained | 0.463 | 0.465 | | |

*Values for fluorescent compounds are given as mean ± sem, n = 3 replicates.

EXAMPLE 15

Figure 6:
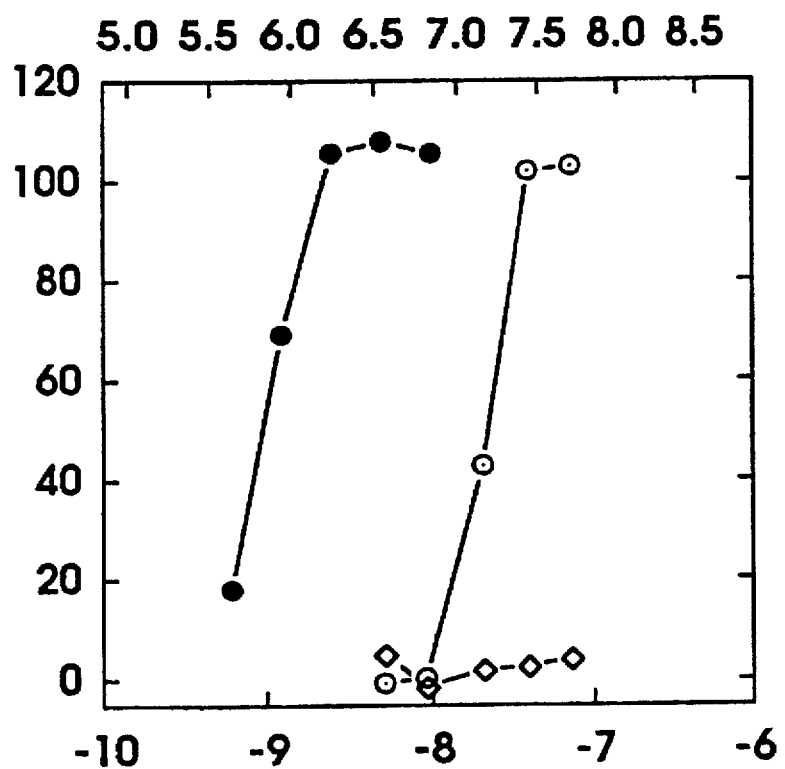
FIG. 6 shows data from an experiment wherein carrier cells labeled with anti-coagulant lipophilic cyanine conjugate were tested for ability to inhibit the in vitro generation of fibrin produced by a standard concentration of thrombin. The concentration response for unconjugated anti-coagulant is provided for comparison. Percentage inhibition of thrombin response (y-axis) is recorded as a function of the molar concentration of compound tested (lower x-axis; log scale), and of the number of carrier cells per test sample (upper x-axis; log scale).

Retention of Anticoagulant Properties of Anticoagulant-Lipophilic Cyanine Conjugate When Bound to the Surface of Biological Membranes To determine whether the anticoagulative properties of the compounds of the invention were retained when coated on the surface of biomembranes, in vitro studies were performed to assess the ability of the compound of invention to inhibit the coagulation enzyme, thrombin. Rabbit red blood cell ghosts were first labeled with 10 µM of an anticoagulant-lipophilic cyanine conjugate (compound 21, Reaction Scheme 4, Example 3j.), washed 4x in PBS with 0.1% BSA and then diluted to various numbers of ghosts/ml. Concentration of compound 21 on ghosts was assessed by placing known numbers of ghosts in microtiter plate wells and comparing the observed fluorescence to the fluorescence produced by known standard concentrations of the compound. Activity assays were then performed in a manner similar to that reported by Krstenansky and Mao, FEBS Let. 211:10 (1987), wherein 100 µl a 1:10 dilution of human plasma in phosphate buffered saline (PBS) buffer, 50 µl of PBS containing varying concentrations of labeled ghosts or standard thrombin inhibitor, and 50 µl of PBS containing a constant amount (0.5 nM) of thrombin were added to microtiter plate wells and absorbance changes at 405 nm were recorded in a spectrophotometric plate reader (Bio-Tek) over a 60 minute period. Samples were run in triplicate and then averaged. The absorbance changes over time data were plotted and area-under-the-curve measurements performed by computer. Data from inhibitor-treated wells were expressed as the percent inhibition of the absorbance area obtained in the absence of inhibitor. Data from a typical experiment are presented in FIG. 6. $EC_{50}$ values of 1.03 nM and 21.23 nM (@$1.43\times10^7$ ghosts/200 ul) obtained by 3 parameter nonlinear logistic regression for heparin (●) and the anticoagulant conjugate of the invention (○), respectively, demonstrate that, when applied to biomembranes, the compound of the invention is some 20-fold less potent as a thrombin inhibitor than the parent compound. This inhibitory activity is all membrane associated, however, inasmuch as concurrently assayed samples of serially diluted ghost-free supernatants (◊) had no thrombin inhibitory activity. Thus, the compound of the invention still retains potent antithrombin action even when bound to biomembranes.

Various aspects of the present invention have been described and exemplified above in terms of certain preferred embodiments, namely, the synthesis and use of chemotherapeutic and radiotherapeutic antiproliferative compounds. However many other embodiments may be apparent to those skilled in the art. For example, other chemotherapeutic and radiotherapeutic conjugates may be synthesized and used for treatment or assessment of a variety of disease states or pathological conditions. Additionally, the compounds and methods of the invention may be applied to the development of site-selective delivery and retention of drugs of other classes, such as anti-bacterial, anti-fungal or anti-inflammatory agents. This invention, therefore, is not limited to the embodiments specifically described and exemplified, but is capable of variation and modification without departure from the scope of the following claims.

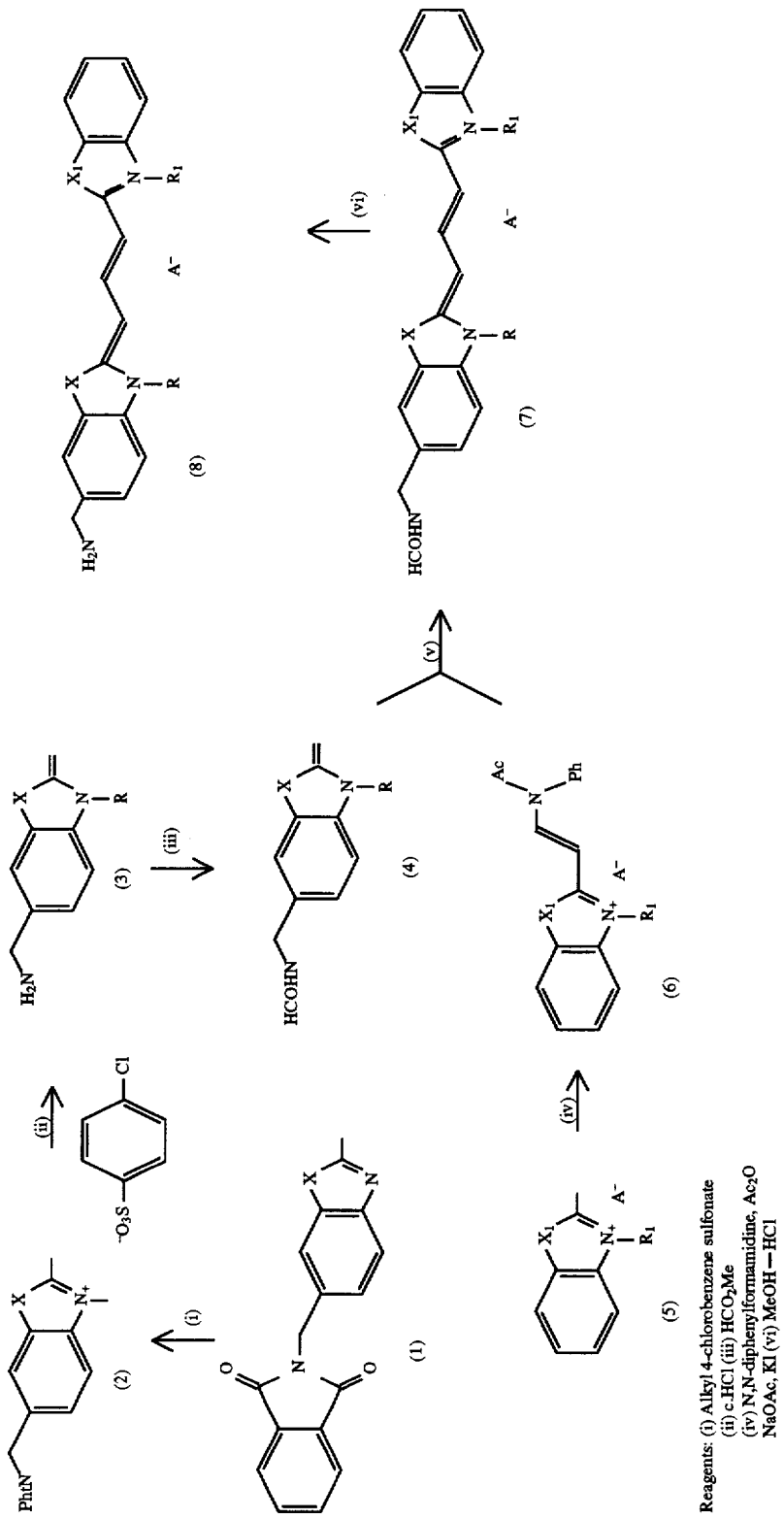
SCHEME 1
Reagents: (i) Alkyl 4-chlorobenzene sulfonate
(ii) c.HCl (iii) HCO₂Me
(iv) N,N-diphenylformamidine, Ac₂O
NaOAc, KI (vi) MeOH—HCl

SCHEME 2
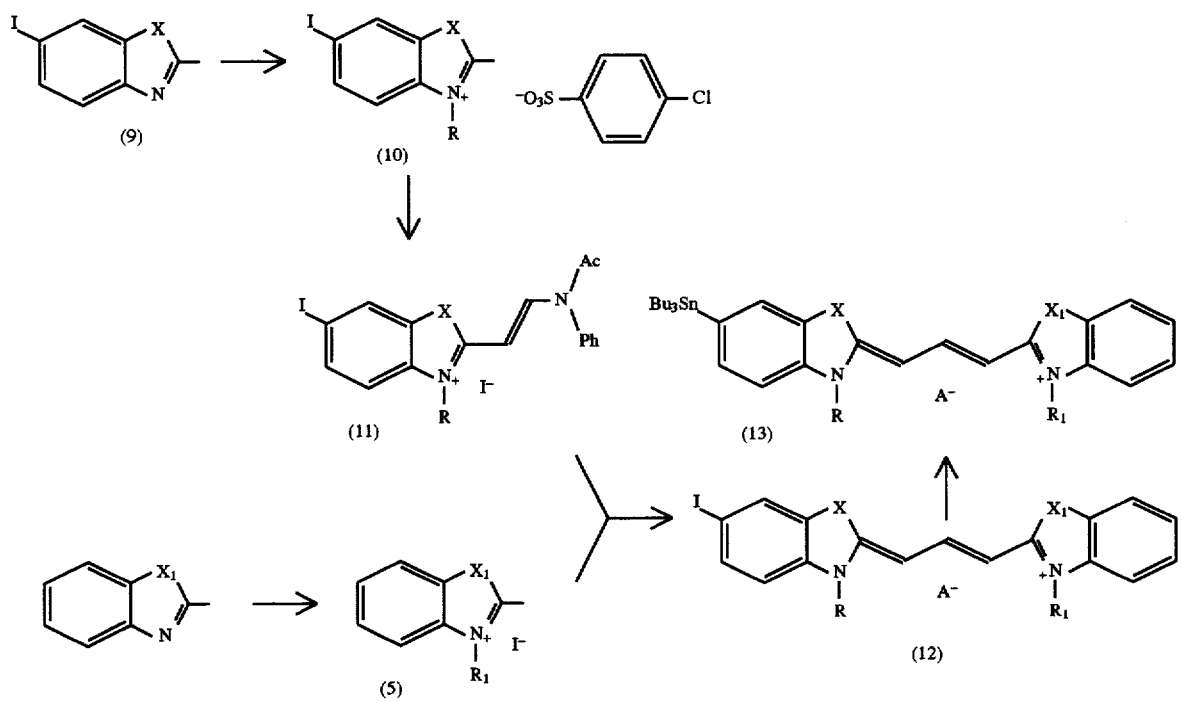
SCHEME 3
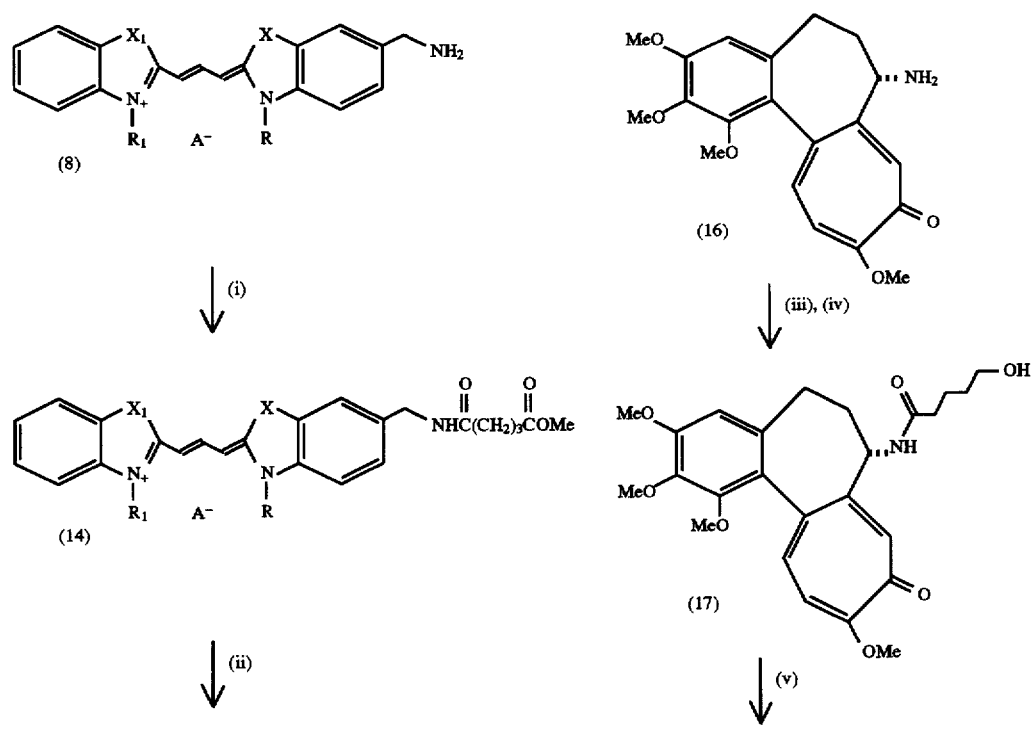

-continued
SCHEME 3
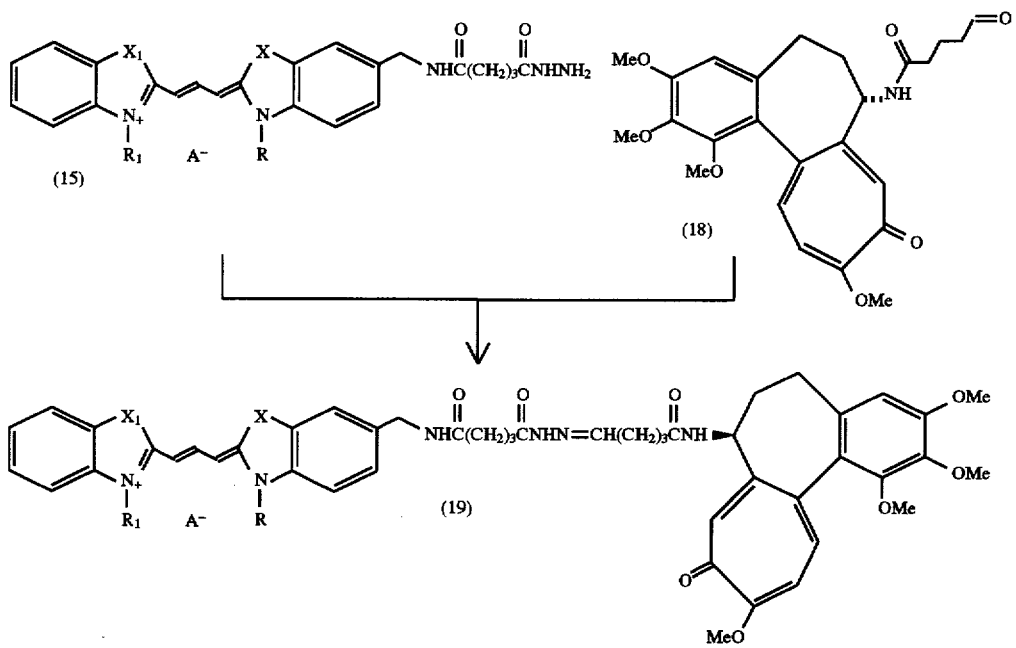
REAGENTS: (i) GLUTARIC ACID MONOMETHYL ESTER, DCC, NHS
(ii) HYDRAZINE (iii) GLUTARIC ANHYDRIDE
(iv) CDi THEN Bu₄NBH₄ (v) PCC
SCHEME 4
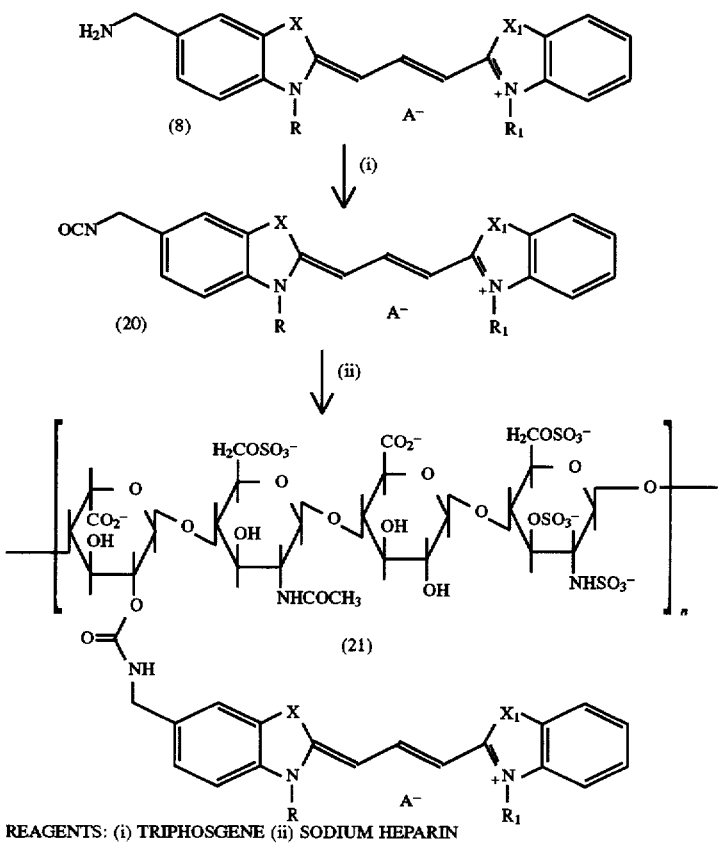
REAGENTS: (i) TRIPHOSGENE (ii) SODIUM HEPARIN SCHEME 5
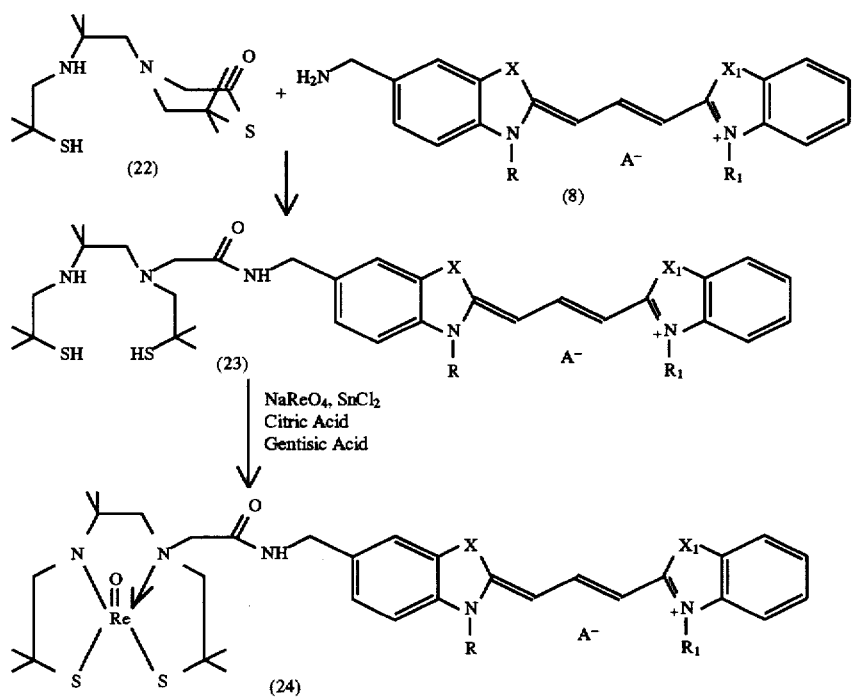
SCHEME 6
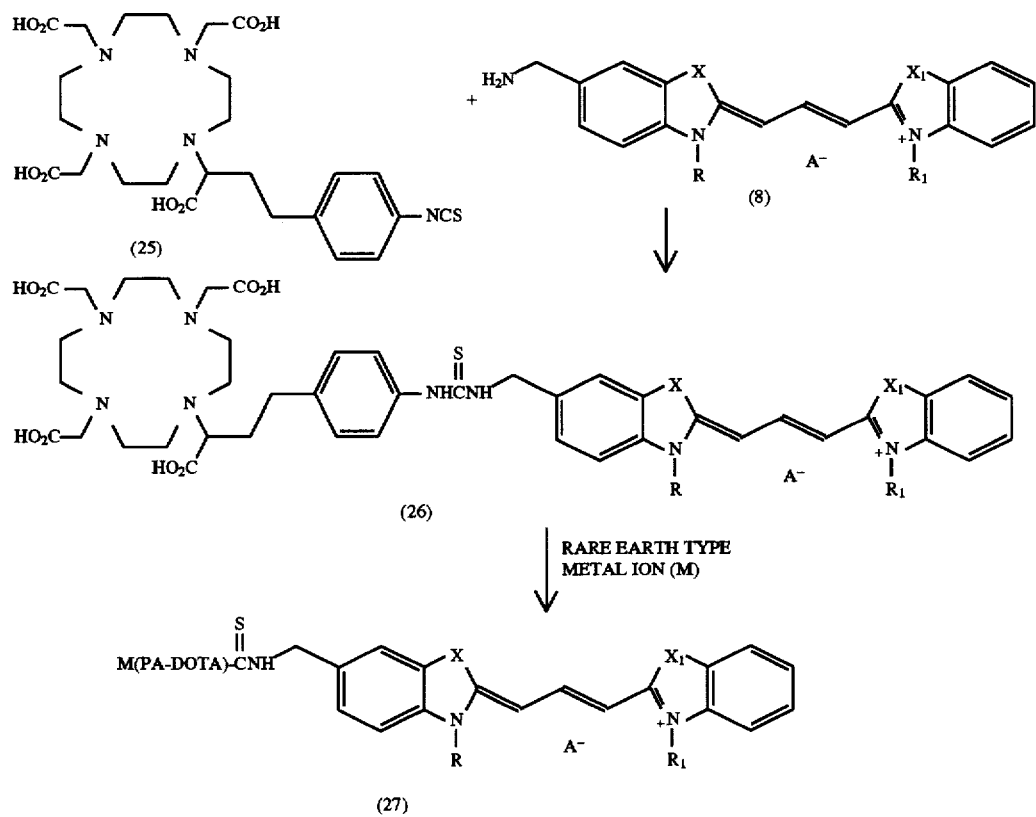

What is claimed is:

1. A compound having the formula:

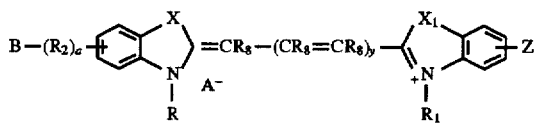

wherein B represents a chemotherapeutic substance; R and R₁ are substituents independently selected from the group consisting of hydrogen, alkyl, alkenyl, alkynyl, alkaryl and aralkyl, the hydrocarbon chains of which having from 1 to about 30 carbon atoms, and being linear or branched, said substituents being unsubstituted or substituted with one or more non-polar functional groups, one of R or R₁ having at least 12 linear carbon atoms, and the sum of the linear carbon atoms in R and R₁ being sufficient to impart a membrane binding stability of at least 30% to said compound;

R₂ represents a spacer moiety of the formula: —(R₃)$_p$—Q—(R₄—Q')$_q$—(R₅—Q'')—(R₆—Q''')$_a$—(R₇Q'''')$_r$— wherein R₃ represents an aliphatic hydrocarbon, R₄, R₅, R₆ and R₇ are independently selected from the group consisting of aliphatic, alicyclic or aromatic hydrocarbons, heterocycles, and CH₂C(CO₂M)=CH, Q and Q', Q'', Q''' and Q'''' are independently selected from the group of functional linkages consisting of amide, thiourea, hydrazone, acyl hydrazone, ketal, acetal, orthoester, ester, anhydride, disulfide, urea, carbamate, imine, amine, ether, carbonate, thioether, sulfonamide carbonyl and amidine linkages; Q', Q'', Q''', Q'''' may additionally independently represent a valence bond; said aliphatic hydrocarbons having from 1 to 12 linear carbon atoms; said aromatic hydrocarbons having from 6 to 12 carbon atoms; n, p, q, r, s, and t each may be either 0 or 1;

X and X₁ may be the same or different and represent O, S, C(CH₃)₂ or Se;

R₈ is independently selected from the group consisting of H, CE₃, CH₂CH₃, CH₂CH₂CH₃ and CH(CH₃)₂; y may be from 0 to 3;

Z represents a substituent selected from the group consisting of H, alkyl, OH, —O—alkyl, COOH, CONH₂, SO₃H, SO₂NH₂, SH, S-alkyl, CONH-alkyl, CON-(alkyl)₂, NH-acyl, NH-alkyl, N(alkyl)₂, NO₂, halogen, Si(alkyl)₃, O-Si(alkyl)₃, Sn(alkyl)₃ and —Hg— halogen, the alkyl groups comprising said Z substituent having from 1 to 4 carbon and A represents a pharmaceutically acceptable anion.

2. A compound as claimed in claim 1, comprising a radioisotope selected from the group consisting of radioactive hydrogen, carbon, nitrogen, halogen, sulphur, selenium or a combination thereof.

3. A compound as claimed in claim 1, wherein said chemotherapeutic substance is selected from the group consisting of immunogens, toxins, hormones, enzymes, antigens, antibodies and antibody fragments.

4. A compound, according to claim 1 of the formula:

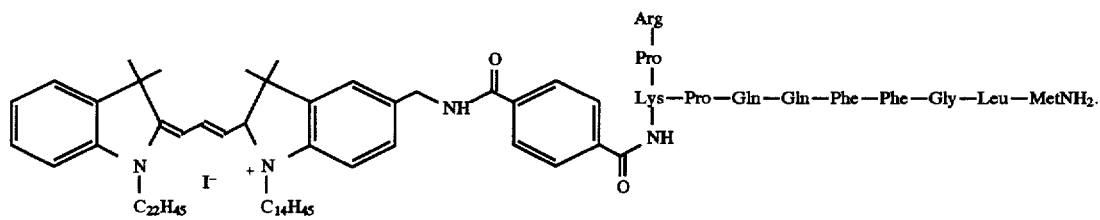

5. A compound, according to claim 1, of the formula:

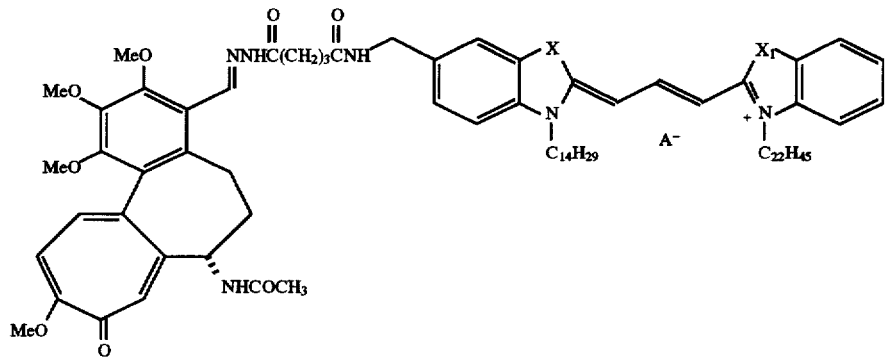

6. A compound, according to claim 1, of the formula:

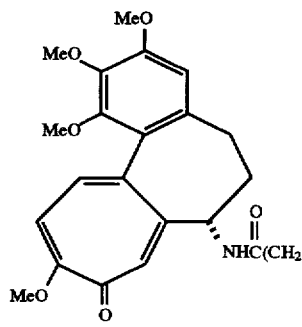
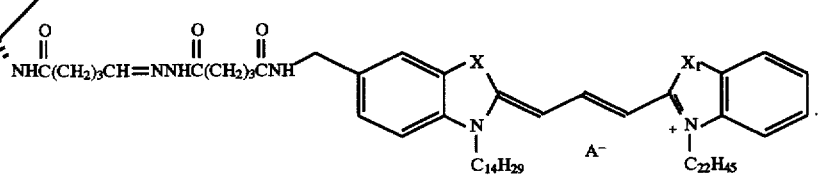

7. A compound as claimed in claim 1, wherein said chemotherapeutic substance comprises a nucleic acid.

8. A compound as claimed in claim 1, wherein said chemotherapeutic agent comprises an anitproliferative agent.

9. A compound as claimed in claim 8, wherein said antiproliferative agent is selected from the group consisting of colchicine, vinca alkaloids, taxol and derivatives thereof.

10. A compound as claimed in claim 8, wherein said chemotherapeutic substance comprises an anticoagulant.

11. A compound as claimed in claim 10, wherein said anticoagulant is selected from the group consisting of heparin, heparin fragments and heparin derivatives.

12. A compound as claimed in claim 10, wherein said anticoagulant is selected from the group consisting of hirudin and hirudin derivatives.

* * * * *